＝

US011395801B2

(12) United States Patent
Karaborni et al.

(10) Patent No.: US 11,395,801 B2
(45) Date of Patent: *Jul. 26, 2022

(54) MODIFIED RELEASE COMPOSITIONS OF A GAMMA-HYDROXYBUTYRIC ACID DERIVATIVE

(71) Applicant: XWPHARMA LTD., Grand Cayman (KY)

(72) Inventors: Sami Karaborni, Cupertino, CA (US); Daniel M. Canafax, Half Moon Bay, CA (US); Jia-Ning Xiang, Fremont, CA (US); William W. Xiang, Fremont, CA (US); James Tien, Wuhan (CN); Stefanie Thiel, Binzen (DE); Norbert Pollinger, Binzen (DE); Annette Grave, Binzen (DE)

(73) Assignee: XWPHARMA LTD., Grand Cayman (KY)

( * ) Notice: Subject to any disclaimer, the term of this patent is extended or adjusted under 35 U.S.C. 154(b) by 0 days.

This patent is subject to a terminal disclaimer.

(21) Appl. No.: 17/494,749

(22) Filed: Oct. 5, 2021

(65) Prior Publication Data

US 2022/0105044 A1 Apr. 7, 2022

Related U.S. Application Data

(60) Provisional application No. 63/087,515, filed on Oct. 5, 2020.

(51) Int. Cl.
*A61K 9/28* (2006.01)
*A61K 9/20* (2006.01)

(52) U.S. Cl.
CPC .......... *A61K 9/2866* (2013.01); *A61K 9/2009* (2013.01); *A61K 9/2013* (2013.01); *A61K 9/2054* (2013.01)

(58) Field of Classification Search
CPC .. A61K 9/2866; A61K 9/2009; A61K 9/2013; A61K 9/2054
See application file for complete search history.

(56) References Cited

U.S. PATENT DOCUMENTS

| 4,370,338 | A | 1/1983 | Mizoule |
| 5,110,797 | A | 5/1992 | Ienaga et al. |
| 6,489,350 | B1 | 12/2002 | Benedyk et al. |
| 7,482,429 | B2 | 1/2009 | Albericio et al. |
| 7,521,455 | B2 | 4/2009 | Nagase et al. |
| 7,960,561 | B2 | 6/2011 | Sorensen et al. |
| 8,529,954 | B2 | 9/2013 | Lebon et al. |
| 8,598,191 | B2 | 12/2013 | Liang et al. |
| 9,309,182 | B2 | 4/2016 | Tung et al. |
| 10,398,662 | B1 | 9/2019 | Allphin et al. |
| 10,457,627 | B2 | 10/2019 | Xiang et al. |
| 10,501,401 | B2 | 12/2019 | Xiang et al. |
| 10,640,451 | B2 | 5/2020 | Xiang et al. |
| 10,774,031 | B2 | 9/2020 | Xiang et al. |
| 2004/0214755 | A1 | 10/2004 | Albericio et al. |
| 2005/0182045 | A1 | 8/2005 | Nagase et al. |
| 2006/0122383 | A1 | 6/2006 | Zhou et al. |
| 2006/0210630 | A1 | 9/2006 | Liang et al. |
| 2008/0175873 | A1 | 7/2008 | Zhou et al. |
| 2010/0144869 | A1 | 6/2010 | Nudelman et al. |
| 2011/0111027 | A1 | 5/2011 | Rourke et al. |
| 2011/0178068 | A1 | 7/2011 | Almarsson et al. |
| 2011/0293729 | A1 | 12/2011 | Lebon et al. |
| 2012/0283300 | A1 | 11/2012 | Kim et al. |
| 2016/0052862 | A1 | 2/2016 | Frost et al. |
| 2018/0193277 | A1 | 7/2018 | Suplie et al. |
| 2019/0183806 | A1 | 6/2019 | Guillard |
| 2020/0009076 | A1 | 1/2020 | Patel et al. |
| 2020/0223783 | A1 | 7/2020 | Xiang et al. |
| 2020/0276142 | A1 | 9/2020 | Grassot et al. |
| 2022/0023247 | A1 | 1/2022 | Xiang et al. |

FOREIGN PATENT DOCUMENTS

| CN | 1422278 | 6/2003 |
| CN | 101511388 | 8/2009 |
| CN | 102076342 | 5/2011 |
| CN | 102834098 | 12/2012 |
| CN | 103370289 | 10/2013 |
| DE | 852392 | 10/1952 |
| EP | 0635265 | 1/1995 |
| EP | 2566462 | 3/2013 |
| FR | 2662695 | 12/1991 |
| JP | 62-270552 | 11/1987 |
| JP | 2002-503673 | 2/2002 |
| JP | 2003-522198 | 7/2003 |
| JP | 2004059452 | 2/2004 |
| JP | 2008-526713 | 7/2008 |
| JP | 2013-516465 | 5/2013 |

(Continued)

OTHER PUBLICATIONS

International Search Report and Written Opinion for International Application No. PCT/CN2016/099763, dated Jan. 3, 2017, 15 pages.
International Search Report and Written Opinion for International Application No. PCT/CN2017/078873, dated Jan. 9, 2018, 12 pages.
International Search Report and Written Opinion for International Application No. PCT/CN2018/090151, dated Feb. 20, 2019, 14 pages.
International Search Report and Written Opinion for International Application No. PCT/CN2018/097241, dated Apr. 28, 2019, 11 pages.
International Search Report and Written Opinion for International Application No. PCT/CN2018/109115, dated Jul. 8, 2019, 11 pages.
International Search Report and Written Opinion for International Application No. PCT/CN2018/118565, dated Jul. 8, 2019, dated Apr. 28, 2019, 13 pages.

(Continued)

*Primary Examiner* — Robert A Wax
*Assistant Examiner* — Olga V. Tcherkasskaya

(57) ABSTRACT

Pharmaceutical granulations having a functional coating surrounding a core containing 4-((L-valyl)oxy)butanoic acid are disclosed. The functional coatings provide for immediate release or modified release of 4-((L-valyl)oxy)butanoic acid. The pharmaceutical granulations can be used in oral pharmaceutical compositions.

18 Claims, 26 Drawing Sheets

(56) References Cited

FOREIGN PATENT DOCUMENTS

| RU | 2142800 | 12/1999 |
|---|---|---|
| WO | 1999/041275 | 8/1999 |
| WO | 1999/051613 | 10/1999 |
| WO | 2004/087169 | 10/2004 |
| WO | 2005/123731 | 12/2005 |
| WO | 2006/038226 | 4/2006 |
| WO | 2009/040331 | 4/2009 |
| WO | 2009/102462 | 8/2009 |
| WO | 2009/137717 | 11/2009 |
| WO | 2010/124046 | 10/2010 |
| WO | 2011/119839 | 9/2011 |
| WO | 2013/019561 | 2/2013 |
| WO | 2013/163244 | 10/2013 |
| WO | 2014/031840 | 2/2014 |
| WO | 2014/078014 | 5/2014 |
| WO | 2014/152263 | 9/2014 |
| WO | 2014/205393 | 12/2014 |
| WO | 2015/057884 | 4/2015 |
| WO | 2015/083129 | 6/2015 |
| WO | 2017/049470 | 3/2017 |
| WO | 2017/050259 | 3/2017 |
| WO | 2018/015563 | 1/2018 |
| WO | 2018/098472 | 5/2018 |

OTHER PUBLICATIONS

International Search Report and Written Opinion for PCT Application No. PCT/US2020/066047, dated Mar. 23, 2021, 11 pages.
Non-Final Office Action for U.S. Appl. No. 16/831,086, dated Apr. 13, 2020, 8 pages.
Non-Final Office Action for U.S. Appl. No. 16/791,243, dated Apr. 8, 2020, 20 pages.
Ahn et al., "Hapten and Antibody Production for a Sensitive Immunoassay Determining a Human Urinary Metabolite of the Pyrethroid Insecticide Permethrin," Journal of Agricultural and Food Chemistry, Jun. 2004, vol. 52, No. 15, p. 4583-4594.
Search Report for Australia Application No. 2017406159, dated Feb. 28, 2020, 6 pages.
Search Report for Australia Application No. 2016328150, dated Mar. 27, 2020, 4 pages.
Search Report for Russia Application No. 2019134607, dated Feb. 11, 2020, 7 pages (translation).
Jiang, et al., Copper-Catalyzed Aerobic Oxidative Regioselective Thiocyanation of Aromatics and Heteroaromatics. J. Org. Chem. 2017, 82, 18, 9312-9320.
Jimonet et al., "Riluzole series. Synthesis and in vivo "antiglutamate" activity of 6-substituted-2-benzothiazolamines and 3-substituted-2-imino-benzothiazolines", Journal of Medical Chemistry, 1999, vol. 42, p. 2828-2843.
Jordan, et al., Efficient Conversion of Substituted Aryl Thioureas to 2-Aminobenzothiazoles Using Benzyltrimethylammonium Tribromide. J. Org. Chem. 2003, 68, 22, 8693-8696.
Kaname et al., "One-pot copper-catalyzed tandem addition-cyclization of 2-iodoanilines with isoselenocyanates for the practical preparation of 2-aminobenzoselenazoles," Tetrahedron Letters, Jan. 2011, vol. 52, Issue 4, p. 505-508.
Lee et al., "Development of an Immunoassay for the Residues of the Herbicide Bensulfuron-Methyl," Journal of Agricultural and Food Chemistry, Mar. 2002, vol. 50, No. 7, p. 1791-1803.
Luengo et al., "Synthesis and Structure-Activity Relationships of Macrocyclic FKBP Ligands", Bioorganic & Medicinal Chemistry Letters, 1994, vol. 4, No. 2, p. 321-324.
McGeer et al., "Pharmacologic Approaches to the Treatment of Amyotrophic Lateral Sclerosis", Drug Mechanisms and Targets, 2006, vol. 19, No. 1, p. 31-37.
RN 1243631-58-4, STN entry date Sep. 29, 2010.
STN Columbus, Registry Jul. 21, 1990, 128321-03-09, 81055-72-3.
STN Columbus, Registry Dec. 4, 2015, CAS No. 1822708-15-5.
RN 142229-71-8, STN entry date Jul. 3, 1992.
RN 1211588-05-4, STN REG, Mar. 19, 2010.
RN 1354448-66-0, STN REG, Jan. 25, 2012.
RN 1206250-52-3, STN REG, Feb. 12, 2010.
RN 1206250-51-2, STN REG, Feb. 12, 2010.
RN 1206250-54-5, STN REG, Feb. 12, 2010.
RN 1206248-58-9, STN REG, Feb. 12, 2010.
RN 1744-22-5, STN entry date Nov. 16, 1984.
RN 326-45-4, STN entry date Nov. 16, 1984.
RN 747353-64-6, STN REG, Sep. 17, 2004.
RN 60176-62-7, STN entry date Nov. 16, 1984.
RN 60176-63-8, STN REG, Nov. 16, 1984.
RN 60388-38-7, STN entry date Nov. 16, 1984.
CAS Registry No. 238401-16-6 entry date Sep. 10, 1999.
Rothweiler, et al., Probing the ATP-Binding Pocket of Protein Kinase DYRK1A with Benzothiazole Fragment Molecules. J. Med. Chem. 2016, 59, 21, 9814-9824.
Rynearson et al., "2-Aminobenzoxazole ligands of the hepatitis C virus internal ribosome entry site," Bioorganic & Medicinal Chemistry Letters, Aug. 2014, vol. 24, No. 15, p. 3521-3525.
Sankaranarayanan et al., "Naphtho[1,2-d]thiazol-2-ylamine (SKA-31), a new activator of KCa2 and KCa3.1 potassium channels, potentiates the endothelium-derived hyperpolarizing factor response and lowers blood pressure", Molecular Pharmacology, 2009, vol. 75, p. 281-295.
Staldweiser et al., "Combinatorial Solid-Phase Synthesis of Structurally Complex Thiazolylhydantoines," Angewandte Chemie Int. Ed., A Journal of the German Chemical Society, Jun. 1998, vol. 37, No. 10, p. 1402-1404.
Ward et al., "Discovery of an Orally Bioavailable Nki Receptor Antagonist, (2S, 3S)-(2-Methoxy-5-tetrazol-I-ylbenzyl)(2-phenylpiperidin-3-yl)amine (GR203040), with Potent Antiemetic Activity," Journal of Med. Chem., 1995, vol. 38, p. 4985-4992.
International Search Report and Written Opinion for PCT Application No. PCT/US2021/037830, dated Dec. 7, 2021, 20 pages.
International Search Report and Written Opinion for PCT Application No. PCT/US2021/037909, dated Dec. 2, 2021, 27 pages.
International Search Report and Written Opinion for PCT Application No. PCT/US2021/042818, dated Nov. 12, 2021, 13 pages.
Partial International Search Report and Written Opinion for PCT Application No. PCT/US2021/037830, dated Oct. 6, 2021, 14 pages.
Partial International Search Report and Written Opinion for PCT Application No. PCT/US2021/037909, dated Oct. 4, 2021, 26 pages.
Cameo Chemicals, ethyl-3-hydroxybutyrate, retrieved from https://web.archive.org/web/20170209085248/ https://cameochemicals.noaa.gov/chemical/20385, 2017, 5 pages.
During et al., "Pharmaceutical Technology Report: Water-Soluble Cellulose Ethers as Release Modulators for Ethylcellulose Coatings on Multiparticulates", Annual Meeting of the American Association of Pharmaceutical Scientists, Nov. 2011, 9 pages.
International Search Report and Written Opinion for PCT Application No. PCT/US2021/053640, dated Mar. 3, 2022, 18 pages.

100 μm

20 μm

MODIFIED RELEASE COMPOSITIONS OF A GAMMA-HYDROXYBUTYRIC ACID DERIVATIVE

This application claims the benefit under 35 U.S.C. § 119(e) of U.S. Provisional Application No. 63/087,515 filed on Oct. 5, 2020, which is incorporated by reference in its entirety.

FIELD

The disclosure relates to pharmaceutical granulations of 4-((L-valyl)oxy)butanoic acid having a functional coating. The coated pharmaceutical granulations can be used in modified release oral compositions.

BACKGROUND

In certain methods of treatment, it is necessary to administer a high dose of a pharmaceutically active ingredient. To minimize the amount of an oral pharmaceutical composition administered to a patient in such treatments, it is desirable that the pharmaceutical composition contain a high content of the pharmaceutically active ingredient and that the amount of pharmaceutical excipients be minimized.

Oral modified-release dosage forms can contain granules coated with a functional coating that provides a desired release profile in the gastrointestinal tract.

Modified release compositions containing pharmaceutical granulations having a high bulk density of an active pharmaceutical ingredient and suitable for dosing once or two times a day are desired. To improve palatability, it is desirable that the pharmaceutical granulations have a low average particle size such as from 200 μm to 400 μm.

SUMMARY

According to the present invention, a modified release pharmaceutical granulation comprises a plurality of coated granules, wherein, the granules comprise a core and a modified release coating surrounding the core, wherein the modified release coating comprises: from 50 wt % to 85 wt % of a matrix polymer; and from 10 wt % to 20 wt % an antistatic agent; wherein wt % is based on the total weight of the modified release coating. the pharmaceutical granulation is characterized by a particle size distribution (PSD) (D50) from 200 μm to 400 μm, wherein PSD is determined by sieve analysis; and the core comprises greater than 90 wt % of 4-((L-valyl)oxy)butanoic acid, wherein wt % is based on the total weight of the core.

According to the present invention, a pharmaceutical composition comprises a pharmaceutical granulation according to the present invention.

According to the present invention, methods of coating a granulation comprise applying a coating composition to a pharmaceutical granulation comprising a plurality of granules comprising 4-((L-valyl)oxy)butanoic acid, wherein the coating composition comprises: from 6 wt % to 14 wt % solids; from 0 wt % to 20 wt % water; and from 70 wt % to 95 wt % ethanol, wherein wt % is based on the total weight of the coating formulation.

According to the present invention, pharmaceutical compositions comprise: an immediate release (IR) component, wherein the immediate release component comprises from 1.2 g-equivalents γ-hydroxybutyrate to 4.0 g-equivalents γ-hydroxybutyrate; and a modified release (MR) component, wherein the modified release component comprises: from 3 g-equivalents γ-hydroxybutyrate to 9 g-equivalents γ-hydroxybutyrate; and the modified release granulation according to the present invention.

According to the present invention, methods of treating fatigue or excessive daytime sleepiness associated with narcolepsy in a patient comprise orally administering to a patient in need of such treatment a therapeutically effective amount of the pharmaceutical composition according to the present invention.

According to the present invention, methods of treating narcolepsy, excessive daytime sleepiness, cataplexy, excessive daytime sleepiness associated with narcolepsy, excessive daytime sleepiness associated with Parkinson's disease, excessive daytime sleepiness associated with multiple sclerosis, cataplexy associated with narcolepsy, fatigue, fatigue associated with Parkinson's diseases, fatigue associated with multiple sclerosis, or fibromyalgia in a patient comprise orally administering to a patient in need of such treatment a therapeutically effective amount of the pharmaceutical composition according to the present invention.

According to the present invention, kits comprise a pharmaceutical composition according to the present invention.

BRIEF DESCRIPTION OF THE DRAWINGS

Those skilled in the art will understand that the drawings described herein are for illustration purposes only. The drawings are not intended to limit the scope of the present disclosure.

DETAILED DESCRIPTION

Figure 1:
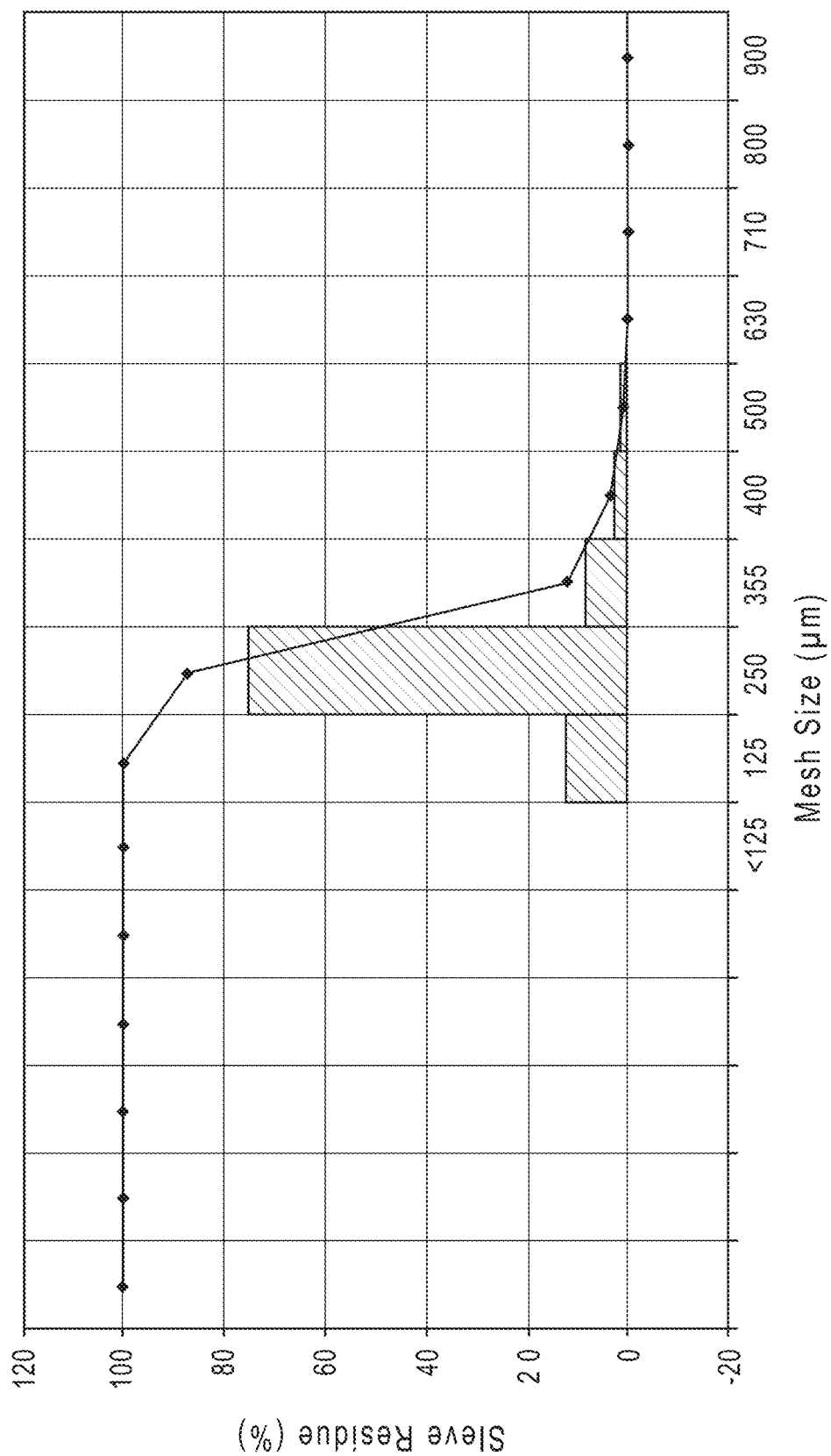
FIG. 1 shows the particle size distribution of granules comprising a hydroxypropylmethyl cellulose seal coating as described in Example 1.

For purposes of the following detailed description, it is to be understood that embodiments provided by the present disclosure may assume various alternative variations and step sequences, except where expressly specified to the contrary. Moreover, other than in any operating examples, or where otherwise indicated, all numbers expressing, for example, quantities of ingredients used in the specification and claims are to be understood as being modified in all instances by the term "about." Accordingly, unless indicated to the contrary, the numerical parameters set forth in the following specification and attached claims are approximations that may vary depending upon the desired properties to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard variation found in their respective testing measurements.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10.

"Functional coatings" include immediate release coatings, controlled release coatings, modified release coatings, sustained release coatings, pH-release coatings, pulsatile release coatings, timed-release coatings, and delayed release coatings. A functional coating is configured to provide a desired property to the granulation comprising 4-((L-valyl)oxy)butanoic acid such as a desired release profile in the gastrointestinal tract following oral administration.

"Immediate release" refers to a pharmaceutical composition that releases substantially all of an pharmaceutically active ingredient into the gastrointestinal tract of a patient within less than 1 hour following oral administration, such as within less than 50 minutes, within less than 40 minutes, within less than 30 minutes, within less than 20 minutes, or within less than 10 minutes following oral administration. For example, an immediate release dosage form can release greater than 90%, greater than 95%, or greater than 98% of the pharmaceutically active ingredient in the pharmaceutical composition into the gastrointestinal tract within less than 1 hour such as within less than 50 minutes, less than 40 minutes, less than 30 minutes, less than 20 minutes, or less than 10 minutes, following oral administration. Immediate release pharmaceutical compositions can be appropriate to administer pharmaceutically active ingredients that are absorbed into the systemic circulation from the upper portion of the gastrointestinal tract.

"Modified release" pharmaceutical compositions include controlled release compositions, delayed release compositions, extended release compositions, sustained release compositions, timed release compositions, pulsatile release compositions, and pH-dependent release compositions. These compositions are intended to release a pharmaceutically active ingredient from the pharmaceutical composition at a desired rate and/or at a desired time following oral administration by a patient and/or at a certain location or locations within the gastrointestinal tract and/or at a certain pH within the gastrointestinal tract. The USP defines a modified release system as one in which the time course or location of drug release or both, are chosen to accomplish objectives of therapeutic effectiveness or convenience not fulfilled by immediate release dosage forms. A modified release oral dosage form can include extended release and delayed-release components. A delayed release dosage form is one that releases a drug all at once at a time other than promptly after administration. A modified release composition can include delayed-release using enteric coatings, site-specific or timed release such as for colonic delivery, extended-release including, for example, compositions capable of providing zero-order, first-order, or biphasic release profiles, and programmed release such as pulsatile and delayed extended release.

"Sustained release" pharmaceutical compositions and coatings provide for a dissolution rate over an extended period of time following oral administration. Granulations comprising granules having a sustained release coating can be referred to as sustained release granulations. A pharmaceutical composition comprising a sustained release granulation can be referred to as a sustained release pharmaceutical composition.

"pH-Release" pharmaceutical compositions and coatings provide for an increased dissolution rate at an intended pH.

"Pulsatile release" pharmaceutical compositions and coatings exhibit an increased dissolution rate at intervals, where the release intervals can be determined by time, exposure to internal stimuli, or exposure to external stimuli. Examples of pulsatile-release systems include capsular systems, osmotic systems, systems having erodible membranes, and systems having a rupturable coating. Examples of stimuli include temperature, chemicals, electrical stimuli, and magnetic stimuli.

"Timed-release" pharmaceutical compositions and coatings have a dissolution rate that is a function of time. A time-release pharmaceutical composition or coating includes, for example, delayed release, sustained release, and extended release pharmaceutical compositions and coatings.

"Delayed release" pharmaceutical compositions and coatings provide for an increased dissolution rate at an intended time after administration.

"Immediate release component" refers to a component of a pharmaceutical composition comprising immediate release microparticles provided by the present disclosure.

"Modified release component" refers to a component of a pharmaceutical composition comprising modified release microparticles provided by the present disclosure.

"Controlled release pharmaceutical composition" refers to a pharmaceutical composition comprising immediate release microparticles provided by the present disclosure and modified release microparticles provided by the present disclosure.

The terms granules and microparticles are used interchangeably.

"Patient" refers to a mammal, for example, a human.

"Pharmaceutically acceptable" refers to approved or approvable by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound, which possesses the desired pharmacological activity of the parent compound. Such salts include acid addition salts, formed with inorganic acids and one or more protonatable functional groups such as primary, secondary, or tertiary amines within the parent compound. Examples of suitable inorganic acids include hydrochloric acid, hydrobromic acid, sulfuric acid, nitric acid, phosphoric acid, and the like. A salt can be formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo [2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like. A salt can be formed when one or more acidic protons present in the parent compound are replaced by a metal ion, e.g., an alkali metal ion, an alkaline earth ion, or an aluminum ion, or combinations thereof; or coordinates with an organic base such as ethanolamine, diethanolamine, triethanolamine, N-methylglucamine, and the like. A pharmaceutically acceptable salt can be the hydrochloride salt. A pharmaceutically acceptable salt can be the sodium salt. In compounds having two or more ionizable groups, a pharmaceutically acceptable salt can comprise one or more counterions, such as a bi-salt, for example, a dihydrochloride salt.

The term "pharmaceutically acceptable salt" includes hydrates and other solvates, as well as salts in crystalline or non-crystalline form. Where a particular pharmaceutically acceptable salt is disclosed, it is understood that the particular salt (e.g., a hydrochloride salt) is an example of a salt, and that other salts may be formed using techniques known to one of skill in the art. Additionally, one of skill in the art would be able to convert the pharmaceutically acceptable salt to the corresponding compound, free base and/or free acid, using techniques generally known in the art.

"Percent weight gain" or "% wg" such as in a "35% wg" coating refers to a coated granule or granulation in which the weight of the coated granule or granulation is greater than the weight of the granule or granulation without the coating by the indicated percent (%). For example, a 35% wg particle has a coating that increases that weight of the uncoated particle by 35%. For example, for a granulation having an initial weight of 100 gm, adding a 35% wg coating increases the weight of the granulation to 135 gm. The coating comprises 25.9 wt % of the total weight of the granulation.

Dissolution profiles were measured using a USP Type 2 dissolution apparatus and a sodium acetate buffered solution at pH 4.5 at a temperature of 37° C. and a paddle speed of 100 rpm.

A value that is "bioequivalent" refers to a pharmacokinetic value such as the $C_{max}$ or AUC that exhibits substantially similar pharmacokinetic profiles and/or therapeutic effects. Bioequivalence may be demonstrated by several in vivo and in vitro methods. These methods may include, for example, pharmacokinetic, pharmacodynamic, clinical and in vitro studies. Bioequivalence can be demonstrated using any suitable pharmacokinetic measures or combination of pharmacokinetic measures known in the art, including loading dose, steady-state dose, initial or steady-state concentration of drug, biological half-life, elimination rate, area under the curve (AUC), clearance, the peak blood or plasma concentration ($C_{max}$), time to peak concentration ($T_{max}$), bioavailability and potency. A value can be bioequivalent to a reference pharmacokinetic value when the geometric mean of the AUC and/or the $C_{max}$ is between 80% and 125% (e.g., at 90% confidence interval) of the reference pharmacokinetic value.

A similar or bioequivalent pharmacokinetic profile refers to a pharmacokinetic profile for which the mean $AUC_{0-inf}$ of a pharmaceutical composition is from 80% to 125% of the mean $AUC_{0-inf}$ a reference composition in a suitably designed cross-over trial, the mean plasma concentration at 8 hours $C_{8h}$ of the pharmaceutical composition is from 40% to 130% of the mean plasma concentration at 8 hours $C_{8h}$ of the reference composition, and/or that the maximum plasma concentration ($C_{max}$) of the pharmaceutical composition is from 50% to 140% of the $C_{max}$ of the reference composition.

A "fed state" refers to the period of time immediately after consumption of a meal up to two hours post consumption. The fed state can include the period less than two hours after eating.

A "fasted state" refers to the period of time after 8 hours post meal consumption.

"Prodrug" refers to a derivative of a drug molecule that requires a transformation within the body to provide the active drug. Prodrugs are frequently, although not necessarily, pharmacologically inactive until converted to the parent drug. Prodrugs may be obtained by bonding a promoiety typically via a functional group, to a parent drug.

"Curing" a disease refers to eliminating a disease or disorder or eliminating a symptom of a disease or disorder.

"Treating" or "treatment" of a disease or disorder refers to reducing the severity of one or more clinical symptom of the disease or disorder, delaying the onset of one or more clinical symptoms of the disease or disorder, and/or mitigating one or more clinical symptoms of the disease or disorder.

"Treating" or "treatment" of a disease or disorder refers to inhibiting the disease or disorder or one or more clinical symptoms of the disease or disorder, arresting the development of the disease or disorder or one or more clinical symptoms of the disease or disorder, relieving the disease or disorder or one or more clinical symptoms of the disease or disorder, causing the regression of the disease or disorder or one or more clinical symptoms of the disease or disorder, and/or stabilization of the disease or disorder or one or more clinical symptoms of the disease or disorder, "Treating" or "treatment" of a disease or disorder refers to producing a clinically beneficial effect without curing the underlying disease or disorder.

"Therapeutically effective amount" refers to the amount of a compound such as pharmaceutically active ingredient that, when administered to a patient for treating a disease, or at least one of the clinical symptoms of a disease, is sufficient to affect such treatment of the disease or symptom thereof. A "therapeutically effective amount" may vary depending, for example, on the compound, the disease and/or symptoms of the disease, the severity of the disease and/or symptoms of the disease or disorder, the age, weight, and/or health of the patient to be treated, and the judgment of the prescribing physician. A therapeutically effective amount in any given instance may be ascertained by those skilled in the art or capable of determination by routine experimentation.

"Therapeutically effective dose" refers to a dose that provides effective treatment of a disease or disorder in a patient. A therapeutically effective dose may vary from compound to compound, and from patient to patient, and may depend upon factors such as the condition of the patient and the route of delivery. A therapeutically effective dose may be determined in accordance with routine pharmacological procedures known to those skilled in the art.

"Vehicle" refers to a diluent, excipient or carrier with which a compound is administered to a patient. A vehicle can be a pharmaceutically acceptable vehicle. Pharmaceutically acceptable vehicles are known in the art.

Reference is now made to pharmaceutical granulations having a functional coating, methods of making coated pharmaceutical granulations, and pharmaceutical compositions comprising coated pharmaceutical granulations. The disclosed coated pharmaceutical granulations, compositions comprising the coated pharmaceutical granulations, and methods of making the coated pharmaceutical granulations are not intended to be limiting of the claims. To the contrary, the claims are intended to cover all alternatives, modifications, and equivalents.

4-((L-Valyl)oxy)butanoic acid is a prodrug of γ-hydroxybutyric acid. When orally administered 4-((L-valyl)oxy)butanoic acid is absorbed from the gastrointestinal tract and is metabolized in the systemic circulation to release γ-hydroxybutyric acid. γ-Hydroxybutyric acid can be used to treat diseases and disorders such as narcolepsy, cataplexy, excessive daytime sleepiness, fibromyalgia, chronic fatigue, and tardive dyskinesia.

Coated pharmaceutical granulations provided by the present disclosure can be used to provide modified release of 4-((L-valyl)oxy)butanoic acid following oral administration to a patient. The coated pharmaceutical granulations contain 4-((L-valyl)oxy)butanoic acid, which is a hygroscopic, highly water-soluble pharmaceutically active ingredient that is prone to hydrolysis. The coated pharmaceutical granulations can be used to provide modified release oral pharmaceutical compositions. The coated pharmaceutical granulations can be used to orally administer high doses of 4-((L-valyl)oxy)butanoic acid.

Modified-release granulations provided by the present disclosure can be prepared by coating granules comprising 4-((L-valyl)oxy)butanoic acid. The granules comprising 4-((L-valyl)oxy)butanoic acid can be uncoated or can comprise a seal coating.

An uncoated pharmaceutical granulation provided by the present disclosure can comprise a plurality of granules, where the granules can comprise greater than 90 wt % of 4-((L-valyl)oxy)butanoic acid, where wt % is based on the total weight of the granules; and the uncoated pharmaceutical granulation can be characterized by a particle size distribution (PSD) (D50) from 150 μm to 400 μm, from 150 μm to 350 μm, from 150 μm to 300 μm, from 200 μm to 400 μm, from 200 μm to 300 μm, from 250 μm to 350 μm, or from 225 μm to 275 μm, where PSD is determined by sieve analysis; and wt % is based on the total weight of the pharmaceutical granulation.

An uncoated granule can comprise a high loading of 4-((L-valyl)oxy)butanoic acid. For example, a granule can comprise greater than 90 wt %, greater than 93 wt %, greater than 96 wt %, greater than 97 wt %, greater than 98 wt % or greater than 99 wt % of 4-((L-valyl)oxy)butanoic acid, where wt % is based on the total weight of the uncoated granule. An uncoated granule can comprise, for example, from 90 wt % to 99.5 wt %, from 95 wt % to 99.5 wt % of a γ-hydroxybutyric acid derivative, from 96 wt % to 99 wt %, from 97 wt % to 99 wt %, or from 98 wt % to 99 wt % of 4-((L-valyl)oxy)butanoic acid, where wt % is based on the total weight of the uncoated granule.

4-((L-Valyl)oxy)butanoic acid has the structure of Formula (1):

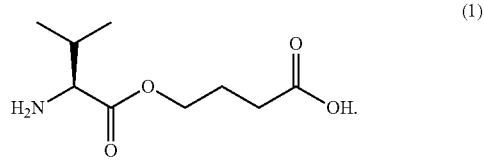

(1)

4-((L-Valyl)oxy)butanoic acid is a prodrug of γ-hydroxybutyric acid (GHB) having the structure of Formula (2):

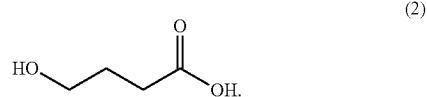

(2)

Following administration such as oral administration, 4-((L-valyl)oxy)butanoic acid is metabolized in the systemic circulation to release γ-hydroxybutyric acid in the plasma of a patient. 4-((L-Valyl)oxy)butanoic acid provides an oral bioavailability of γ-hydroxybutyric acid in a patient of greater than 60% F. [78] Pharmaceutical compositions provided by the present disclosure comprise pharmaceutical granulations comprising granules of 4-((L-valyl)oxy)butanoic acid coated with a functional coating.

Before forming into granules, 4-((L-valyl)oxy)butanoic acid can have a low bulk density.

4-((L-Valyl)oxy)butanoic acid can have a bulk density, for example, less than 0.20 g/mL, less than 0.30 g/mL, less than 0.40 g/mL, or less than 0.50 g/mL.

4-((L-Valyl)oxy)butanoic acid can have a bulk density, for example, from 0.15 g/mL to 0.33 g/mL, from 0.16 g/mL to 0.32 g/mL, from 0.17 g/mL to 0.31 g/mL, from 0.18 g/mL to 0.30 g/mL, from 0.19 g/mL to 0.29 g/mL, or from 0.20 g/mL to 0.28 g/mL.

4-((L-Valyl)oxy)butanoic acid can have a particle size distribution characterized, for example, by a D10 from 1 μm to 3 μm, a D50 from 6.5 μm to 8.5 μm, and a D90 from 15 μm to 17 μm, where particle size distribution is measured by laser diffraction.

4-((L-Valyl)oxy)butanoic acid can have a particle size distribution characterized, for example, by a D50 from 5 μm to 15 μm, from 6 μm to 14 μm, from 7 μm to 13 μm, from 8 μm to 12 μm, or from 9 μm to 11 μm, where particle size distribution is measured by laser diffraction.

4-((L-Valyl)oxy)butanoic acid can be jet milled to reduce the particle size.

Uncoated granulations comprising 4-((L-valyl)oxy)butanoic acid can be prepared using MicroPX® micro-pelletizing technology (Glatt GmbH).

For high dose pharmaceutical compositions of 4-((L-valyl)oxy)butanoic acid, especially when reconstituted as a suspension before administration, to improve palatability it can be useful that uncoated and coated granules have a small mean diameter.

An uncoated pharmaceutical granulation of 4-((L-valyl)oxy)butanoic acid can be characterized, for example, by a PSD (D50) from 75 μm to 450 μm, from 100 μm to 400 μm, from 150 μm to 350 μm, from 200 μm to 350 μm, from 200 μm to 300 μm, from 250 μm to 350 μm or from 225 μm to 275 μm, where the PSD is determined by sieve analysis or by laser diffraction.

An uncoated granule can comprise a high loading of 4-((L-valyl)oxy)butanoic acid. For example, an uncoated granule can comprise greater than 80 wt %, greater than 85 wt %, greater than 90 wt %, greater than 95 wt %, greater than 96 wt %, greater than 97 wt %, greater than 98 wt %, or greater than 99 wt % of 4-((L-valyl)oxy)butanoic acid, where wt % is based on the total weight of the uncoated granule. An uncoated granule can comprise, for example, from 95 wt % to 99.5 wt % of 4-((L-valyl)oxy)butanoic acid, from 96 wt % to 99 wt %, from 97 wt % to 99 wt %, or from 98 wt % to 99 wt % of 4-((L-valyl)oxy)butanoic acid, where wt % is based on the total weight of the uncoated granule.

An uncoated granule or granulation provided by the present disclosure can comprise, for example, greater than 85 wt % of 4-((L-valyl)oxy)butanoic acid, from 1 wt % to 10 wt % of an antistatic agent such as magnesium silicate (talc), and from 1 wt % to 10 wt % of a water-soluble polymer such as hydroxypropylmethyl cellulose, where wt % is based on the total weight of the granule or granulation. An uncoated granule or granulation provided by the present disclosure can comprise, for example, greater than 90 wt % of 4-((L-valyl)oxy)butanoic acid, from 2 wt % to 8 wt % of an antistatic agent such as magnesium silicate (talc), and from 2 wt % to 8 wt % of a water-soluble polymer such as hydroxypropylmethyl cellulose, where wt % is based on the total weight of the granule or granulation. An uncoated granule or granulation provided by the present disclosure can comprise, for example, greater than 90 wt % of 4-((L-valyl)oxy)butanoic acid, from 3 wt % to 7 wt % of an antistatic agent such as magnesium silicate (talc), and from 3 wt % to 7 wt % of a water-soluble polymer such as hydroxypropylmethyl cellulose, where wt % is based on the total weight of the granule or granulation.

An uncoated granule provided by the present disclosure can be characterized by a sphericity, for example, from 0.90 to 1, such as from 0.91 to 0.99, or from 0.92 to 0.98, where sphericity is determined using wet dispersion particle shape methods or by dynamic image analysis. An uncoated granule provided by the present disclosure can be characterized by a sphericity, for example, greater than 0.90, greater than 0.91, greater than 0.92, greater than 0.93, greater than 0.94, or greater than 0.95.

An uncoated granulation provided by the present disclosure can be comprise a plurality of granules characterized by a mode sphericity, for example, from 0.90 to 1, such as from 0.91 to 0.99, or from 0.92 to 0.98, where sphericity is determined using wet dispersion particle shape methods or by dynamic image analysis. An uncoated granulation provided by the present disclosure can comprise a plurality of granules characterized by an average sphericity, for example, greater than 0.94, greater than 0.95, greater than 0.96, greater than 0.97, greater than 0.98, or greater than 0.99.

Uncoated granules provided by the present disclosure are solid and are characterized by a substantially homogeneous composition throughout the granule.

Pharmaceutical granulations provided by the present disclosure can comprise a seal coating. Pharmaceutical granulations comprising a seal coating can be used as immediate release pharmaceutical granulations.

Pharmaceutical granulations provided by the present disclosure can comprise a seal coating covering granules comprising 4-((L-valyl)oxy)butanoic acid.

A seal coating can comprise a water-soluble polymer such as hydroxypropyl cellulose, hydroxypropylmethyl cellulose or any of the water-soluble polymers disclosed herein.

A seal coating can comprise an antistatic agent such as talc, magnesium stearate, or a combination thereof[97] A seal coating can comprise, for example, from 65 wt % to 95 wt % of a water soluble polymer, such as from 70 wt % to 90 wt %, or from 75 wt % to 85 wt % of a water soluble polymer; and from 5 wt % to 35 wt % of an antistatic agent, such as from 10 wt % to 30 wt %, or from 15 wt % to 25 wt % if an antistatic agent where wt % is based on the total weight of the seal coating.

A seal coating can have a thickness, for example, from 0.5 μm to 4 μm, from 1 μm to 3.5 μm, from 1 μm to 3 μm, or from 1 μm, to 2.5 μm.

Examples of methods of coating granules comprising 4-((L-valyl)oxy)butanoic acid with a seal coat are provided in Examples 1 and 2.

Figure 3:
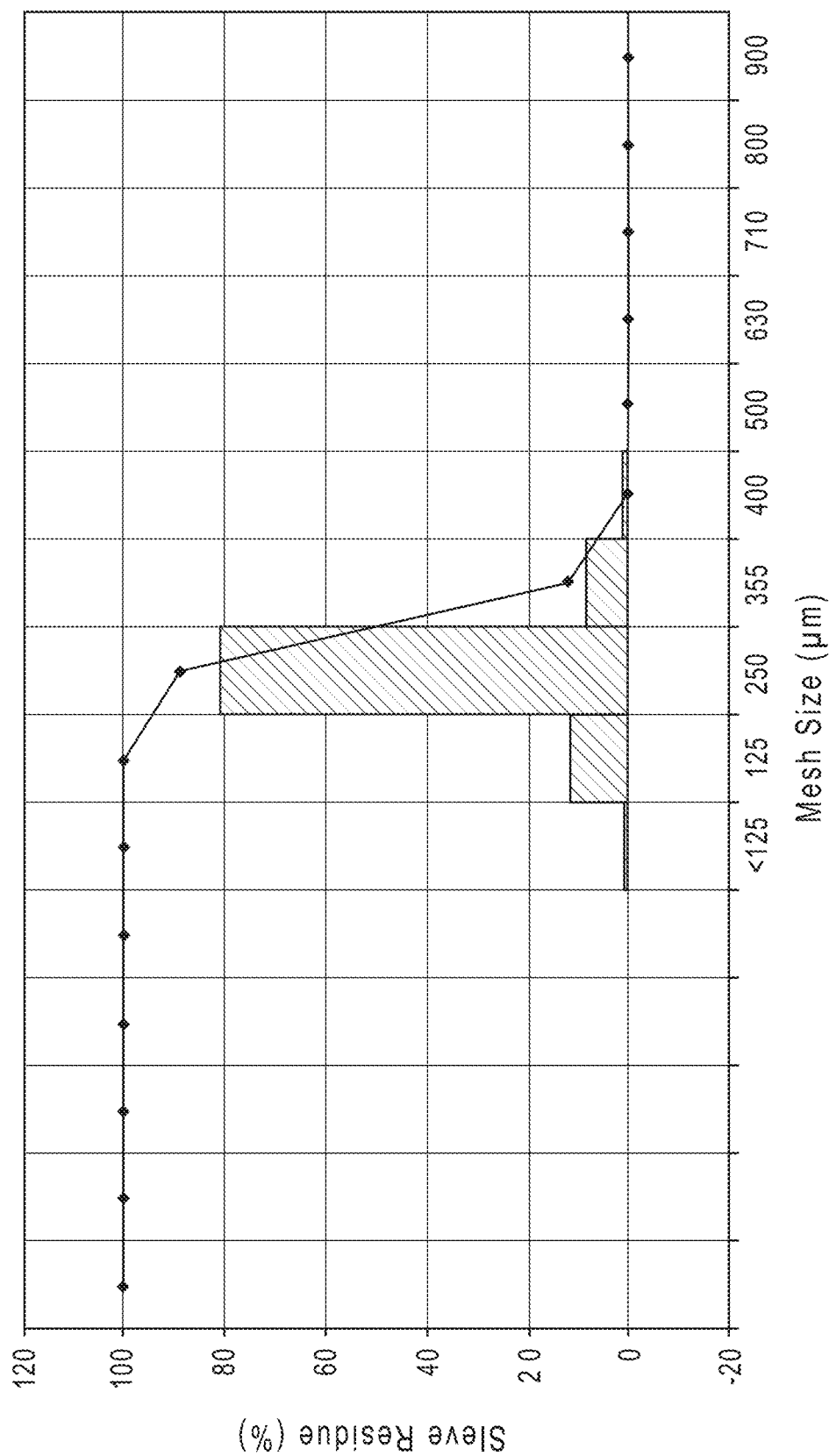
FIG. 3 shows the particle size distribution of granules comprising a hydroxypropyl cellulose seal coating as described in Example 2.

FIGS. 1 and 3 show particle size distributions of seal-coated granulations.

Figure 2A:
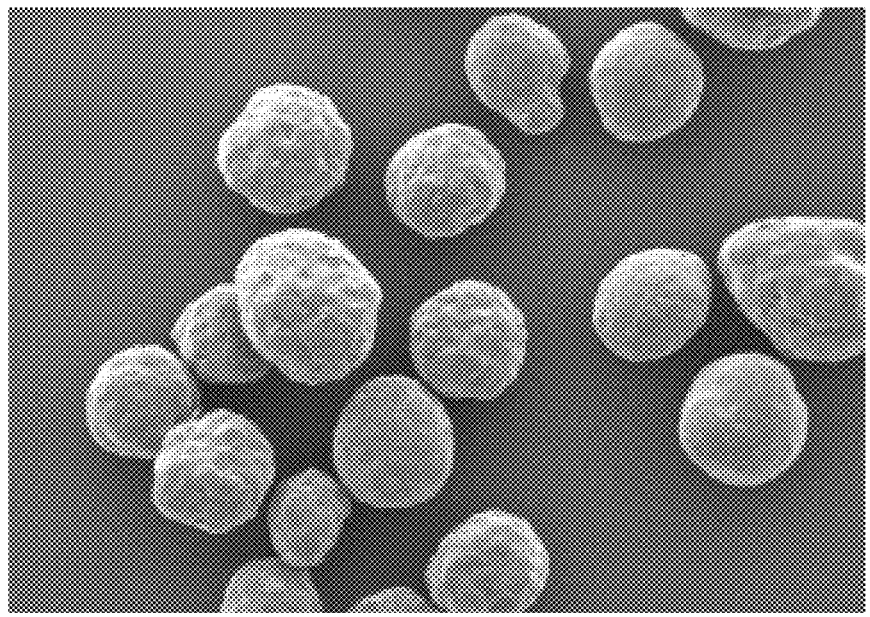
FIGS. 2A-2E show scanning electron microscopy (SEM) images of seal-coated granules at different magnifications as described in Example 1.
Figure 2B:
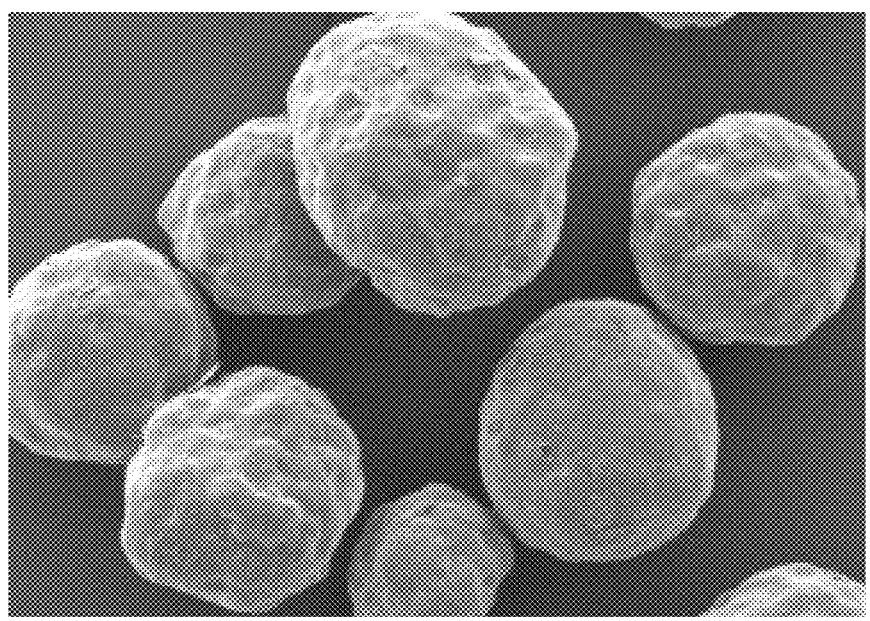
Figure 2C:
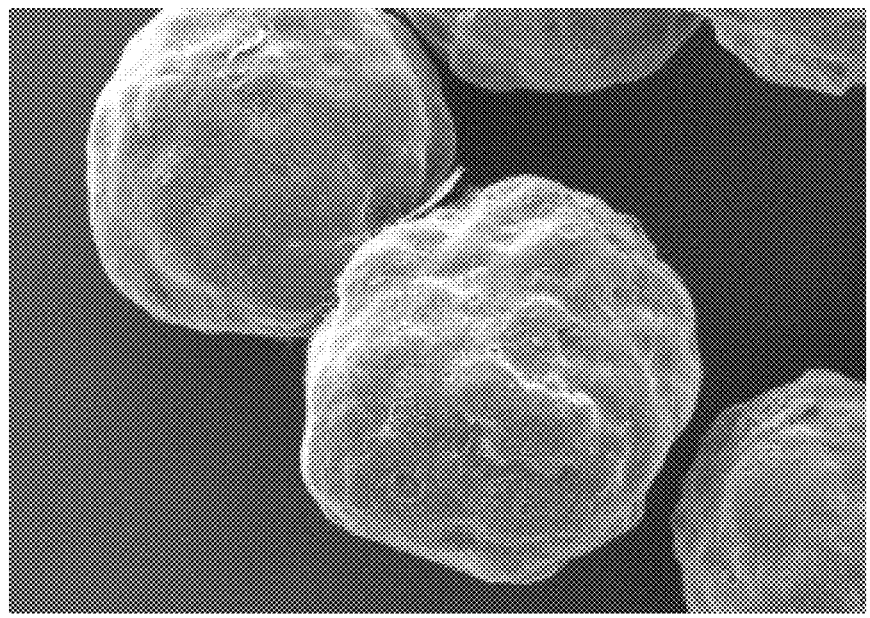
Figure 2D:
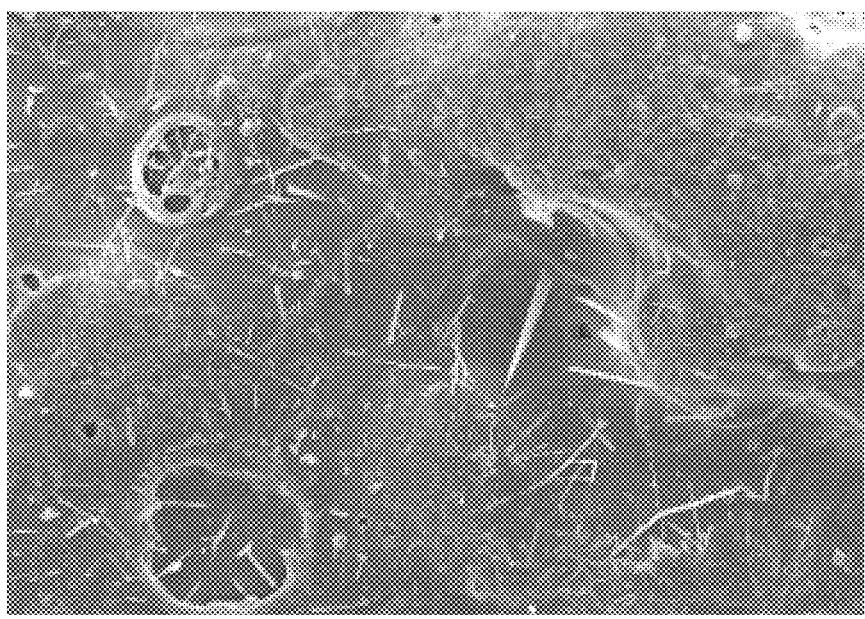
Figure 2E:
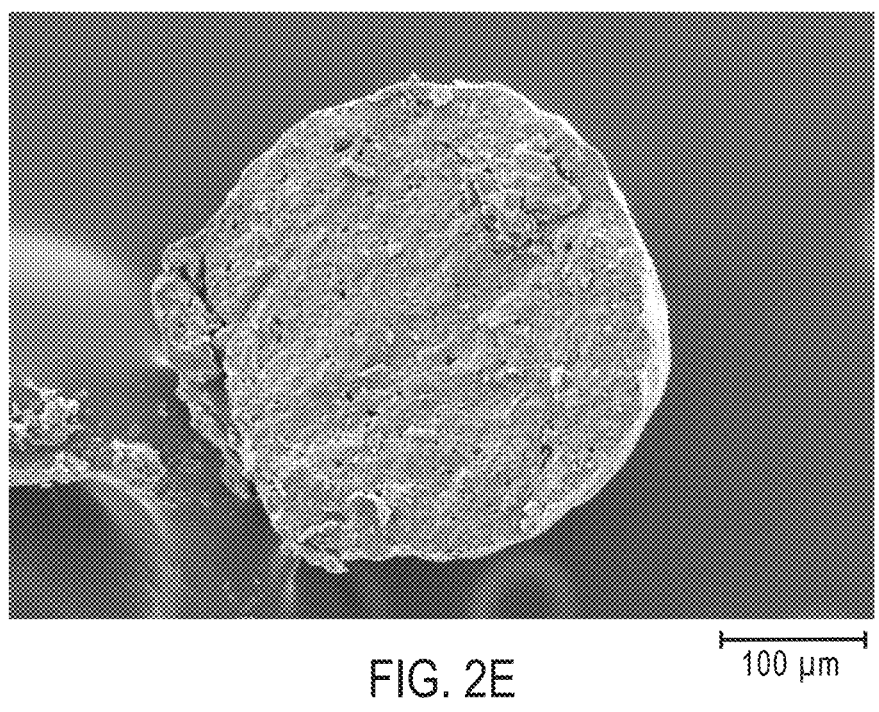

FIGS. 2A-2D show 4-((L-valyl)oxy)butanoic acid-containing granules having a 1.3 μm (+/−0.27 μm) thick seal coating of hydroxypropylmethyl cellulose and talc at various magnifications. FIG. 2E shows a cross-sectional view of a 4-((L-valyl)oxy)butanoic acid-containing granule having a seal coating of hydroxypropylmethyl cellulose and talc.

Figure 4A:
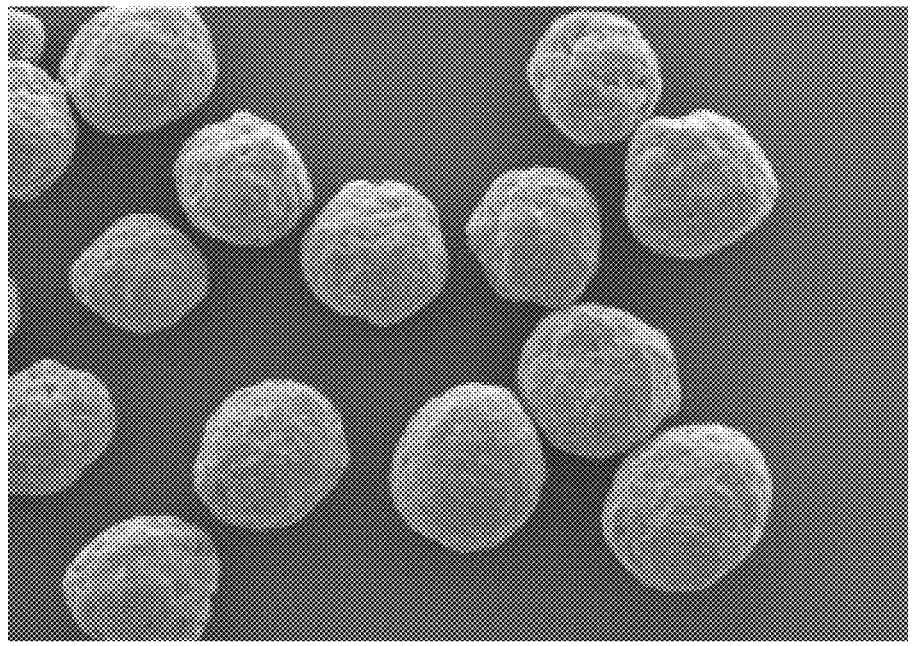
FIGS. 4A-4E show SEM images of seal-coated granules at different magnifications as described in Example 2.
Figure 4B:
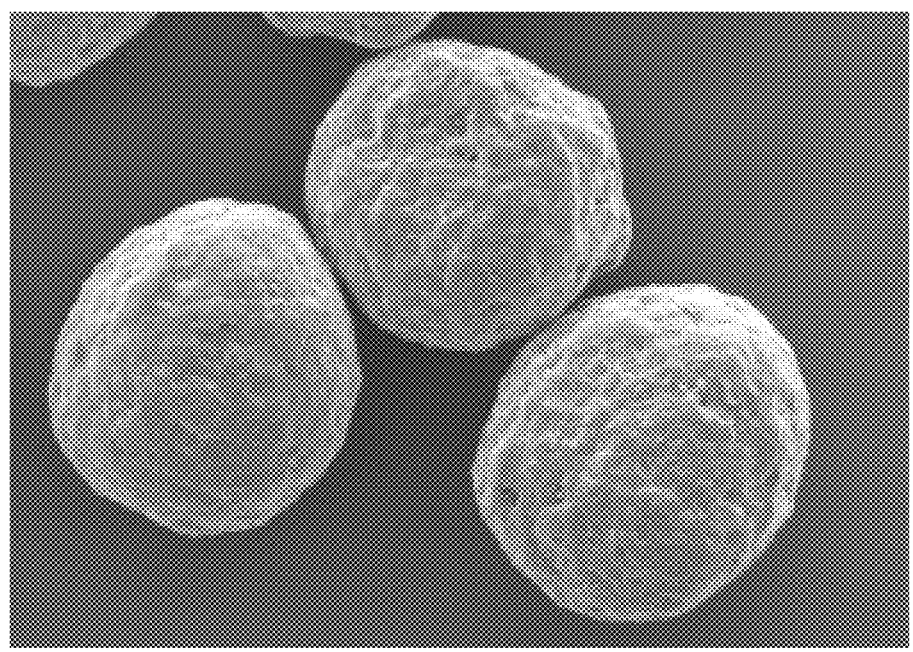
Figure 4C:
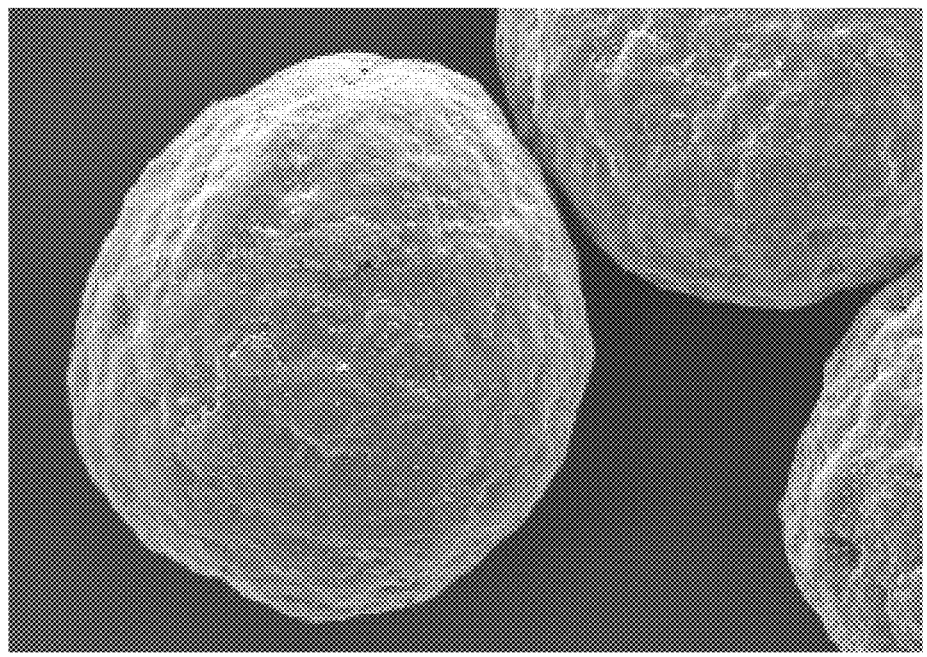
Figure 4D:
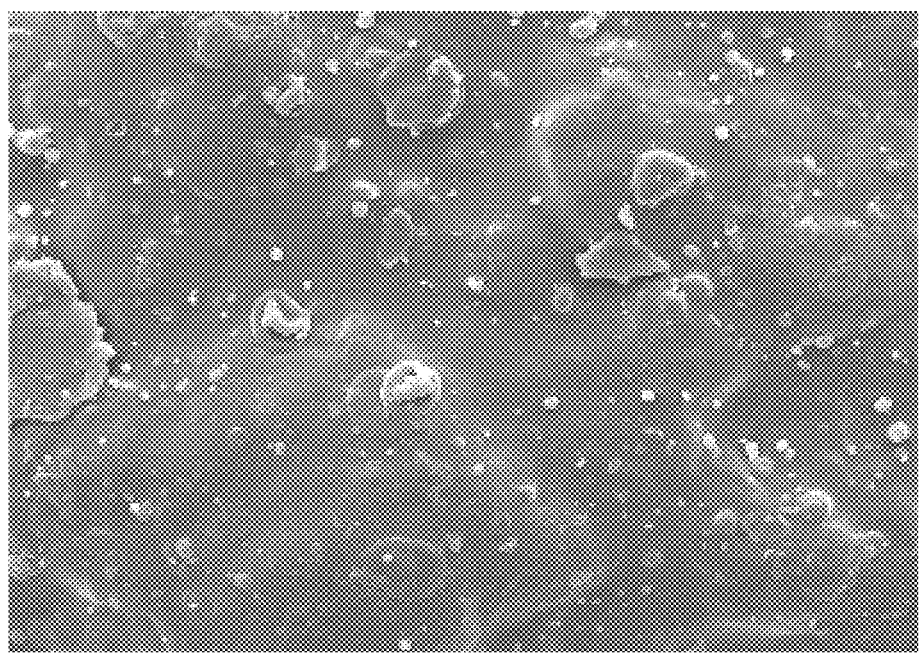
Figure 4E:
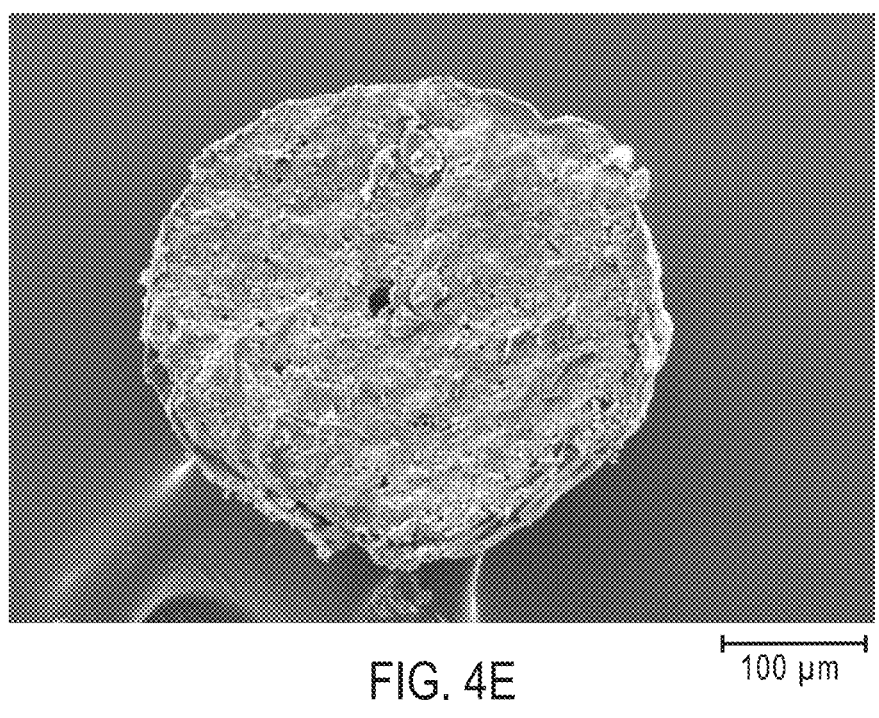

FIGS. 4A-4D show 4-((L-valyl)oxy)butanoic acid-containing granules having a 2.23 μm (+/−0.34 μm) thick seal coating of hydroxypropyl cellulose and talc at various magnifications. FIG. 4E shows a cross-sectional view of a 4-((L-valyl)oxy)butanoic acid granule having a seal coating of hydroxypropyl cellulose and talc.

Coated pharmaceutical granulations provided by the present disclosure can comprise a plurality of granules coated with a functional coating. A functional coating can comprise, for example, a modified release coating such as a controlled release coating, a sustained release coating, a pH-release coating, a pulsatile release coating, a timed-release coating, or a delayed release coating. A functional coating can be configured to release 4-((L-valyl)oxy)butanoic acid from a coated granule, for example, over an intended period of time following ingestion and/or in an intended region of the gastrointestinal tract.

A coated pharmaceutical granule provided by the present disclosure can comprise one or more functional coatings.

Each of the one or more functional coatings can independently have an average thickness, for example, of less than 50 µm, less than 40 µm, less than 30 µm, less than 20 µm, less than 15 µm, less than 10 µm, or less than 5 µm. Each of the one or more functional coatings can independently have an average thickness, for example, from 5 µm to 50 µm, from 5 µm to 40 µm, from 5 µm to 30 µm, from 5 µm to 20 µm, from 5 µm to 15 µm, or from 5 µm to 10 µm.

A coated granule or coated granulation can comprise, for example, greater than 50 wt % of 4-((L-valyl)oxy)butanoic acid, greater than 55 wt %, greater than 60 wt % greater than 70 wt %, greater than 80 wt %, or greater than 85 wt % of 4-((L-valyl)oxy)butanoic acid, where wt % is based on the total weight of the coated granule or coated granulation.

A coated granule or coated granulation comprising a plurality of coated granules can comprise, for example, from 50 wt % to 85 wt % of 4-((L-valyl)oxy)butanoic acid, from 55 wt % to 80 wt %, from 60 wt % to 80 wt %, from 65 wt % to 80 wt %, or from 70 wt % to 75 wt % of 4-((L-valyl)oxy)butanoic acid, where wt % is based on the total weight of the coated granule or coated granulation.

A coated granule or coated granulation can comprise, for example, less than 50 wt % of a functional coating, less than 40 wt % of a functional coating, less than 30 wt %, less than 20 wt %, or less than 10 wt % of a functional coating, where wt % is based on the total weight of the coated granule or coated granulation. A coated granule or coated granulation can comprise, for example, from 10 wt % to 50 wt % of a functional coating, from 10 wt % to 45 wt %, from 15 wt % to 40 wt %, or from 15 wt % to 35 wt % of a functional coating, wherein wt % is based on the total weight of the coated granulation. Coated granulations containing 4-((L-valyl)oxy)butanoic acid can have a thick coating to reduce the release rate of 4-((L-valyl)oxy)butanoic acid and/or increase the storage stability of 4-((L-valyl)oxy)butanoic acid by minimizing or preventing ingress of moisture.

A coated granule or coated granulation can comprise, for example, greater than 50 wt % of 4-((L-valyl)oxy)butanoic acid, greater than 55 wt %, greater than 60 wt %, greater than 70 wt %, greater than 80 wt %, or greater than 85 wt % of 4-((L-valyl)oxy)butanoic acid, where wt % is based on the total weight of the coated granule or coated granulation.

A coated granule or coated granulation comprising a plurality of coated granules can comprise, for example, from 50 wt % to 90 wt % of 4-((L-valyl)oxy)butanoic acid, from 55 wt % to 85 wt %, from 60 wt % to 85 wt %, from 65 wt % to 85 wt %, or from 70 wt % to 80 wt % of 4-((L-valyl)oxy)butanoic acid, where wt % is based on the total weight of the coated granule or coated granulation.

A functional coating can comprise a matrix polymer or combination of matrix polymers. A combination of a matrix polymer and/or a pore forming polymer can be selected to provide for a desired release profile of 4-((L-valyl)oxy) butanoic acid in the gastrointestinal tract.

A functional coating can comprise, for example, from 55 wt % to 95 wt % of a matrix polymer, from 60 wt % to 90 wt %, from 65 wt % to 90 wt %, from 70 wt % to 85 wt %, or from 75 wt % to 85 wt %, of a matrix polymer, where wt % is based on the total weight of the functional coating.

A functional coating can comprise a matrix polymer or combination of matrix polymers. A combination of a matrix polymer can be selected to provide for a desired release profile of 4-((L-valyl)oxy)butanoic acid in the gastrointestinal tract.

A functional coating can comprise, for example, from 55 wt % to 95 wt % of a matrix polymer, from 60 wt % to 90 wt %, from 65 wt % to 90 wt %, from 70 wt % to 85 wt %, or from 75 wt % to 85 wt %, of a matrix polymer, where wt % is based on the total weight of the functional coating.

A functional coating can comprise, for example less than 95 wt % of a matrix polymer, less than 90 wt %, less than 85 wt %, less than 80 wt %, less than 75 wt %, less than 70 wt %, or less than 60 wt % of a matrix polymer, where wt % is based on the total weight of the functional coating.

A functional coating can comprise, for example, greater than 50% of a matrix polymer, great than 55 wt %, greater than 60 wt %, greater than 65 wt %, greater than 70 wt %, greater than 75 wt %, greater than 80 wt %, greater than 85 wt %, or greater than 90 wt % of a matrix polymer, where wt % is based on the total weight of the functional coating.

A matrix polymer can comprise a water-insoluble polymer or combination of water-insoluble polymers.

Examples of suitable water insoluble polymers include ethylcellulose, polyvinyl acetates, polyacrylates, and polymethacrylates.

A water insoluble polymer such as ethylcellulose can have an average molecular weight, for example, from 25,000 Daltons to 300,000 Daltons, such as from 50,000 Daltons to 200,000 Daltons, from 50,000 Daltons to 150,000 Daltons, or from 50,000 Daltons to 100,000 Daltons.

A water insoluble polymer such as ethylcellulose can have a viscosity, for example, less than 100 mPa×sec, less than 75 mPa×sec, less than 50 mPa×sec, less than 25 mPa×sec, less than 20 mPa×sec, or less than 15 mPa×sec, as determined using a Brookfield viscometer in an 80:20 mixture of toluene/ethanol.

Examples of suitable ethylcellulose polymers include Aqualon® T10 Pharm, N7 Pharm, N10 Pharm, N14 Pharm, N22 Pharm, N50 Pharm, and N100 Pharm polymers, available from Ashland. Other examples of suitable ethylcellulose polymers include Ethocel® Standard 7, Standard 10, Standard 14, Standard 20 polymers, available from Dupont.

A matrix polymer can comprise, for example, from 90 wt % to 100 wt % of a water-insoluble polymer, from 91 wt % to 99 wt %, from 82 wt % to 98 wt %, or from 93 wt % to 97 wt % of a water-insoluble polymer, where wt % is based on the total weight of the matrix polymer. A matrix polymer can comprise, for example, greater than 90 wt % of a water insoluble polymer, greater than 92 wt %, greater than 94 wt %, greater than 96 wt %, or greater than 98 wt % of a water insoluble polymer, where wt % is based on the total weight of the matrix polymer. A matrix polymer can comprise, for example less than 100 wt % of a water insoluble polymer, less than 98 wt %, less than 96 wt %, less than 94 wt %, or less than 92 wt % of a water insoluble polymer, where wt % is based on the total weight of the matrix polymer.

A matrix polymer can comprise a pore forming polymer. Examples of pore forming polymers include water-soluble polymers, polymers that swell or expand such as carbomers, and polymers soluble in gastric fluid such as cellulose acetate phthalate, hydroxypropyl cellulose, hydroxypropylmethyl cellulose, methacrylic acid-methyl methacrylate copolymers, and polyvinyl acetate phthalate. A pore forming polymer can increase the permeability of a functional coating under intended conditions.

A matrix polymer can comprise a water-soluble polymer or combination of water-soluble polymers.

Examples of suitable water-soluble polymers include hydroxypropyl cellulose, polyvinyl alcohol, hydroxypropylmethyl cellulose, hydroxypropylethyl cellulose, polyvinylpyrrolidone, polyethylene glycol, polyvinyl alcohol, povidone, copovidone, and poloxamer.

A water-soluble polymer such as hydroxypropyl cellulose can have an average molecular weight, for example, less than 1,000,000 Daltons, less than 800,000 Daltons, less than 600,000 Daltons, less than 400,000 Daltons, less than 200,000 Daltons, less than 100,000 Daltons, or less than 50,0000 Daltons.

A water-soluble polymer such as hydroxypropyl cellulose can have a viscosity, for example, less than 7,000 mPa×sec, less than 5,000 mPa×sec, less than 3,000 mPa×sec, or less than 1,000 mPa×sec, as determined using a Brookfield viscometer in an 80:20 mixture of toluene/ethanol.

Examples of suitable hydroxypropyl cellulose polymers include Klucel® HF Pharm, MF Pharm, GF Pharm JF Pharm, LF Pharm, EF Pharm, and ELF Pharm polymers, available from Ashland.

Examples of suitable hydroxypropylmethyl cellulose polymers include Pharmacoat® 603, 645, 606 and 615 polymers, available from Shin-Etsu Chemical Co.

A matrix polymer can comprise, for example, from 0 wt % to 15 wt % of a water-soluble polymer, from 0 wt % to 10 wt %, from 1 wt % to 8 wt %, or from 2 wt % to 6 wt % of a water-soluble polymer, where wt % is based on the total weight of the matrix polymer. A matrix polymer can comprise, for example, greater than 0 wt % of a water-soluble polymer, greater than 2 wt %, greater than 4 wt %, greater than 6 wt %, or greater than 8 wt % of a water-soluble polymer, where wt % is based on the total weight of the matrix polymer. A matrix polymer can comprise, for example, less than 10 wt % of a water-soluble polymer, less than 8 wt %, less than 6 wt %, less than 4 wt %, or less than 2 wt % of a water-soluble polymer, where wt % is based on the total weight of the matrix polymer.

A matrix polymer can comprise, for example, from 90 wt % to 100 wt % of a water-insoluble polymer and from 0 wt % to 10 wt % of a water-soluble polymer, from 92 wt % to 98 wt % of a water-insoluble polymer and from 2 wt % to 8 wt % of a water-soluble polymer, or from 94 wt % to 96 wt % of a water-insoluble polymer and from 4 wt % to 6 wt % of a water-soluble polymer, where wt % is based on the total weight of the matrix polymer.

A functional coating can be applied to granules provided by the present disclosure by any suitable method such as by spraying a solution, suspension, or dispersion of the functional coating onto granules in a fluidized bed apparatus.

In addition to a matrix polymer or combination of matrix polymers, a functional coating can comprise, for example, a plasticizing agent, an anti-static, an anti-tacking agent, a colorant or pigment, a glidant, a viscosity modifier, or a combination of any of the foregoing.

A functional coating can comprise an antistatic agent or combination of antistatic agents.

An antistatic agent is useful to minimize or prevent agglomeration of the granules during application of the functional coating.

Examples of suitable antistatic agents include talc, magnesium stearate, and silicon dioxide.

A functional coating can comprise, for example, from 5 wt % to 25 wt % of an antistatic agent, such as from 8 wt % to 22 wt %, or from 10 wt % to 20 wt % of an antistatic agent, where wt % is based on the total weight of the functional coating. A functional coating can comprise, for example, less than 25 wt % of an antistatic agent, less than 23 wt %, less than 18 wt %, or less than 15 wt % of an antistatic agent, where wt % is based on the total weight of the functional coating. A functional coating can comprise, for example, greater than 5 wt % of an antistatic agent, greater than 8 wt %, greater than 12 wt %, greater than 16 wt %, or greater than 20 wt % of an antistatic agent, where wt % is based on the total weight of the functional coating.

A functional coating provided by the present disclosure does not include a plasticizer such as dibutyl sebacate, polyethylene glycol, triacetin, and triethyl citrate.

A functional coating provided by the present disclosure can comprise, for example, from 70 wt % to 95 wt % of a matrix polymer and from 5 wt % to 30 wt % of an antistatic agent, where wt % is based on the total weight of the functional coating.

A functional coating provided by the present disclosure can comprise, for example, from 75 wt % to 90 wt % of a matrix polymer and from 10 wt % to 25 wt % of an antistatic agent, where wt % is based on the total weight of the functional coating.

A functional coating provided by the present disclosure can comprise, for example, from 80 wt % to 90 wt % of a matrix polymer and from 10 wt % to 12 wt % of an antistatic agent, where wt % is based on the total weight of the functional coating.

In a functional coating provided by the present disclosure, a matrix polymer can comprise hydroxypropyl cellulose and hydroxypropylmethyl cellulose, and the antistatic agent can comprise magnesium stearate, talc, or a combination thereof.

A functional coating such as a modified release coating of the present disclosure can comprise, for example, from 72 wt % to 92 wt % of a water-insoluble polymer such as ethyl cellulose, form 0.5 wt % to 4 wt % of a water-soluble polymer such as hydroxypropylmethyl cellulose, and from 11 wt % to 22 wt % of an antistatic agent such as magnesium stearate, where wt % is based on the total weight of the functional coating. A functional coating such as a modified release coating of the present disclosure can comprise, for example, from 74 wt % to 90 wt % of a water-insoluble polymer such as ethyl cellulose, form 1 wt % to 3.5 wt % of a water-soluble polymer such as hydroxypropylmethyl cellulose, and from 13 wt % to 20 wt % of an antistatic agent such as magnesium stearate, where wt % is based on the total weight of the functional coating. A functional coating such as a modified release coating of the present disclosure can comprise, for example, from 76 wt % to 88 wt % of a water-insoluble polymer such as ethyl cellulose, form 1 wt % to 3.0 wt % of a water-soluble polymer such as hydroxypropylmethyl cellulose, and from 14 wt % to 18 wt % of an antistatic agent such as magnesium stearate, where wt % is based on the total weight of the functional coating.

A modified release granule or granulation provided by the present disclosure can comprise, for example, a core and a modified release coating surrounding the core. The core can comprise, for example, from 85 wt % to 95 wt % of 4-((L-valyl)oxy)butanoic acid, from 1 wt % to 9 wt % such as from 3 wt % to 7 wt % of a water-soluble polymer such as hydroxypropylmethyl cellulose, and from 1 wt % to 9 wt % such as from 3 wt % to 7 wt % of an antistatic agent such as magnesium stearate, where wt % is based on the total weight of the core; and the modified release coating surrounding the core can comprise, for example, from 77 wt % to 87 wt % of a water insoluble polymer such as ethylcellulose, from 0.1 wwt % to 5 wt % of a water-soluble polymer such as hydroxypropylmethyl cellulose, and from 11 wt % to 21 wt % such as from 14 wt % to 18 wt % of an antistatic agent such as magnesium stearate, where wt % is based on the total weight of the modified release coating.

A modified release granulation provided by the present disclosure can be configured to provide for once a night dosing, once a day dosing (QD), twice a day dosing (BID), three times a day dosing (TID), or four times a day dosing (QID). For example, a modified release granulation can release substantially 100% of the 4-((L-valyl)oxy)butanoic acid over a 24-hour duration, a 12-hour duration, an 8-hour duration, or a 4-hour duration.

For example, a modified release granulation can exhibit a dissolution profile as substantially shown, for example, in FIGS. 6, 9, 12, and 16. For example, a modified release granulation can exhibit a dissolution profile that is bioequivalent to any of the dissolution profiles shown, for example, in FIGS. 6, 9, 12, and 16.

A modified release granulation can exhibit a dissolution profile, for example, in which less than 80% of the 4-((L-valyl)oxy)butanoic acid is released from the modified release granulation within 2 hours, less than 70 wt %, less than 60 wt %, less than 50 wt %, or less than 40 wt % of the 4-((L-valyl)oxy)butanoic acid is released from the modified release granulation within 2 hours; and greater than 60 wt %, greater than 70 wt %, or greater than 80 wt % of the 4-((L-valyl)oxy)butanoic acid is released from the modified release granulation within 6 hours as determined using a USP Type 2 dissolution apparatus in a buffered solution at pH 4.5 at a temperature of 37° C. and a paddle speed of 100 rpm, where wt % is based on the total weight of the 4-((L-valyl)oxy)butanoic acid in the granulation.

A modified release granulation can exhibit a dissolution profile in which from 30 wt % to 80 wt %, such as from 35 wt % to 75 wt %, or from 40 wt % to 70 wt % of the 4-((L-valyl)oxy)butanoic acid is released from the modified release granulation within 2 hours as determined using a USP Type 2 dissolution apparatus in a buffered solution at pH 4.5 at a temperature of 37° C. and a paddle speed of 100 rpm, where wt % is based on the total weight of the 4-((L-valyl)oxy)butanoic acid in the granulation.

A modified release granulation can exhibit a dissolution profile in which from 50 wt % to 90 wt %, such as from 65 wt % to 85 wt %, or from 70 wt % to 80 wt % of the 4-((L-valyl)oxy)butanoic acid is released from the modified release granulation within 4 hours as determined using a USP Type 2 dissolution apparatus in a buffered solution at pH 4.5 at a temperature of 37° C. and a paddle speed of 100 rpm, where wt % is based on the total weight of the 4-((L-valyl)oxy)butanoic acid in the granulation.

A modified release granulation can exhibit a dissolution profile in which from 60 wt % to 100 wt %, such as from 65 wt % to 95 wt % or from 70 wt % to 90 wt %, of the 4-((L-valyl)oxy)butanoic acid is released from the modified release granulation within 6 hours as determined using a USP Type 2 dissolution apparatus in a buffered solution at pH 4.5 at a temperature of 37° C. and a paddle speed of 100 rpm, where wt % is based on the total weight of the 4-((L-valyl)oxy)butanoic acid in the granulation.

A modified release granulation can exhibit a dissolution profile in which from 30% to 80% of the 4-((L-valyl)oxy) butanoic acid is released from the modified release granulation within 2 hours, from 50 wt % to 90 wt % of the 4-((L-valyl)oxy)butanoic acid is released from the modified release granulation within 4 hours, and from 60 wt % to 100 wt % of the 4-((L-valyl)oxy)butanoic acid is released from the composition within 6 hours, as determined using a USP Type 2 dissolution apparatus in a buffered solution at pH 4.5 at a temperature of 37° C. and a paddle speed of 100 rpm, where wt % is based on the total weight of the 4-((L-valyl)oxy)butanoic acid in the granulation.

A modified release granulation can exhibit a dissolution profile in which from 25 wt % to 70 wt % of the 4-((L-valyl)oxy)butanoic acid is released from the modified release granulation within 2 hours, from 50 wt % to 85 wt % of the 4-((L-valyl)oxy)butanoic acid is released from the modified release granulation within 4 hours, and from 60 wt % to 85 wt % of the 4-((L-valyl)oxy)butanoic acid is released from the modified release granulation within 6 hours, as determined using a USP Type 2 dissolution apparatus in a buffered solution at pH 4.5 at a temperature of 37° C. and a paddle speed of 100 rpm, where wt % is based on the total weight of the 4-((L-valyl)oxy)butanoic acid in the granulation.

Figure 9:
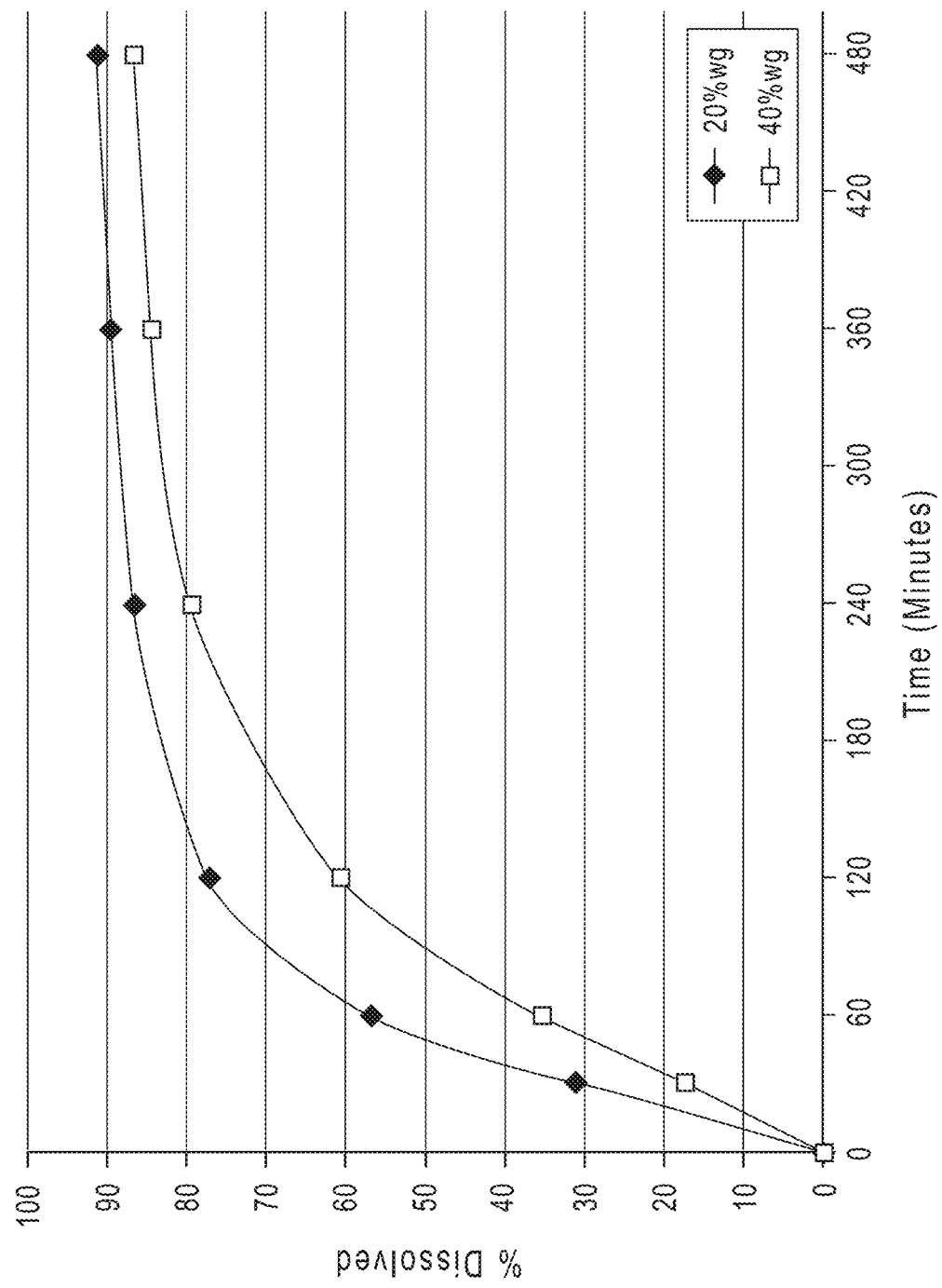
FIG. 9 shows dissolution profiles of 4-((L-valyl)oxy) butanoic acid from granules containing an ethylcellulose/ hydroxypropyl cellulose functional coating representing different % wg as described in Example 4.
Figure 12:
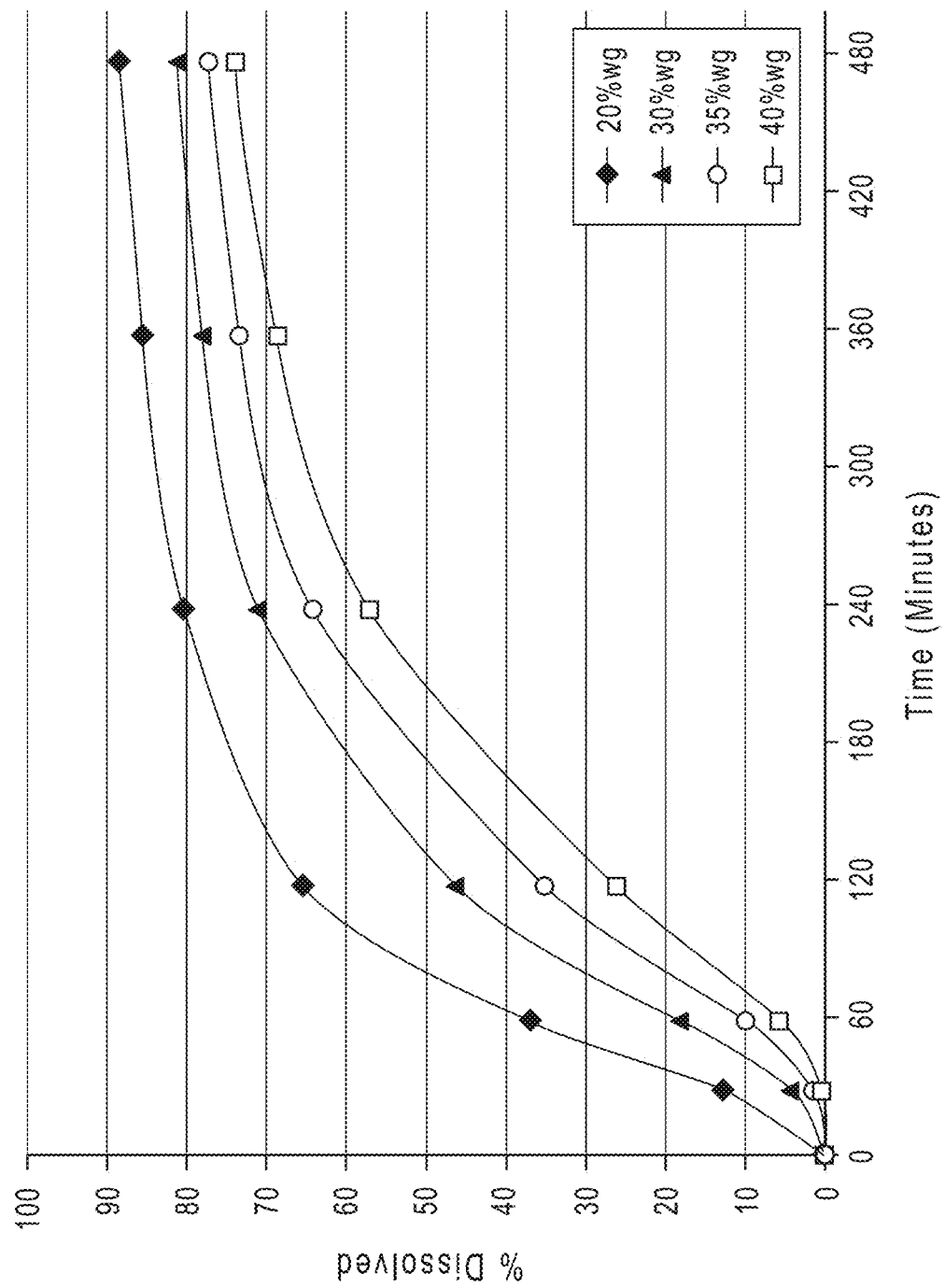
FIG. 12 shows dissolution profiles of 4-((L-valyl)oxy) butanoic acid from granules containing an ethylcellulose/hydroxypropylcellulose functional coating representing different % wg as described in Example 5.

A modified release granulation can exhibit a dissolution profile that is bioequivalent to any of the dissolution profiles shown in FIGS. 9 and 12.

A coated granulation provided by the present disclosure can have a water content, for example, less than 2 wt %, less than 1.5 wt % less than 1 wt %, less than 0.5 wt % or less than 0.25 wt %, where wt % is based on the total weight of the coated granulation.

A coated granulation provided by the present disclosure can have a water content, for example, from 0.1 wt % to 2 wt %, from 0.1 wt % to 1 wt %, or from 0.2 wt % to 0.6 wt %, where wt % is based on the total weight of the coated granulation.

A coated pharmaceutical granulation can have a bulk density, for example, greater than 0.55 g/mL, greater than 0.60 g/mL, greater than 0.65 g/mL, greater than 0.70 g/mL, or greater than 0.75 g/mL.

A coated pharmaceutical granulation can have a bulk density, for example, from 0.55 g/mL to 0.80 g/mL, from 0.60 g/mL to 75 g/mL, from 0.60 g/mL to 0.70 g/mL.

Bulk density can be determined using a bulk density cylinder.

A coated pharmaceutical granulation provided by the present disclosure can be characterized by a PSD (D50), for example, from 150 μm to 400 μm, such as from 150 μm to 350 μm, from 175 μm to 325 μm, from 200 μm to 300 μm, from 250 μm to 350 μm, or from 225 μm to 275 μm.

Examples of particle size distributions for coated granulations provided by the present disclosure are shown in FIGS. 5, 8, 11, and 15.

A particle size distribution can be determined by laser diffraction or by sieve analysis.

Functional coatings provided by the present disclosure can be coated onto granulations using any suitable equipment and process. Examples of suitable coating methods include Wurster fluid bed film coating processes, compression coating processes, and phase inversion processes.

A functional coating can be applied to an uncoated granulation or to a granulation comprising a seal coating provided by the present disclosure.

Examples of coating compositions are provided in the experimental examples. A coating composition refers to the composition that is applied to an uncoated granulation or a seal-coated granulation comprising to provide a coated granulation.

A functional coating composition can comprise greater than 70 wt %, greater than 75 wt %, greater than 80 wt %, greater than 85 wt %, or greater than 90 wt % of a non-aqueous solvent such as ethanol or acetone, where wt % is based on the total weight of the functional coating solution/suspension composition used to coat the granulation.

A functional coating composition can comprise, for example, less than 20 wt % water, less than 15 wt %, less than 10 wt %, or less than 5 wt % water, where wt % is based on the functional coating solution/suspension composition used to coat the granulation.

For highly water-soluble and hygroscopic pharmaceutically active ingredients such as 4-((L-valyl)oxy)butanoic acid, it can be useful to minimize the amount of water in the functional coating composition. Reducing the level of water in the functional coating solution/suspension composition can lead to static that can render the coating process problematic.

A functional coating solution/suspension composition can comprise, for example, a solids content less than 20 wt %, less than 18 wt %, less than 16 wt %, less than 14 wt %, less than 12 wt %, less than 10 wt %, less than 8 wt %, or less than 6 wt %, where wt % is based on the functional coating solution/suspension composition.

A functional coating composition can comprise a solids content, for example, from 2 wt % to 20 wt %, from 4 wt % to 16 wt %, from 4 wt % to 12 wt %, from 6 w % to 14 wt %, or from 6 wt % to 10 wt %, where wt % is based on the functional coating composition.

Examples of coating process conditions using a Wurster column inserted into a fluid bed coating equipment are provided in the experimental examples.

A granulation provided by the present disclosure can comprise an immediate release granulation.

An immediate release granulation can comprise a plurality of uncoated granules or a plurality of granules comprising a seal coating.

An immediate release granulation comprising a plurality of uncoated or seal-coated granules can comprise greater than 90 wt % of 4-((L-valyl)oxy)butanoic acid provided by the present disclosure such as 4-((L-valyl)oxy)butanoic acid. An immediate release granulation comprising uncoated or seal-coated granules can dissolve completely, for example, in less than 10 minutes, less than 8 minutes, less than 6 minutes, less than 5 minutes, or less than 4 minutes, when tested in a USP Type 2 dissolution apparatus in a buffered solution at pH 4.5 at a temperature of 37° C. and a paddle speed of 100 rpm.

An immediate release granulation can comprise a plurality of coated or seal-coated granules having an immediate release functional coating. An immediate release granulation comprising a plurality of coated granules can comprise greater than 80 wt % of 4-((L-valyl)oxy)butanoic acid. An immediate release granulation comprising coated granules can dissolve completely, for example, in less than 25 minutes, less than 20 minutes, less than 18 minutes, less than 16 minutes, less than 14 minutes, or less than 12 minutes, when tested in a USP Type 2 dissolution apparatus in a buffered solution at pH 4.5 at a temperature of 37° C. and a paddle speed of 100 rpm. An immediate release granulation comprising coated granules can release greater than 80% of 4-((L-valyl)oxy)butanoic acid, for example, in less than 10 minutes, less than 8 minutes, less than 6 minutes, or less than 4 minutes, when tested in a USP Type 2 dissolution apparatus in a buffered solution at pH 4.5 at a temperature of 37° C. and a paddle speed of 100 rpm. A coated immediate release granulation can comprise a coating comprising a water-soluble polymer such as, for example, hydroxypropylcellulose, polyvinyl alcohol, hydroxypropylmethyl cellulose, hydroxypropylethyl cellulose, polyvinylpyrrolidone, or polyethylene glycol. A coated immediate release granulation can comprise a coating comprising an antistatic agent such as talc, magnesium stearate, or silicon dioxide.

A pharmaceutical composition provided by the present disclosure can comprise a combination of an immediate release granulation and a modified release granulation. A pharmaceutical composition can comprise a wt % ratio of 4-((L-valyl)oxy)butanoic acid) as an immediate release granulation to 4-((L-valyl)oxy)butanoic acid as a modified release granulation, for example, from 1:1 to 1:4, from 1:1 to 1:3, from 1:1 to 1:2 or from 1:2 to 1:3.

A pharmaceutical composition provided by the present disclosure can comprise a coated granulation provided by the present disclosure.

A pharmaceutical composition can comprise any suitable dosage form for oral administration.

Examples of suitable oral dosage forms include tablets, capsules, caplets, sachets, bottles, stick packs, dispersions, and suspensions.

An oral dosage form provided by the present disclosure can comprise, for example, from 0.1 grams to 20 grams of 4-((L-valyl)oxy)butanoic acid, from 0.1 grams to 15 grams, from 0.1 grams to 12 grams, from 0.1 grams to 10 grams, from 0.2 grams to 8 grams, from 0.5 grams to 5 grams, from 1 gram to 4.5 grams, or from 1.5 grams to 4 grams of 4-((L-valyl)oxy)butanoic acid. An oral dosage form can comprise, for example, greater than 0.5 grams, greater than 1 gram, greater than 2 grams, greater than 3 grams, greater than 4 grams, greater than 6 grams, or greater than 8 grams greater than 10 grams, greater than 14 grams, or greater than 18 grams of 4-((L-valyl)oxy)butanoic acid.

An oral composition provided by the present disclosure can comprise an oral suspension of coated granules having a modified release functional coating provided by the present disclosure. An oral composition can comprise a modified release granulation provided by the present disclosure and an immediate release granulation.

An oral composition can comprise a combination of an immediate release granulation and a modified release granulation provided by the present disclosure.

An oral composition provided by the present disclosure can provide a therapeutically effective amount of 4-((L-valyl)oxy)butanoic acid over a period of time.

For example, an oral composition provided by the present disclosure can provide a therapeutically effective amount of 4-((L-valyl)oxy)butanoic acid over a period of 3 hours, 6, hours 8, hours, or 10 hours.

An oral composition provided by the present disclosure can provide a therapeutically effective amount of 4-((L-valyl)oxy)butanoic acid over a period from 4 hours to 12 hours, from 4 hours to 10 hours, or from 4 hours to 8 hours.

An oral composition provided by the present disclosure can provide a therapeutically effective amount of 4-((L-valyl)oxy)butanoic acid over a duration from 1 hour to 12 hours following oral administration, from 2 hours to 10 hours, or from 4 hours to 8 hours following oral administration.

An oral composition provided by the present disclosure can be a once nightly composition. For a once nightly composition, a patient can administer a dose of 4-((L-valyl)oxy)butanoic acid before going to bed and sleep through the night such as for 6 hours or for 8 hours without having to administer a second dose during the night.

An oral composition provided by the present disclosure can provide a therapeutically effective amount of a γ-hydroxybutyric acid in the plasma of a patient.

An oral composition provided by the present disclosure can provide a therapeutically effective amount of γ-hydroxybutyric acid in the plasma of a patient for a period of 4 hours, 6, hours, 8 hours, or 10 hours following oral administration of the modified release oral composition.

An oral composition provided by the present disclosure can provide a plasma concentration of γ-hydroxybutyric acid greater than 10 μg/mL for more than 4 hours, more than 6 hours, more than 8 hours, or more than 10 hours following oral administration of the modified release oral composition.

An oral composition provided by the present disclosure can provide a plasma concentration of γ-hydroxybutyric acid greater than 15 μg/mL for more than 4 hours, more than 6 hours, more than 8 hours, or more than 10 hours following oral administration of the modified release oral composition.

An oral composition provided by the present disclosure can provide a therapeutically effective amount of $C_{max}$ to $C_{min}$ ratio of γ-hydroxybutyric acid in the plasma of a patient from less than 3 or less than 2 for a duration of 4 hours, 6 hours, 8 hours, or 10 hours following oral administration of the modified release oral composition.

An oral composition provided by the present disclosure can comprise a γ-hydroxybutyric acid derivative of Formula (2) and can comprise, for example, 0.5 g-equivalents γ-hydroxybutyric acid, 1 g-equivalents, 2 g-equivalents, 3 g-equivalents, 4 g-equivalents, 5 g-equivalents, 6 g-equivalents, 7 g-equivalents, 8 g-equivalents, 9 g-equivalents, 10 g-equivalents, 11 g-equivalents, or 12 g-equivalents γ-hydroxybutyric acid.

A pharmaceutical composition provided by the present disclosure can be included in a kit that may be used to administer the compound to a patient for therapeutic purposes. A kit can include a pharmaceutical composition comprising an immediate release component and a modified release component suitable for administration to a patient and instructions for administering the pharmaceutical composition to the patient. The kit can be used, for example, to treat a sleep disorder. A kit can comprise an immediate release component and a modified release component, a pharmaceutically acceptable vehicle for administering the immediate release component and a modified release component, and instructions for administering the pharmaceutical composition to a patient.

Oral compositions provided by the present disclosure can be provided, for example, as sachets containing a coated granulation provided the present disclosure. A sachet can be provided in different doses of 4-((L-valyl)oxy)butanoic acid such as 0.5 g, 1 g, 2 g, 3 g, 4 g, 5 g, 6 g, 7 g, 8 g, 9 g, 10 g, 11 g, 10 g, 12 g, 15 g, or 20 g of 4-((L-valyl)oxy)butanoic acid. The coated granulation can be combined, for example, with water to provide an orally ingestible dosage form.

The pharmaceutical compositions can be included in a container, pack, or dispenser together with instructions for administration.

Instructions supplied with a kit may be printed and/or supplied, for example, as an electronic-readable medium, a video cassette, an audiotape, a flash memory device, or may be published on an internet web site or distributed to a patient and/or health care provider as an electronic communication.

Following oral administration of an IR composition comprising 7.25 g compound (1) to a population of fasted, healthy subjects a plasma pharmacokinetic profile of compound (1) can be characterized by a mean $t_{1/2}$ of 0.4 hours, a mean $T_{max}$ of 0.9 hours, a mean $C_{max}$ of 16 μg/mL, a mean $AUC_{0-6}$ of 16 h×μg/mL, an $AUC_{0-inf}$ of 16 h×μg/mL, and a CL/F of 48 L/h).

Following oral administration of an IR composition comprising 7.25 g compound (1) to a population of fasted, healthy subjects a plasma pharmacokinetic profile of compound (1) can be characterized by a mean $t_{1/2}$ of from 0.3 hours to 0.5 hours, a mean $T_{max}$ from 0.8 hours to 1.0 hours, a mean $C_{max}$ from 14 μg/mL to 18 μg/mL, a mean $AUC_{0-6}$ from 14 h×μg/mL to 18 h×μg/mL, an $AUC_{0-inf}$ from 14 h×μg/mL to 18 h×μg/mL, and a CL/F of 44 L/h to 52 L/h.

Following oral administration of an IR composition comprising 7.25 g compound (1) to a population of fasted, healthy subjects a plasma pharmacokinetic profile of compound (1) can be characterized by a mean $t_{1/2}$ of from 0.35 hours to 0.45 hours, a mean $T_{max}$ from 0.85 hours to 0.95 hours, a mean $C_{max}$ from 15 μg/mL to 17 μg/mL, a mean $AUC_{0-6}$ from 15 h×μg/mL to 17 h×μg/mL, an $AUC_{0-inf}$ from 15 h×μg/mL to 17 h×μg/mL, and a CL/F of 446 L/h to 50 L/h.

Following oral administration of an MR1 composition comprising 7.25 g compound (1) to a population of fasted, healthy subjects a plasma pharmacokinetic profile of compound (1) can be characterized by a mean $t_{1/2}$ of 0.7 hours, a mean $T_{max}$ of 1.6 hours, a mean $C_{max}$ of 4 μg/mL, a mean $AUC_{0-6}$ of 9 h×μg/mL, a mean $AUC_{0-inf}$ of 9 h×μg/mL, and a mean CL/F of 838 L/h.

Following oral administration of an MR1 composition comprising 7.25 g compound (1) to a population of fasted, healthy subjects a plasma pharmacokinetic profile of compound (1) can be characterized by a mean $t_{1/2}$ from 0.5 hours to 9 hours, a mean $T_{max}$ from 1.4 hours to 1.8 hours, a mean $C_{max}$ from 2 μg/mL to 6 μg/mL, a mean $AUC_{0-6}$ from 7 h×μg/mL to 11 h×μg/mL, a mean $AUC_{0-inf}$ from 7 h×μg/mL to 11 h×μg/mL, and a mean CL/F from 818 L/h to 858 L/h.

Following oral administration of an MR1 composition comprising 7.25 g compound (1) to a population of fasted, healthy subjects a plasma pharmacokinetic profile of compound (1) can be characterized by a mean $t_{1/2}$ from 0.6 hours to 0.8 hours, a mean $T_{max}$ from 1.5 hours to 1.7 hours, a mean $C_{max}$ from 3 μg/mL to 5 μg/mL, a mean $AUC_{0-6}$ from 8 h×μg/mL to 10 h×μg/mL, a mean $AUC_{0-inf}$ from 8 h×μg/mL to 10 h×μg/mL, and a mean CL/F from 828 L/h to 848 L/h.

Following oral administration of an MR2 composition comprising 7.25 g compound (1) to a population of fasted, healthy subjects a plasma pharmacokinetic profile of compound (1) can be characterized by a mean $t_{1/2}$ of 0.7 hours, a mean $T_{max}$ of 1.4 hours, a mean $C_{max}$ of 6 μg/mL, a mean $AUC_{0-6}$ of 10 h×μg/mL, a mean $AUC_{0-inf}$ of 10 h×μg/mL, and a mean CL/F of 762 L/h.

Following oral administration of an MR2 composition comprising 7.25 g compound (1) to a population of fasted, healthy subjects a plasma pharmacokinetic profile of compound (1) can be characterized by a mean $t_{1/2}$ from 0.5 hours to 0.9 hours, a mean $T_{max}$ from 1.2 hours to 1.6 hours, a mean $C_{max}$ from 4 μg/mL to 8 μg/mL, a mean $AUC_{0-6}$ from 8 h×μg/mL to 12 h×μg/mL, a mean $AUC_{0-inf}$ from 8 h×μg/mL to 12 h×μg/mL, and a mean CL/F from 720 L/h to 800 L/h.

Following oral administration of an MR2 composition comprising 7.25 g compound (1) to a population of fasted, healthy subjects a plasma pharmacokinetic profile of compound (1) can be characterized by a mean $t_{1/2}$ from 0.4 hours to 0.8 hours, a mean $T_{max}$ from 1.3 hours to 1.5 hours, a mean $C_{max}$ from 5 µg/mL to 7 µg/mL, a mean $AUC_{0-6}$ from 9 h×µg/mL to 11 h×µg/mL, a mean $AUC_{0-inf}$ from 9 h×µg/mL to 11 h×µg/mL, and a mean CL/F from 740 L/h to 780 L/h.

Following oral administration of an MR3 composition comprising 7.25 g compound (1) to a population of fasted, healthy subjects a plasma pharmacokinetic profile of compound (1) can be characterized by a mean $t_{1/2}$ of 0.8 hours, a mean $T_{max}$ of 1.1 hours, a mean $C_{max}$ of 5 µg/mL, a mean $AUC_{0-6}$ of 10 h×µg/mL, a mean $AUC_{0-inf}$ of 10 h×µg/mL, and a mean CL/F of 801 L/h.

Following oral administration of an MR3 composition comprising 7.25 g compound (1) to a population of fasted, healthy subjects a plasma pharmacokinetic profile of compound (1) can be characterized by a mean $t_{1/2}$ from 0.6 hours to 1.0 hours, a mean $T_{max}$ from 0.9 hours to 1.3 hours, a mean $C_{max}$ from 3 µg/mL to 7 µg/mL, a mean $AUC_{0-6}$ from 8 h×µg/mL to 12 h×µg/mL, a mean $AUC_{0-inf}$ from 8 h×µg/mL to 12 h×µg/mL, and a mean CL/F from 760 L/h to 840 L/h.

Following oral administration of an MR3 composition comprising 7.25 g compound (1) to a population of fasted, healthy subjects a plasma pharmacokinetic profile of compound (1) can be characterized by a mean $t_{1/2}$ from 0.7 hours to 0.9 hours, a mean $T_{max}$ from 1.0 hours to 1.2 hours, a mean $C_{max}$ from 4 µg/mL to 6 µg/mL, a mean $AUC_{0-6}$ from 9 h×µg/mL to 11 h×µg/mL, a mean $AUC_{0-inf}$ from 9 h×µg/mL to 11 h×µg/mL, and a mean CL/F from 780 L/h to 820 L/h.

Following oral administration of an IR composition comprising 7.25 g compound (1) to a population of fasted, healthy subjects a plasma pharmacokinetic profile of γ-hydroxybutyrate can be characterized by a mean $t_{1/2}$ of 0.6 hours, a mean $T_{max}$ of 1.3 hours, a mean $C_{max}$ of 86 µg/mL, a mean $AUC_{0-6}$ of 239 h×µg/mL, a mean $AUC_{0-inf}$ of 246 h×µg/mL, and a mean CL/F of 31 L/h.

Following oral administration of an IR composition comprising 7.25 g compound (1) to a population of fasted, healthy subjects a plasma pharmacokinetic profile of γ-hydroxybutyrate can be characterized by a mean $t_{1/2}$ from 0.4 hours to 0.8 hours, a mean $T_{max}$ from 1.1 hours to 1.5 hours, a mean $C_{max}$ from 76 µg/mL to 96 µg/mL, a mean $AUC_{0-6}$ from 219 h×µg/mL to 259 h×µg/mL, a mean $AUC_{0-inf}$ from 226 h×µg/mL to 266 h×µg/mL, and a mean CL/F from 21 L/h to 41 L/h.

Following oral administration of an IR composition comprising 7.25 g compound (1) to a population of fasted, healthy subjects a plasma pharmacokinetic profile of γ-hydroxybutyrate can be characterized by a mean $t_{1/2}$ from 0.5 hours to 0.7 hours, a mean $T_{max}$ from 1.2 hours to 1.4 hours, a mean $C_{max}$ from 81 µg/mL to 91 µg/mL, a mean $AUC_{0-6}$ from 229 h×µg/mL to 249 h×µg/mL, a mean $AUC_{0-inf}$ from 236 h×µg/mL to 256 h×µg/mL, and a mean CL/F from 26 L/h to 36 L/h.

Following oral administration of an MR1 composition comprising 7.25 g compound (1) to a population of fasted, healthy subjects a plasma pharmacokinetic profile of γ-hydroxybutyrate can be characterized by a mean $t_{1/2}$ of 1.1 hours, a mean $T_{max}$ of 2.4 hours, a mean $C_{max}$ of 27 µg/mL, a mean $AUC_{0-6}$ of 86 h×µg/mL, a mean $AUC_{0-inf}$ of 95 h×µg/mL, and a mean CL/F of 95 L/h.

Following oral administration of an MR1 composition comprising 7.25 g compound (1) to a population of fasted, healthy subjects a plasma pharmacokinetic profile of γ-hydroxybutyrate can be characterized by a mean $t_{1/2}$ from 0.9 hours to 1.3 hours, a mean $T_{max}$ from 2.2 hours to 2.6 hours, a mean $C_{max}$ from 17 µg/mL to 37 µg/mL, a mean $AUC_{0-6}$ from 76 h×µg/mL to 96 h×µg/mL, a mean $AUC_{0-inf}$ from 75 h×µg/mL to 115 h×µg/mL, and a mean CL/F from 85 L/h to 105 L/h.

Following oral administration of an MR1 composition comprising 7.25 g compound (1) to a population of fasted, healthy subjects a plasma pharmacokinetic profile of γ-hydroxybutyrate can be characterized by a mean $t_{1/2}$ from 1.0 hours to 1.2 hours, a mean $T_{max}$ from 2.3 hours to 2.5 hours, a mean $C_{max}$ from 22 µg/mL to 32 µg/mL, a mean $AUC_{0-6}$ from 81 h×µg/mL to 91 h×µg/mL, a mean $AUC_{0-inf}$ from 85 h×µg/mL to 105 h×µg/mL, and a mean CL/F from 90 L/h to 100 L/h.

Following oral administration of an MR2 composition comprising 7.25 g compound (1) to a population of fasted, healthy subjects a plasma pharmacokinetic profile of γ-hydroxybutyrate can be characterized by a mean $t_{1/2}$ of 0.9 hour, a mean $T_{max}$ of 2.4 hours, a mean $C_{max}$ of 36 µg/mL, a mean $AUC_{0-6}$ of 112 h×µg/mL, a mean $AUC_{0-inf}$ of 120 h×µg/mL, and a mean CL/F of 72 L/h.

Following oral administration of an MR2 composition comprising 7.25 g compound (1) to a population of fasted, healthy subjects a plasma pharmacokinetic profile of γ-hydroxybutyrate can be characterized by a mean $t_{1/2}$ from 0.8 hours to 1.0 hour, a mean $T_{max}$ from 2.2 hours to 2.6 hours, a mean $C_{max}$ from 34 µg/mL to 38 µg/mL, a mean $AUC_{0-6}$ from 102 h×µg/mL to 122 h×µg/mL, a mean $AUC_{0-inf}$ from 110 h×µg/mL to 130 h×µg/mL, and a mean CL/F from 62 L/h to 82 L/h.

Following oral administration of an MR2 composition comprising 7.25 g compound (1) to a population of fasted, healthy subjects a plasma pharmacokinetic profile of γ-hydroxybutyrate can be characterized by a mean $t_{1/2}$ from 0.85 hours to 0.95 hour, a mean $T_{max}$ from 2.3 hours to 2.5 hours, a mean $C_{max}$ from 35 µg/mL to 37 µg/mL, a mean $AUC_{0-6}$ from 107 h×µg/mL to 117 h×µg/mL, a mean $AUC_{0-inf}$ from 125 h×µg/mL to 135 h×µg/mL, and a mean CL/F from 67 L/h to 77 L/h.

Following oral administration of an MR3 composition comprising 7.25 g compound (1) to a population of fasted, healthy subjects a plasma pharmacokinetic profile of γ-hydroxybutyrate can be characterized by a mean $t_{1/2}$ of 1.0 hours, a mean $T_{max}$ of 1.9 hours, a mean $C_{max}$ of 30 µg/mL, a mean $AUC_{0-6}$ of 102 h×µg/mL, a mean $AUC_{0-inf}$ of 110 h×µg/mL, and a mean CL/F of 79 L/h.

Following oral administration of an MR3 composition comprising 7.25 g compound (1) to a population of fasted, healthy subjects a plasma pharmacokinetic profile of γ-hydroxybutyrate can be characterized by a mean $t_{1/2}$ from 0.9 hours to 1.1 hours, a mean $T_{max}$ from 1.7 hours to 2.1 hours, a mean $C_{max}$ from 26 µg/mL to 34 µg/mL, a mean $AUC_{0-6}$ from 82 h×µg/mL to 122 h×µg/mL, a mean $AUC_{0-inf}$ from 90 h×µg/mL to 130 h×µg/mL, and a mean CL/F from 69 L/h to 89 L/h.

Following oral administration of an MR3 composition comprising 7.25 g compound (1) to a population of fasted, healthy subjects a plasma pharmacokinetic profile of γ-hydroxybutyrate can be characterized by a mean $t_{1/2}$ from 0.95 hours to 1.05 hours, a mean $T_{max}$ from 1.8 hours to 2.0 hours, a mean $C_{max}$ from 28 µg/mL to 32 µg/mL, a mean $AUC_{0-6}$ from 92 h×μg/mL to 112 h×μg/mL, a mean $AUC_{0-inf}$ from 100 h×μg/mL to 120 h×μg/mL, and a mean CL/F from 74 L/h to 84 L/h.

Following oral administration of an IR composition comprising 7.25 g compound (1) to a population of fasted, healthy subjects a plasma pharmacokinetic profile is characterized by a mean $C_{max}$ ratio of 5.9, a mean $AUC_{0-inf}$ ratio of 15.0, and a mean $AUC_{0-6}$ ratio of 16.2, where the ratio refers to the ratio of the γ-hydroxybutyrate value to the compound (1) value. Following oral administration of an IR composition comprising 7.25 g compound (1) to a population of fasted, healthy subjects a plasma pharmacokinetic profile can be characterized by a mean $C_{max}$ ratio from 4.9 to 6.9, a mean $AUC_{0-inf}$ ratio from 14.0 to 16.0, and a mean $AUC_{0-6}$ ratio from 15.2 to 17.2, where the ratio refers to the ratio of the γ-hydroxybutyrate value to the compound (1) value. Following oral administration of an IR composition comprising 7.25 g compound (1) to a population of fasted, healthy subjects a plasma pharmacokinetic profile can be characterized by a mean $C_{max}$ ratio from 5.4 to 6.4, a mean $AUC_{0-inf}$ ratio from 14.5 to 15.5, and a mean $AUC_{0-6}$ ratio from 15.7 to 16.7, where the ratio refers to the ratio of the γ-hydroxybutyrate value to the compound (1) value.

Following oral administration of an MR1 composition comprising 7.25 g compound (1) to a population of fasted, healthy subjects a plasma pharmacokinetic profile is characterized by a mean $C_{max}$ ratio of 6.6, a mean $AUC_{0-inf}$ ratio of 10.0, and a mean $AUC_{0-6}$ ratio of 9.8, where the ratio refers to the ratio of the γ-hydroxybutyrate value to the compound (1) value. Following oral administration of an MR1 composition comprising 7.25 g compound (1) to a population of fasted, healthy subjects a plasma pharmacokinetic profile is characterized by a mean $C_{max}$ ratio from 6.2 to 7.0, a mean $AUC_{0-inf}$ ratio from 9.0 to 11.0, and a mean $AUC_{0-6}$ ratio from 9.4 to 10.2, where the ratio refers to the ratio of the γ-hydroxybutyrate value to the compound (1) value. Following oral administration of an MR1 composition comprising 7.25 g compound (1) to a population of fasted, healthy subjects a plasma pharmacokinetic profile is characterized by a mean $C_{max}$ ratio from 6.4 to 6.8, a mean $AUC_{0-inf}$ ratio from 9.5 to 10.5, and a mean $AUC_{0-6}$ ratio from 9.6 to 10.0, where the ratio refers to the ratio of the γ-hydroxybutyrate value to the compound (1) value.

Following oral administration of an MR2 composition comprising 7.25 g compound (1) to a population of fasted, healthy subjects a plasma pharmacokinetic profile is characterized by a mean $C_{max}$ ratio of 6.3, a mean $AUC_{0-inf}$ ratio of 11.9, and a mean $AUC_{0-6}$ ratio of 11.5, where the ratio refers to the ratio of the γ-hydroxybutyrate value to the compound (1) value. Following oral administration of an MR2 composition comprising 7.25 g compound (1) to a population of fasted, healthy subjects a plasma pharmacokinetic profile is characterized by a mean $C_{max}$ ratio from 5.9 to 6.7, a mean $AUC_{0-inf}$ ratio from 11.5 to 12.3, and a mean $AUC_{0-6}$ ratio from 11.1 to 11.9, where the ratio refers to the ratio of the γ-hydroxybutyrate value to the compound (1) value. Following oral administration of an MR2 composition comprising 7.25 g compound (1) to a population of fasted, healthy subjects a plasma pharmacokinetic profile is characterized by a mean $C_{max}$ ratio from 6.1 to 6.5, a mean $AUC_{0-inf}$ ratio from 11.7 to 12.1, and a mean $AUC_{0-6}$ ratio from 11.3 to 11.7, where the ratio refers to the ratio of the γ-hydroxybutyrate value to the compound (1) value.

Following oral administration of an MR3 composition comprising 7.25 g compound (1) to a population of fasted, healthy subjects a plasma pharmacokinetic profile is characterized by a mean $C_{max}$ ratio of 6.5, a mean $AUC_{0-inf}$ ratio of 11.4, and a mean $AUC_{0-6}$ ratio of 11.4, where the ratio refers to the ratio of the γ-hydroxybutyrate value to the compound (1) value. Following oral administration of an MR3 composition comprising 7.25 g compound (1) to a population of fasted, healthy subjects a plasma pharmacokinetic profile is characterized by a mean $C_{max}$ ratio from 6.1 to 6.9, a mean $AUC_{0-inf}$ ratio from 11.0 to 11.8, and a mean $AUC_{0-6}$ ratio from 11.0 to 11.8, where the ratio refers to the ratio of the γ-hydroxybutyrate value to the compound (1) value. Following oral administration of an MR3 composition comprising 7.25 g compound (1) to a population of fasted, healthy subjects a plasma pharmacokinetic profile is characterized by a mean $C_{max}$ ratio from 6.3 to 6.7, a mean $AUC_{0-inf}$ ratio from 11.2 to 11.6, and a mean $AUC_{0-6}$ ratio from 11.2 to 11.6, where the ratio refers to the ratio of the γ-hydroxybutyrate value to the compound (1) value.

A pharmaceutical composition can comprise an immediate release component and a modified component.

An immediate release component can comprise any of the immediate release microparticles disclosed herein.

A modified component can comprise any of the modified microparticles or combinations of modified microparticles disclosed herein.

A pharmaceutical composition provided by the present disclosure can comprise, for example, from 10 wt % to 50 wt % compound (1) in an IR component and from 50 wt % to 90 wt % in a MR component, from 20 wt % to 40 wt % compound (1) in an IR component and from 60 wt % to 80 wt % γ-hydroxybutyrate in an MR component, or from 25 wt % to 35 wt % compound (1) in an IR component and from 65 wt % to 75 wt % compound (1) in an MR component, where wt % is based on the total weight of compound (1) in the pharmaceutical composition.

A pharmaceutical composition provided by the present disclosure can comprise, for example, greater than 10 wt % compound (1) in an IR component and less than 90% compound (1) in an MR component, greater than 20 wt % compound (1) in an IR component and less than 80% compound (1) in an MR components, greater than 30 wt % compound (1) in an IR component and less than 70% compound (1) in an MR component, or greater than 40 wt % compound (1) in an IR component and less than 60% compound (1) in an MR component, where wt % is based on the total weight of compound (1) in the pharmaceutical composition.

A pharmaceutical composition provided by the present disclosure can have a weight ratio of compound (1) in an IR component to compound (1) in a MR component, for example, from 1:1.4 to 1:3.4, from 1:1.6 to 1.3.2, from 1.1.8 to 1:3.0, from 1:2.0 to 1:2.8, or from 1.22 to 1:2.6. P311 A pharmaceutical composition provided by the present disclosure can have a weight ratio of compound (1) in an IR component to compound (1) in an MR component, for example, greater than 1:1.4, greater than 1:1.6, greater than 1:1.8, greater than 1:2.0, greater than 1:2.2, greater than 1:2.4 or greater than 1:2.6.

A pharmaceutical composition provided by the present disclosure can comprise, for example, from 2.0 g to 6.0 g of compound (1) in an IR component, from 2.25 g to 5.75 g, from 2.5 g to 5.5 g, from 2.75 g to 5.25 g, from 3.0 g to 5.0 g, from 3.25 g to 4.75 g or from 3.5 g to 4.5 g of compound (1) in an IR component.

A pharmaceutical composition can comprise, for example, from 8 g to 12 g of compound (1) in an MR component, from 8.5 g to 11.5 g, from 9 g to 11 g, from 9.25 g to 10.75 g, or from 9.5 g to 10.5 g of compound (1) in an MR component.

A pharmaceutical composition can comprise for example, from 2.0 g to 6.0 g of compound (1) in an IR component, from 2.25 g to 5.75 g, from 2.5 g to 5.5 g, from 2.75 g to 5.25 g, from 3.0 g to 5.0 g, from 3.25 g to 4.75 g or from 3.5 g to 4.5 g of compound (1) in an IR component; and from 8 g to 12 g of compound (1) in an MR component, from 8.5 g to 11.5 g, from 9 g to 11 g, from 9.25 g to 10.75 g, or from 9.5 g to 10.5 g of compound (1) in an MR component.

A pharmaceutical composition provided by the present disclosure can comprise, for example, from 9.5 g to 22 g compound (1), from 10 g to 20 g compound (1), from 12 g to 18 g compound (1), or from 14 g to 16 g compound (1). A pharmaceutical composition provided by the present disclosure can comprise, for example, greater than 9 g compound (1), greater than 10 g, greater than 12 g, greater than 14 g, greater than 16 g, greater than 18 g, or greater than 20 g compound (1).

A pharmaceutical composition provided by the present disclosure can comprise, for example, from 10 wt % to 50 wt % γ-hydroxybutyrate equivalents in an IR component and from 50 wt % to 90 wt % in a MR component, from 20 wt % to 40 wt % γ-hydroxybutyrate equivalents in an IR component and from 60 wt % to 80 wt % γ-hydroxybutyrate in an MR component, or from 25 wt % to 35 wt % γ-hydroxybutyrate equivalents in an IR component and from 65 wt % to 75 wt % γ-hydroxybutyrate equivalents in an MR component, where wt % equivalents is based on the total wt % of γ-hydroxybutyrate equivalents in the pharmaceutical composition.

A pharmaceutical composition provided by the present disclosure can comprise, for example, greater than 10 wt % γ-hydroxybutyrate equivalents in an IR component and less than 90% γ-hydroxybutyrate equivalents in an MR components, greater than 20 wt % γ-hydroxybutyrate equivalents in an IR component and less than 80 wt % γ-hydroxybutyrate equivalents in an MR components, greater than 30 wt % γ-hydroxybutyrate equivalents in an IR component and less than 70 wt % γ-hydroxybutyrate equivalents in an MR components, or greater than 40 wt % γ-hydroxybutyrate in an IR component and less than 60 wt % γ-hydroxybutyrate in an MR components, where wt % equivalents is based on the total γ-hydroxybutyrate equivalents in the pharmaceutical composition.

A pharmaceutical composition provide by the present disclosure can have a weight ratio of γ-hydroxybutyrate equivalents in an IR component to γ-hydroxybutyrate equivalents in a MR component, for example, from 1:1.5 to 1:3.5, from 1:1.7 to 1.3.3, from 1.1.9 to 1:3.1, from 1:2.1 to 1:2.9, or from 1.23 to 1:2.7.

A pharmaceutical composition provided by the present disclosure can have a weight ratio of γ-hydroxybutyrate equivalents in an IR component to γ-hydroxybutyrate equivalents in an MR component, for example, greater than 1:1.5, greater than 1:1.7, greater than 1:1.9, greater than 1:2.1, greater than 1:2.3, greater than 1:2.5 or greater than 1:2.7.

A pharmaceutical composition provided by the present disclosure can comprise, for example, from 1.1 g to 3.1 g of γ-hydroxybutyrate equivalents in an IR component, from 1.2 g to 3.0 g, from 1.3 g to 2.9 g, or from 1.4 g to 2.8 g, γ-hydroxybutyrate equivalents in an IR component.

A pharmaceutical composition can comprise, for example, from 4.1 g to 6.1 g of γ-hydroxybutyrate equivalents in an MR component, from 4.2 g to 6.0 g, from 4.3 g to 5.9 g, from 4.4 g to 6.8 g, or from 4.5 g to 6.7 g of γ-hydroxybutyrate equivalents in an MR component.

A pharmaceutical composition can comprise for example, from 1.1 g to 3.1 g of γ-hydroxybutyrate equivalents in an IR component and from 4.1 g to 6.1 g of γ-hydroxybutyrate equivalents in an MR component; from 1.4 g to 2.8 g of γ-hydroxybutyrate equivalents in an IR component and from 4.3 g to 5.9 g of γ-hydroxybutyrate equivalents in an MR component; from 1.6 g to 2.6 g of γ-hydroxybutyrate equivalents in an IR component and from 4.5 g to 5.7 g of γ-hydroxybutyrate equivalents in an MR component; or from 1.8 g to 2.2 g of γ-hydroxybutyrate equivalents in an IR component and from 4.7 g to 5.5 g of γ-hydroxybutyrate equivalents in an MR component.

A pharmaceutical composition provided by the present disclosure can comprise, for example, from 6.5 g to 18 g compound (1), from 8 g to 16 g γ-hydroxybutyrate equivalents, from 10 g to 14 g compound (1), or from 11 g to 13 g γ-hydroxybutyrate equivalents. A pharmaceutical composition provided by the present disclosure can comprise, for example, greater than 9 g γ-hydroxybutyrate equivalents, greater than 6.5 g, greater than 8 g, greater than 10 g, greater than 12 g, greater than 14 g, or greater than 16 g γ-hydroxybutyrate equivalents.

The methods for determining the plasma pharmacokinetic profile for γ-hydroxybutyrate and 4-((L-valyl)oxy)butanoic acid (1) following administration of 4-((L-valyl)oxy)butanoic acid (1) fasted, healthy subjects is provided in the experimental examples.

Following oral administration of a combined release composition (CR1) comprising an IR composition comprising 4.11 g compound (1), and an MR1 composition comprising 10 g compound (1) to a population of fasted, healthy subjects, the plasma pharmacokinetic profile of compound (1) can be characterized by a mean $t_{1/2}$ of 1.1 hours, a mean $T_{max}$ of 1.4 hours, a mean $C_{max}$ of 15 μg/mL, a mean $AUC_{0-6}$ of 25 h×μg/mL, a mean $AUC_{0-inf}$ of 27 h×μg/mL, and a mean CL/F of 556 L/h.

Following oral administration of a combined release composition (CR1) comprising an IR composition comprising 4.11 g compound (1), and an MR1 composition comprising 10 g compound (1) to a population of fasted, healthy subjects, the plasma pharmacokinetic profile of compound (1) can be characterized by a mean $t_{1/2}$ from 1.0 hours 1.2 hours, a mean $T_{max}$ from 1.3 hours to 1.5 hours, a mean $C_{max}$ from 12 μg/mL to 18 μg/mL, a mean $AUC_{0-6}$ from 20 h×μg/mL to 30 h×μg/mL, a mean $AUC_{0-inf}$ from 22 h×μg/mL to 32 h×μg/mL, and a mean CL/F from 536 L/h to 576 L/h.

Following oral administration of a combined release composition (CR1) comprising an IR composition comprising 4.11 g compound (1), and an MR1 composition comprising 10 g compound (1) to a population of fasted, healthy subjects, the plasma pharmacokinetic profile of compound (1) can be characterized by a mean $t_{1/2}$ from 1.05 hours to 1.15 hours, a mean $T_{max}$ from 1.35 hours to 1.45 hours, a mean $C_{max}$ from 14 μg/mL to 16 μg/mL, a mean $AUC_{0-6}$ from 22 h×μg/mL to 28 h×μg/mL, a mean $AUC_{0-inf}$ from 24 h×μg/mL to 30 h×μg/mL, and a mean CL/F from 546 L/h to 566 L/h.

Following oral administration of a combined release composition (CR1) comprising an IR composition comprising 4.11 g compound (1), and an MR1 composition comprising 10 g compound (1) to a population of fasted, healthy subjects, the plasma pharmacokinetic profile of γ-hydroxybutyrate can be characterized by a mean $t_{1/2}$ of 1.1 hours, a mean $T_{max}$ of 2.7 hours, a mean $C_{max}$ of 108 μg/mL, a mean $AUC_{0-6}$ of 400 h×μg/mL, a mean $AUC_{0-inf}$ of 534 h×μg/mL, and a mean CL/F of 32 L/h.

Following oral administration of a combined release composition (CR1) comprising an IR composition comprising 4.11 g compound (1), and an MR1 composition comprising 10 g compound (1) to a population of fasted, healthy subjects, the plasma pharmacokinetic profile of γ-hydroxybutyrate can be characterized by a mean $t_{1/2}$ from 1.0 hours to 1.2 hours, a mean $T_{max}$ from 2.5 to 2.9 hours, a mean $C_{max}$ from 88 μg/mL to 128 μg/mL, a mean $AUC_{0-6}$ from 380 h×μg/mL to 420 h×μg/mL, a mean $AUC_{0-inf}$ from 514 h×μg/mL to 554 h×μg/mL, and a mean CL/F from 22 L/h to 42 L/h.

Following oral administration of a combined release composition (CR1) comprising an IR composition comprising 4.11 g compound (1), and an MR1 composition comprising 10 g compound (1) to a population of fasted, healthy subjects, the plasma pharmacokinetic profile of γ-hydroxybutyrate can be characterized by a mean $t_{1/2}$ from 1.05 hours to 1.15 hours, a mean $T_{max}$ from 2.6 to 2.8 hours, a mean $C_{max}$ from 98 μg/mL to 118 μg/mL, a mean $AUC_{0-6}$ from 390 h×μg/mL to 410 h×μg/mL, a mean $AUC_{0-inf}$ from 524 h×μg/mL to 544 h×μg/mL, and a mean CL/F from 27 L/h to 37 L/h.

Following oral administration of a combined release composition (CR1) comprising an IR composition comprising 4.11 g compound (1), and an MR1 composition comprising 10 g compound (1) to a population of fasted, healthy subjects, the plasma pharmacokinetic profile can be characterized by a mean $C_{max}$ ratio of 8.0, and a mean $AUC_{0-inf}$ ratio of 19.3, where the ratio refers to the ratio of the γ-hydroxybutyrate value to the compound (1) value.

Following oral administration of a combined release composition (CR1) comprising an IR composition comprising 4.11 g compound (1), and an MR1 composition comprising 10 g compound (1) to a population of fasted, healthy subjects, the plasma pharmacokinetic profile can be characterized by a mean $C_{max}$ ratio from 7.0 to 9.0, and a mean $AUC_{0-inf}$ ratio from 18.3 to 20.3, where the ratio refers to the ratio of the γ-hydroxybutyrate value to the corresponding compound (1) value.

Following oral administration of a combined release composition (CR1) comprising an IR composition comprising 4.11 g compound (1), and an MR1 composition comprising 10 g compound (1) to a population of fasted, healthy subjects, the plasma pharmacokinetic profile can be characterized by a mean $C_{max}$ ratio from 7.5 to 8.5, and a mean $AUC_{0-inf}$ ratio from 18.8 to 19.8, where the ratio refers to the ratio of the γ-hydroxybutyrate value to the corresponding compound (1) value.

Following oral administration of a combined release composition (CR2) comprising an IR composition comprising 4.11 g compound (1), and an MR2 composition comprising 10 g compound (1) to a population of fasted, healthy subjects, the plasma pharmacokinetic profile of compound (1) can be characterized by a mean $t_{1/2}$ of 1.0 hours, a mean $T_{max}$ of 1.3 hours, a mean $C_{max}$ of 12 μg/mL, a mean $AUC_{0-6}$ of 20 h×μg/mL, a mean $AUC_{0-inf}$ of 21 h×μg/mL, and a mean CL/F of 700 L/h).

Following oral administration of a combined release composition (CR2) comprising an IR composition comprising 4.11 g compound (1), and an MR2 composition comprising 10 g compound (1) to a population of fasted, healthy subjects, the plasma pharmacokinetic profile of compound (1) can be characterized by a mean $t_{1/2}$ from 0.9 hours to 1.1 hours, a mean $T_{max}$ from 1.1 hours to 1.5 hours, a mean $C_{max}$ from 10 μg/mL to 14 μg/mL, a mean $AUC_{0-6}$ from 16 h×μg/mL to 24 h×μg/mL, a mean $AUC_{0-inf}$ from 11 h×μg/mL to 31 h×μg/mL, and a mean CL/F of 660 L/h to 740 L/h.

Following oral administration of a combined release composition (CR2) comprising an IR composition comprising 4.11 g compound (1), and an MR2 composition comprising 10 g compound (1) to a population of fasted, healthy subjects, the plasma pharmacokinetic profile of compound (1) can be characterized by a mean $t_{1/2}$ from 0.95 hours to 1.05 hours, a mean $T_{max}$ from 1.2 hours to 1.4 hours, a mean $C_{max}$ from 11 μg/mL to 13 μg/mL, a mean $AUC_{0-6}$ from 18 h×μg/mL to 22 h×μg/mL, a mean $AUC_{0-inf}$ from 16 h×μg/mL to 26 h×μg/mL, and a mean CL/F of 680 L/h to 720 L/h.

Following oral administration of a combined release composition (CR2) comprising an IR composition comprising 4.11 g compound (1), and an MR2 composition comprising 10 g compound (1) to a population of fasted, healthy subjects, the plasma pharmacokinetic profile of γ-hydroxybutyrate can be characterized by a mean $t_{1/2}$ of 0.9 hours, a mean $T_{max}$ of 2.2 hours, a mean $C_{max}$ of 83 μg/mL, a mean $AUC_{0-6}$ of 322 h×μg/mL, a mean $AUC_{0-inf}$ of 386 h×μg/mL, and a mean CL/F of 43 L/h).

Following oral administration of a combined release composition (CR2) comprising an IR composition comprising 4.11 g compound (1), and an MR2 composition comprising 10 g compound (1) to a population of fasted, healthy subjects, the plasma pharmacokinetic profile of γ-hydroxybutyrate can be characterized by a mean $t_{1/2}$ from 0.8 hours to 1.0 hours, a mean $T_{max}$ from 2.0 hours to 2.4 hours, a mean $C_{max}$ from 73 μg/mL to 93 μg/mL, a mean $AUC_{0-6}$ from 302 h×μg/mL to 342 h×μg/mL, a mean $AUC_{0-inf}$ from 366 h×μg/mL to 406 h×μg/mL, and a mean CL/F from 33 L/h to 53 L/h.

Following oral administration of a combined release composition (CR2) comprising an IR composition comprising 4.11 g compound (1), and an MR2 composition comprising 10 g compound (1) to a population of fasted, healthy subjects, the plasma pharmacokinetic profile of γ-hydroxybutyrate can be characterized by a mean $t_{1/2}$ from 0.85 hours to 0.95 hours, a mean $T_{max}$ from 2.1 hours to 2.3 hours, a mean $C_{max}$ from 78 μg/mL to 88 μg/mL, a mean $AUC_{0-6}$ from 312 h×μg/mL to 332 h×μg/mL, a mean $AUC_{0-inf}$ from 376 h×μg/mL to 396 h×μg/mL, and a mean CL/F from 38 L/h to 48 L/h.

Following oral administration of a combined release composition (CR2) comprising an IR composition comprising 4.11 g compound (1), and an MR2 composition comprising 10 g compound (1) to a population of fasted, healthy subjects, the plasma pharmacokinetic profile can be characterized by a mean $C_{max}$ ratio of 7.8, and a mean $AUC_{0-inf}$ ratio of 18.3, where the ratio refers to the ratio of the γ-hydroxybutyrate value to the compound (1) value.

Following oral administration of a combined release composition (CR2) comprising an IR composition comprising 4.11 g compound (1), and an MR2 composition comprising 10 g compound (1) to a population of fasted, healthy subjects, the plasma pharmacokinetic profile can be characterized by a mean $C_{max}$ ratio from 6.8 to 8.8, and a mean $AUC_{0-inf}$ ratio from 17.3 to 19.3, where the ratio refers to the ratio of the γ-hydroxybutyrate value to the corresponding compound (1) value.

Following oral administration of a combined release composition (CR2) comprising an IR composition comprising 4.11 g compound (1), and an MR2 composition comprising 10 g compound (1) to a population of fasted, healthy subjects, the plasma pharmacokinetic profile can be characterized by a mean $C_{max}$ ratio from 7.3 to 8.3, and a mean $AUC_{0-inf}$ ratio from 17.8 to 18.8, where the ratio refers to the ratio of the γ-hydroxybutyrate value to the corresponding compound (1) value.

For a combined release composition provided by the present disclosure at 8 hours following oral administration of the combined release composition comprising from 10 g to 20 g compound (1) to a population of fasted, healthy subjects, the concentration of γ-hydroxybutyrate in the plasma of the subjects is less than 40 μg/mL, less than 30 μg/mL, or less than 20 μg/mL.

For a combined release composition provided by the present disclosure following oral administration of the combined release composition comprising from 10 g to 20 g of compound (1) to a population of fasted, healthy subjects, the $AUC_{inf}$ of γ-hydroxybutyrate in the plasma of the subjects is greater than the sum of: (a) the $AUC_{inf}$ of γ-hydroxybutyrate following oral administration of the immediate release component; and (b) the $AUC_{inf}$ of γ-hydroxybutyrate following oral administration of the modified release component to the population of fasted, healthy subjects.

For a combined release composition provided by the present disclosure between 6 hours and 8 hours following oral administration of the combined release composition comprising from 10 g to 20 g compound (1) to a population of fasted, healthy subjects, the γ-hydroxybutyrate concentration in the plasma of the subjects is greater than the sum of: (a) the γ-hydroxybutyrate concentration between 6 hours and 8 hours following oral administration of the immediate release component; and (b) the γ-hydroxybutyrate concentration between 6 hours and 8 hours following oral administration of the modified release component to the population of fasted, healthy subjects.

For a combined release composition provided by the present disclosure following oral administration of the combined release composition comprising from 10 g to 20 g compound (1) to a population of healthy, fasted subjects, concentration from 6 hours to 8 hours following administration is greater than the concentration of γ-hydroxybutyrate in the plasma of the subjects following administration of the modified release component alone.

For a combined release composition provided by the present disclosure the mean γ-hydroxybutyrate $AUC_{0-inf}$ following oral administration of the immediate release component and the modified release component to a population of fasted, healthy subjects is greater than the sum of the sum of the mean γ-hydroxybutyrate $AUC_{0-inf}$ following oral administration of the immediate release component alone, and the mean γ-hydroxybutyrate $AUC_{0-inf}$ following oral administration of the modified release component alone.

For a combined release composition provided by the present disclosure the mean compound (1) $AUC_{0-inf}$ following oral administration of the immediate release component and the modified release component to a population of subjects is substantially the same as than the sum of the sum of the mean compound (1) $AUC_{0-inf}$ following oral administration of the immediate release component alone, and the mean compound (1) $AUC_{0-inf}$ following oral administration of the modified release component alone.

For a combined release composition provided by the present disclosure the mean γ-hydroxybutyrate $AUC_{0-inf}$ following oral administration of a combined release composition comprising an immediate release component comprising 4.11 g compound (1) and a modified release component comprising 10 g compound (1) to a population of fasted, healthy subjects is greater than the sum of the mean γ-hydroxybutyrate $AUC_{0-inf}$ following oral administration of an immediate release component comprising 7.25 g compound (1) alone, and the mean γ-hydroxybutyrate $AUC_{0-inf}$ following oral administration of a modified release component comprising 7.25 g compound (1) alone.

For a combined release composition provided by the present disclosure the mean compound (1) $AUC_{0-inf}$ following oral administration of the combined release composition comprising an immediate release component comprising 4.52 g compound (1) and a modified release component comprising 10 g compound (1) to a population of fasted, healthy subjects is substantially the same as than the sum of the mean compound (1) $AUC_{0-inf}$ following oral administration of an immediate release component comprising 7.25 g compound (1) alone, and the mean compound (1) $AUC_{0-inf}$ following oral administration of a modified release component comprising 7.25 g compound (1) alone.

Figure 17:
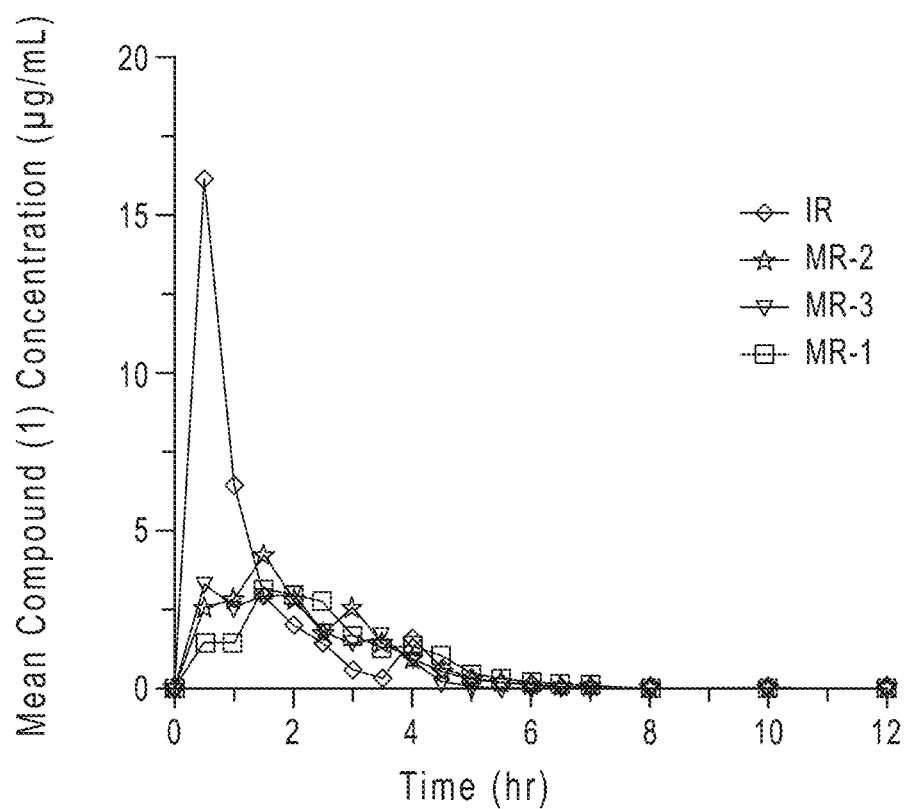
FIG. 17 shows the mean plasma concentration of compound (1) following oral administration of an immediate release (IR) composition or three modified release (MR1-MR3) compositions of compound (1) to fasted, healthy subjects.
Figure 18:
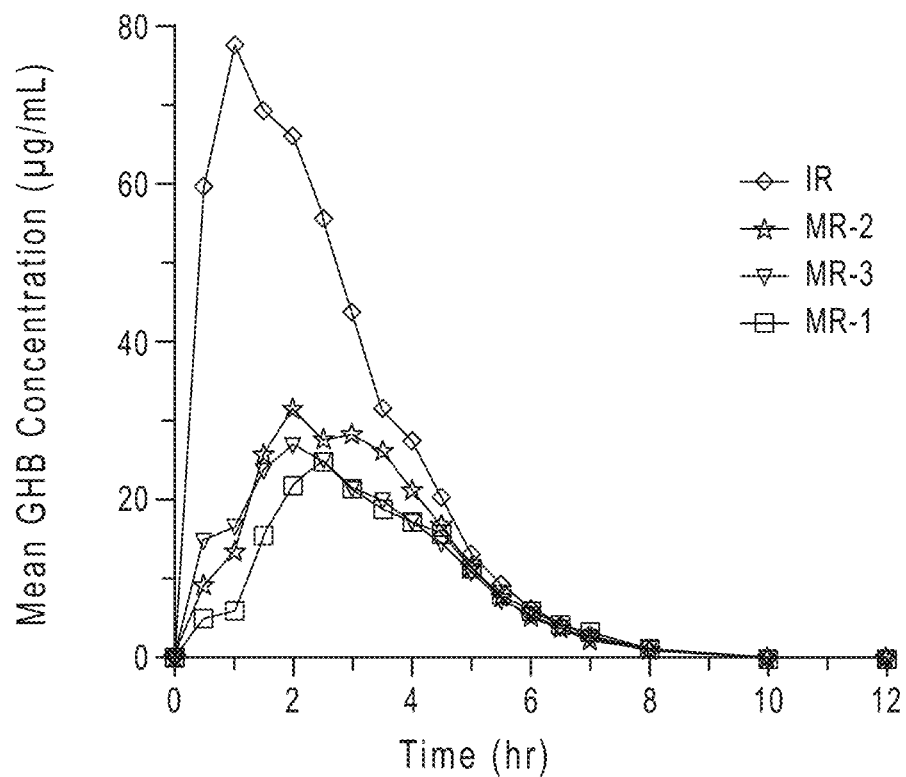
FIG. 18 shows the mean plasma γ-hydroxybutyrate concentration following oral administration of an immediate release (IR) composition or three modified release (MR1-MR3) compositions of compound (1) to fasted, healthy subjects.

An immediate release component provided by the present disclosure can exhibit a plasma pharmacokinetic profile that is bioequivalent to the plasma pharmacokinetic profile for compound (1) as shown in FIG. 17 or for γ-hydroxybutyrate as shown in FIG. 18. An immediate release component provided by the present disclosure can exhibit a plasma pharmacokinetic profile that is bioequivalent to the plasma pharmacokinetic profile for compound (1) as provided in Table 6 or for γ-hydroxybutyrate as provided in Table 7.

A modified release component provided by the present disclosure can exhibit a plasma pharmacokinetic profile that is bioequivalent to the plasma pharmacokinetic profile for compound (1) as shown in FIG. 17 or for γ-hydroxybutyrate as shown in FIG. 18. A modified release component provided by the present disclosure can exhibit a plasma pharmacokinetic profile that is bioequivalent to the plasma pharmacokinetic profile for compound (1) as provided in Table 6 or for γ-hydroxybutyrate as provided in Table 7.

Figure 19:
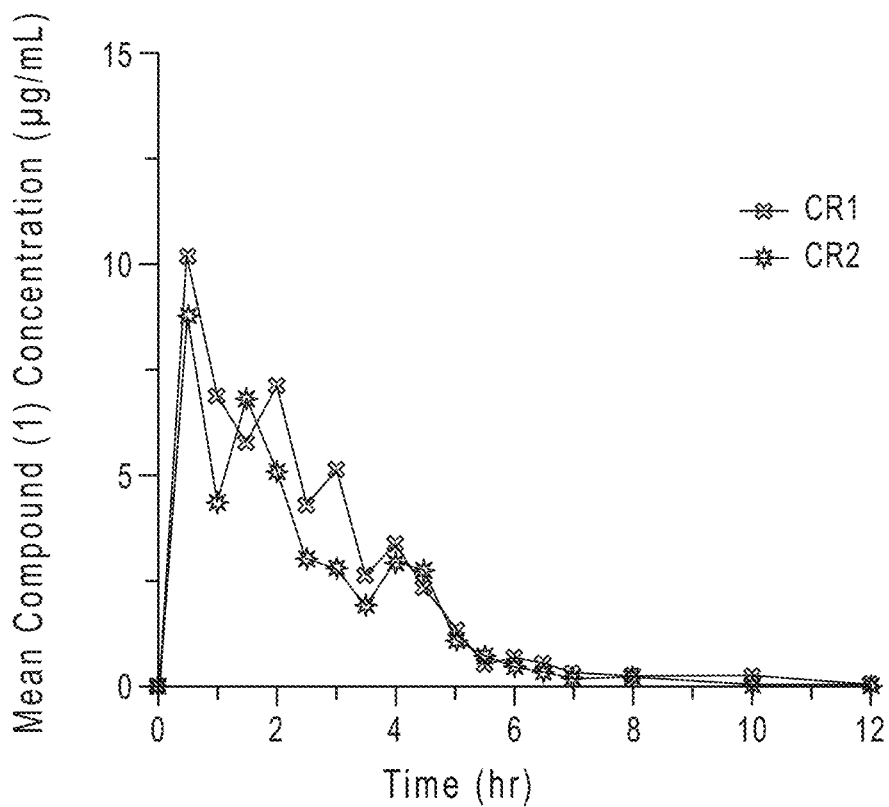
FIG. 19 shows the mean plasma concentration of compound (1) following oral administration of two controlled release compositions of compound (1) to fasted, healthy subjects.
Figure 20:
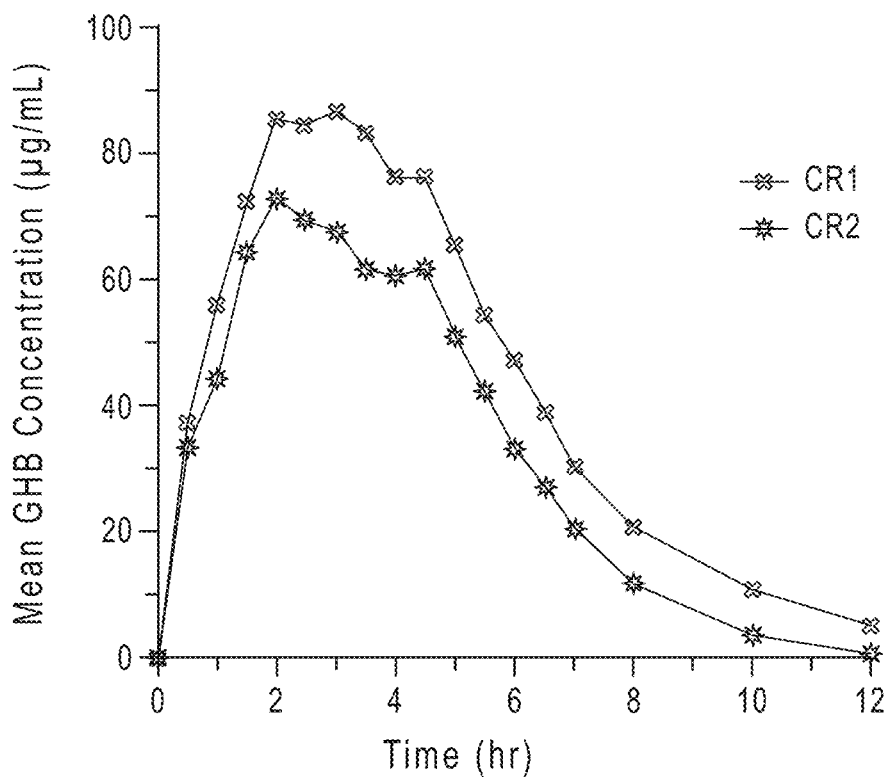
FIG. 20 shows the mean plasma γ-hydroxybutyrate concentration following oral administration of two controlled release compositions of compound (1) to fasted, healthy subjects.

A pharmaceutical composition provided by the present disclosure, such as a combined release composition, can exhibit a plasma pharmacokinetic profile that is bioequivalent to the plasma pharmacokinetic profile for compound (1) as shown in FIG. 19 or for γ-hydroxybutyrate as shown in FIG. 20. A pharmaceutical composition provided by the present disclosure, such as a combined release composition, can exhibit a plasma pharmacokinetic profile that is bioequivalent to the plasma pharmacokinetic profile for compound (1) provided in Table 10 or for γ-hydroxybutyrate as provided in Table 11.

A pharmaceutical composition provided by the present disclosure can be used, for example, to treat narcolepsy, excessive daytime sleepiness, cataplexy, excessive daytime sleepiness associated with narcolepsy, excessive daytime sleepiness associated with Parkinson's disease, excessive daytime sleepiness associated with multiple sclerosis, cataplexy associated with narcolepsy, fatigue, fatigue associated with Parkinson's diseases, fatigue associated with multiple sclerosis, and fibromyalgia.

A pharmaceutical composition provided by the present disclosure can be used, for example, to treat to treat REM sleep behavior disorder, spasmodic dystonia, schizophrenia, insomnia, insomnia associated with schizophrenia, idiopathic hypersomnia, chronic fatigue syndrome, cluster headache, Alzheimer's disease, essential tremor, post-traumatic stress syndrome, insomnia associated with post-traumatic stress syndrome, and anxiety.

A pharmaceutical composition provided by the present disclosure can be used, for example, to enhance cognitive function in a neurodegenerative disorder. For example, a pharmaceutical composition provided by the present disclosure can be used to enhanced cognitive function in a patient with Parkinson's disease or in a patient with Alzheimer's disease.

A pharmaceutical composition provided by the present disclosure can be used to treat narcolepsy such as Type 1 or Type 2 narcolepsy. The treatment of narcolepsy is defined as reducing excessive daytime sleepiness or reducing the frequency of cataplectic attacks. In various embodiments, the composition is sufficient to be administered once daily. For example, the composition may be sufficient to administer in the morning or at night less than 2 hours after eating a meal. A pharmaceutical composition can also effective to induce sleep for at least 6 to 8 consecutive hours. A pharmaceutical composition administered less than two hours after eating is effective to induce sleep for at least 8 consecutive hours. A pharmaceutical composition can be effective to induce sleep for at least 6 hours, at least 7 hours, at least 8 hours, at least 9 hours, or at least 10 hours. A pharmaceutical composition can be effective to induce sleep for up to 6 hours, up to 7 hours, up to 8 hours, up to 9 hours, or up to 10 hours.

A pharmaceutical composition and composition provided by the present disclosure can be used to treat a sleeping disorder, drug abuse, alcohol and opiate withdrawal, a reduced level of growth hormone, anxiety, analgesia, a symptom associated with a neurological disorder such as Parkinson's disease, Alzheimer's disease and depression, an endocrine disturbance, hypoxia or anoxia of tissues such as from stroke or myocardial infarction, or an increased level of intracranial pressure.

A pharmaceutical composition provided by the present disclosure can be used to treat a disease o condition capable of being treated by administering γ-hydroxybutyric acid such as, for example, fibromyalgia and sleep disorders such as apnea, sleep time disturbances, narcolepsy, cataplexy, excessive daytime sleepiness (EDS), sleep paralysis, hypnagogic hallucination, sleep arousal, insomnia, and nocturnal myoclonus.

A pharmaceutical composition provided by the present disclosure can be used to treat a sleep disorder associated with a viral disease such as a COVID-19 infection.

A pharmaceutical composition provided by the present disclosure can be used for relieving pain and improving function in patients with fibromyalgia syndrome, and in alleviating excessive daytime sleepiness and fatigue in patients with Parkinson's disease, improving myoclonus and essential tremor, and reducing tardive dyskinesia and bipolar disorder.

A pharmaceutical composition provided by the present disclosure can be used to improve cognitive function in a patient with a neurological disorder such as Parkinson's disease and Alzheimer's disease.

A pharmaceutical composition and composition provide by the present disclosure can be used to treat a neurodegenerative disease or a condition or disorder associated with a neurovegetative disease in a patient where the neurodegenerative diseases is selected from, for example, Alzheimer's diseases, amyotrophic lateral sclerosis, Friedrich's ataxia, Huntington's diseases, Lewy body disease, Parkinson's disease, spinal muscular atrophy, motor neuron disease, Creutzfeldt Jakob disease, primary progressive aphasia, progressive supranuclear palsy. Other examples of neurodegenerative diseases include Alper's diseases, Batten disease, cerebro-oculo-facio-skeletal syndrome, corticobasal degeneration, Gerstmann-Straussler-Scheinker disease, kuru, Leigh's disease, monometic amyotrophy, multiple system atrophy, opsoclonus myoclonus, prion diseases, progressive multifocal leukoencephalopathy, leukoencephalopathy striatonigral degermation, and transmissible spongiform encephalopathies.

4-((L-Valyl)oxy)butanoic acid, which following administration is metabolized to provide γ-hydroxybutyric acid in the systemic circulation, can be used to treat narcolepsy, excessive daytime sleepiness, cataplexy, excessive daytime sleepiness associated with narcolepsy, excessive daytime sleepiness associated with Parkinson's disease, excessive daytime sleepiness associated with multiple sclerosis, cataplexy associated with narcolepsy, fatigue, fatigue associated with Parkinson's diseases, fatigue associated with multiple sclerosis, and fibromyalgia.

4-((L-Valyl)oxy)butanoic acid can be used to treat REM sleep behavior disorder, spasmodic dystonia, symptoms of schizophrenia, insomnia, insomnia associated with schizophrenia, idiopathic hypersomnia, chronic fatigue syndrome, cluster headache, symptoms of Alzheimer's disease, symptoms of Parkinson's disease, essential tremor, post-traumatic stress syndrome, insomnia associated with post-traumatic stress syndrome, and anxiety.

4-((L-Valyl)oxy)butanoic acid is a prodrug of γ-hydroxybutyric acid that following oral administration provide an oral bioavailability of γ-hydroxybutyric acid in the circulation of a patient.

4-((L-Valyl)oxy)butanoic acid and pharmaceutical compositions thereof can be used to treat a disease known to be or determined to be treated by administering γ-hydroxybutyric acid.

4-((L-Valyl)oxy)butanoic acid and pharmaceutical compositions thereof can be used to treat a disease known to be or determined to be treated by administering γ-hydroxybutyric acid and one or more additional therapeutic agents.

4-((L-Valyl)oxy)butanoic acid and pharmaceutical composition can be used to treat excessive daytime sleepiness associated with narcolepsy, excessive daytime sleepiness associated with Parkinson's disease, excessive daytime sleepiness associated with multiple sclerosis, cataplexy associated with narcolepsy, fatigue in a patient with Parkinson's disease, fatigue in a patient with multiple sclerosis, or fibromyalgia.

Methods provided by the present disclosure include providing a therapeutically effective amount of γ-hydroxybutyric acid in the systemic circulation of a patient comprising administering to a patient 4-((L-valyl)oxy)butanoic acid or a pharmaceutically acceptable salt thereof, or a pharmaceutical composition thereof.

A pharmaceutical composition provided by the present disclosure may further comprise one or more pharmaceutically active compounds in addition to 4-((L-valyl)oxy)butanoic acid). Such compounds may be provided to treat the disease being treated with 4-((L-valyl)oxy)butanoic acid) or to treat a disease, disorder, or condition other than that being treated with 4-((L-valyl)oxy)butanoic acid.

4-((L-Valyl)oxy)butanoic acid) or a pharmaceutical composition thereof may be used in combination with at least one other therapeutic agent. 4-((L-Valyl)oxy)butanoic acid or a pharmaceutical composition thereof may be administered to a patient together with another compound for treating a bacterial infection in the patient. 4-((L-Valyl)oxy) butanoic acid) and the at least one other therapeutic agent may act additively or synergistically. The at least one additional therapeutic agent may be included in the same pharmaceutical composition or vehicle comprising 4-((L-valyl)oxy)butanoic acid or may be in a separate pharmaceutical composition or vehicle. Accordingly, methods provided by the present disclosure further include, in addition to administering 4-((L-valyl)oxy)butanoic acid administering one or more therapeutic agents effective for treating a different disease, disorder or condition other than the disease being treated with γ-hydroxybutyric acid. Methods provided by the present disclosure include administration of 4-((L-valyl)oxy)butanoic acid or a pharmaceutical composition thereof and one or more other therapeutic agents provided that the combined administration does not inhibit the therapeutic efficacy of 4-((L-valyl)oxy)butanoic acid and/or γ-hydroxybutyric acid and/or does not produce adverse combination effects.

A pharmaceutical composition comprising 4-((L-valyl)oxy)butanoic acid may be administered concurrently with the administration of another therapeutic agent, which may be part of the same pharmaceutical composition as, or in a different pharmaceutical composition than, that comprising 4-((L-valyl)oxy)butanoic acid 4-((L-valyl)oxy)butanoic acid or a pharmaceutical composition thereof may be administered prior or subsequent to administration of another therapeutic agent. In certain embodiments of combination therapy, the combination therapy may comprise alternating between administering 4-((L-valyl)oxy)butanoic acid and a pharmaceutical composition comprising another therapeutic agent such as to minimize adverse drug effects associated with a particular drug. When 4-((L-valyl)oxy)butanoic acid is administered concurrently with another therapeutic agent that potentially may produce an adverse drug effect including, for example, toxicity, the other therapeutic agent may be administered at a dose that falls below the threshold at which the adverse drug reaction is elicited.

A pharmaceutical composition comprising 4-((L-valyl)oxy)butanoic acid may be administered with one or more substances, for example, to enhance, modulate and/or control release, bioavailability, therapeutic efficacy, therapeutic potency, and/or stability of 4-((L-valyl)oxy)butanoic acid. For example, to enhance the therapeutic efficacy of 4-((L-valyl)oxy)butanoic acid or a pharmaceutical composition comprising 4-((L-valyl)oxy)butanoic acid may be co-administered with one or more active agents to increase the absorption or diffusion and/or transport of 4-((L-valyl)oxy)butanoic acid from the gastrointestinal tract into the systemic circulation, or to inhibit degradation of 4-((L-valyl)oxy)butanoic acid in the blood of a patient. A pharmaceutical composition comprising 4-((L-valyl)oxy)butanoic acid may be co-administered with an active agent having pharmacological effects that enhance the therapeutic efficacy of 4-((L-valyl)oxy)butanoic acid or γ-hydroxybutyric acid.

ASPECTS OF THE INVENTION

The invention is further defined by the following aspects.

Aspect 1. A pharmaceutical granulation comprising a plurality of coated granules, wherein, the granules comprise a core and a functional coating surrounding the core; the pharmaceutical granulation is characterized by a particle size distribution (PSD) (D50) from 200 μm to 400 μm, wherein PSD is determined by sieve analysis; and the core comprises greater than 90 wt % of 4-((L-valyl)oxy)butanoic acid, wherein wt % is based on the total weight of the core.

Aspect 2. The pharmaceutical granulation of aspect 1, wherein the pharmaceutical granulation comprises from 60 wt % to 90 wt % of 4-((L-valyl)oxy)butanoic acid, wherein wt % is based on the total weight of the pharmaceutical granulation.

Aspect 3. The pharmaceutical granulation of any one of aspects 1 to 2, wherein the functional coating comprises a modified release coating.

Aspect 4. The pharmaceutical granulation of any one of aspects 1 to 3, wherein the functional coating comprises from 50 wt % to 85 wt % of a matrix polymer, wherein wt % is based on the total weight of the functional coating.

Aspect 5. The pharmaceutical granulation of aspect 4, wherein the matrix polymer comprises a water-insoluble polymer.

Aspect 6. The pharmaceutical granulation of aspect 5, wherein the water-insoluble polymer comprises ethylcellulose.

Aspect 7. The pharmaceutical granulation of any one of aspects 1 to 6, wherein the functional coating comprises from 0 wt % to 10 wt % of a pore forming polymer, wherein wt % is based on the total weight of the matrix polymer.

Aspect 8. The pharmaceutical granulation of aspect 7, wherein the pore forming polymer comprises a water-soluble polymer.

Aspect 9. The pharmaceutical granulation of aspect 8, wherein the water-soluble polymer comprises hydroxypropyl cellulose.

Aspect 10. The pharmaceutical granulation of any one of aspects 1 to 9, wherein the functional coating comprises from 10 wt % to 20 wt % an antistatic agent, wherein wt % is based on the total weight of the functional coating.

Aspect 11. The pharmaceutical granulation of aspect 10, wherein the antistatic agent comprises talc, magnesium stearate, or a combination thereof.

Aspect 12. The pharmaceutical granulation of any one of aspects 1 to 11, wherein the functional coating comprises: from 50 wt % to 85 wt % of a matrix polymer; and from 10 wt % to 20 wt % of an antistatic agent; wherein wt % is based on the total weight of the functional coating.

Aspect 13. The pharmaceutical granulation of any one of aspects 1 to 12, wherein, the core represents from 65 wt % to 85 wt % of the total weight of the coated granulation; and the functional coating represents from 15 wt % to 40 wt % of the total weight of the coated granulation.

Aspect 14. The pharmaceutical granulation of any one of aspects 1 to 13, wherein the functional coating has a thickness from 5 μm to 30 μm.

Aspect 15. The pharmaceutical granulation of any one of aspects 1 to 14, wherein the pharmaceutical granulation has a water content less than 2 wt %, wherein wt % is based on the total weight of the pharmaceutical granulation.

Aspect 16. The pharmaceutical granulation of any one of aspects 1 to 15, further comprising a seal coating surrounding the core, and wherein the functional coating surrounds the seal coating.

Aspect 17. The pharmaceutical granulation of aspect 16, wherein the seal coating comprises: hydroxypropyl cellulose; hydroxypropylmethyl cellulose; hydroxypropyl cellulose and talc; or hydroxypropylmethyl cellulose and talc.

Aspect 18. The pharmaceutical granulation of aspect 17, wherein the pharmaceutical granulation comprises from 2 wt % to 15 wt % of the seal coating.

Aspect 19. The pharmaceutical granulation of any one of aspects 1 to 18, wherein from 30 wt % to 80 wt % of the 4-((L-valyl)oxy)butanoic acid is released from the granulation within 2 hours when tested in a USP Type 2 dissolution apparatus in a buffered solution at pH 4.5 at a temperature of 37° C. and a paddle speed of 100 rpm, wherein wt % is based on the total weight of the 4-((L-valyl)oxy)butanoic acid in the granulation.

Aspect 20. The pharmaceutical granulation of any one of aspects 1 to 19, wherein from 50 wt % to 90 wt % of the 4-((L-valyl)oxy)butanoic acid is released from the granulation within 4 hours when tested in a USP Type 2 dissolution apparatus in a buffered solution at pH 4.5 at a temperature of 37° C. and a paddle speed of 100 rpm, wherein wt % is based on the total weight of the 4-((L-valyl)oxy)butanoic acid in the granulation.

Aspect 21. The pharmaceutical granulation of any one of aspects 1 to 20, wherein from 60 wt % to 100 wt % of the 4-((L-valyl)oxy)butanoic acid is released from the granulation within 6 hours when tested in a USP Type 2 dissolution apparatus in a buffered solution at pH 4.5 at a temperature of 37° C. and a paddle speed of 100 rpm, wherein wt % is based on the total weight of the 4-((L-valyl)oxy)butanoic acid in the granulation.

Aspect 22. A pharmaceutical composition comprising the pharmaceutical granulation of any one of aspects 1 to 21.

Aspect 23. The pharmaceutical composition of aspect 22, wherein the pharmaceutical composition is an oral composition.

Aspect 24. The pharmaceutical composition of aspect 23, wherein the oral composition comprises a modified release composition.

Aspect 25. The pharmaceutical composition of any one of aspects 23 to 24, wherein the oral composition comprises: a modified release portion, wherein the modified release portion comprises the pharmaceutical granulation; and the pharmaceutical composition further comprises an immediate release portion.

Aspect 26. The pharmaceutical composition of aspect 25, wherein the immediate release portion dissolves in water within less than 5 minutes.

Aspect 27. The pharmaceutical composition of any one of aspects 23 to 26, wherein the oral composition is a BID composition.

Aspect 28. The pharmaceutical composition of any one of aspects 23 to 27, wherein the oral composition is a QD composition.

Aspect 29. The pharmaceutical composition of any one of aspects 22 to 28, wherein the pharmaceutical composition comprises from 500 mg equivalents to 12 g equivalents of 4-((L-valyl)oxy)butanoic acid.

Aspect 30. The pharmaceutical composition of any one of aspects 22 to 29, wherein the pharmaceutical composition comprises a sustained release oral composition, a delayed release composition, an immediate release composition, or a combination of any of the foregoing.

Aspect 31. The pharmaceutical composition of any one of aspects 22 to 30, wherein the pharmaceutical composition comprises a therapeutically effective amount of 4-((L-valyl)oxy)butanoic acid for treating a disease in a patient, wherein the disease is selected from narcolepsy, cataplexy, excessive daytime sleepiness, fibromyalgia, chronic fatigue, and tardive dyskinesia.

Aspect 32. A method of treating a disease in a patient comprising administering to a patient in need of such treatment a therapeutically effective amount of the pharmaceutical composition of any one of aspects 22 to 31, wherein the disease is selected from narcolepsy, cataplexy, excessive daytime sleepiness, fibromyalgia, chronic fatigue, and tardive dyskinesia.

Aspect 33. The method of aspect 32, wherein the disease is cataplexy associated with narcolepsy.

Aspect 34. The method of aspect 32, wherein the disease is excessive daytime sleepiness associated with narcolepsy.

Aspect 35. The method of aspect 32, wherein the disease is excessive daytime sleepiness in a patient with Parkinson's disease.

Aspect 36. The method of aspect 32, wherein the disease is chronic fatigue in a patient with Parkinson's disease.

Aspect 37. The method of any one of aspects 32 to 36, wherein administering comprises orally administering.

Aspect 38. A method of coating a granulation comprising applying a coating composition to a pharmaceutical granulation comprising a plurality of granules comprising 4-((L-valyl)oxy)butanoic acid, wherein the coating composition comprises: from 6 wt % to 14 wt % solids; from 0 wt % to 20 wt % water; and from 70 wt % to 95 wt % ethanol, wherein wt % is based on the total weight of the coating composition.

Aspect 39. The method of aspect 38, wherein the solids comprise: a matrix polymer selected from hydroxypropylmethyl cellulose, hydroxypropyl cellulose, or a combination thereof; and an antistatic agent selected from talc, magnesium stearate, or a combination thereof.

Aspect 40. The method of any one of aspects 38 to 39, wherein applying comprises spraying.

EXAMPLES

Embodiments provided by the present disclosure are further illustrated by reference to the following examples, which describe coated pharmaceutical granulations comprising 4-((L-valyl)oxy)butanoic acid, coated pharmaceutical granules comprising 4-((L-valyl)oxy)butanoic acid, oral modified release pharmaceutical compositions and methods of making the coated pharmaceutical granulations and granules provided by the present disclosure. It will be apparent to those skilled in the art that many modifications, both to materials, and methods, may be practiced without departing from the scope of the disclosure.

General Methods

Pharmacokinetic Analysis

The plasma concentrations of Compound (1) and γ-hydroxybutyrate in plasma in healthy human subjects were measured using liquid chromatography tandem mass-spectroscopy and evaluated using Phoenix™ WinNonlin® version 8.1 (Pharsight Corporation, USA) and Microsoft® Excel® 2016 (Microsoft Corporation, USA).

Dissolution Profiles

The dissolution profiles for the modified release microparticles was determined using a USP Type 2 dissolution apparatus with a buffered solution at pH 4.5 at a temperature of 37° C. and a paddle speed of 75 rpm. The dissolution profiles for the release of compound (1) from the modified release microparticles is shown in FIG. 1.

Example 1

Water-Based Seal Coated Immediate Release Granulation of 4-((L-Valyl)oxy)butanoic Acid A seal-coated immediate release (IR) granulation was prepared by spray coating an uncoated IR granulation of 4-((L-valyl)oxy)butanoic acid granules.

The uncoated IR granulation comprising 4-((L-valyl)oxy)butanoic acid was prepared using MicroPX® micro-pelletizing technology (Glatt GmbH). The uncoated IR granulation had an average granule diameter (D50) from 225 μm to 275 μm. The uncoated IR granulation contained 90 wt % 4-((L-valyl)oxy)butanoic acid, 5 wt % USP magnesium silicate, and 5 wt % hypromellose (hydroxypropylmethyl cellulose), where wt % is based on the total weight of the IR granulation.

The composition used to provide the seal coat contained 14.2 wt % hydroxypropylmethyl cellulose (Pharmacoat®

603), 2.1 wt % talc and 85.6 wt % water, where wt % is based on the total weight of the seal coat composition.

The composition was sprayed-coated onto the uncoated IR granulation to provide a seal coating having a thickness of 2.23 (+/−0.34) µm.

The particle size distribution of the particles is shown in FIG. 1, and SEM images of the seal-coated granulation is shown in FIGS. 2A-2D, and an SEM image of a cross-sectional view of a seal-coated granule is shown in FIG. 2E.

Example 2

Acetone-Based Seal Coated Immediate Release Granulation of 4-((L-Valyl)oxy)butanoic Acid A seal-coated IR granulation was prepared by spray-coating an uncoated granulation of 4-((L-valyl)oxy)butanoic acid granules.

The uncoated IR granulation comprising 4-((L-valyl)oxy) butanoic acid was prepared using MicroPX® micro-pelletizing technology (Glatt GmbH). The uncoated IR granulation had an average granule diameter (D50) from 225 µm to 275 µm. The uncoated IR granulation had a 4-((L-valyl)oxy) butanoic acid content of greater than 90 wt %.

The composition used to provide the seal coat contained 5.4 wt % hydroxypropyl cellulose (Klucel® EF), 2.1 wt % talc and 92.5 wt % acetone, where wt % is based on the total weight of the seal coat composition.

The composition was sprayed-coated onto the uncoated granulation to provide a seal coating having a thickness of 1.30 (+/−0.27) µm.

The particle size distribution of the seal coated IR particles is shown in FIG. 3, and SEM images of the seal-coated granulation is shown in FIGS. 4A-4D, and an SEM image of a cross-sectional view of a seal-coated granule is shown in FIG. 4E.

Example 3

Granulation of 4-((L-Valyl)oxy)butanoic Acid Having a Modified Release Coating (1)

A granulation containing granules having 98.5 wt % of 4-((L-valyl)oxy)butanoic acid, and characterized by an average granule diameter (D50) from 225 µm to 275 µm was used to prepare a granulation having modified release (MR) coatings.

The constituents of the modified release coatings are provided in Table 1.

TABLE 1

| Modified release coating (1). | | |
|---|---|---|
| Constituent | Total (wt %) | Solids (wt %) |
| Ethoce ® Standard 10 ethylcellulose | 8.1 | 81.2 |
| Ethanol, 96% | 81.0 | — |
| Water | 9.0 | — |
| Pharmacoat® 603 Hydroxypropyl cellulose | 0.3 | 2.7 |
| Parteck ® LUB magnesium stearate | 1.6 | 16.1 |

The modified release coating was applied at 20% wg and 40% wg.

For the coated granulation having a 40% wg the bulk density was 0.70 g/mL and the (loss on drying) LOD was 0.55%. The thickness of the modified release coating at 40 wg % was 10.26 µm+/−1.46 µm (std).

Figure 5:
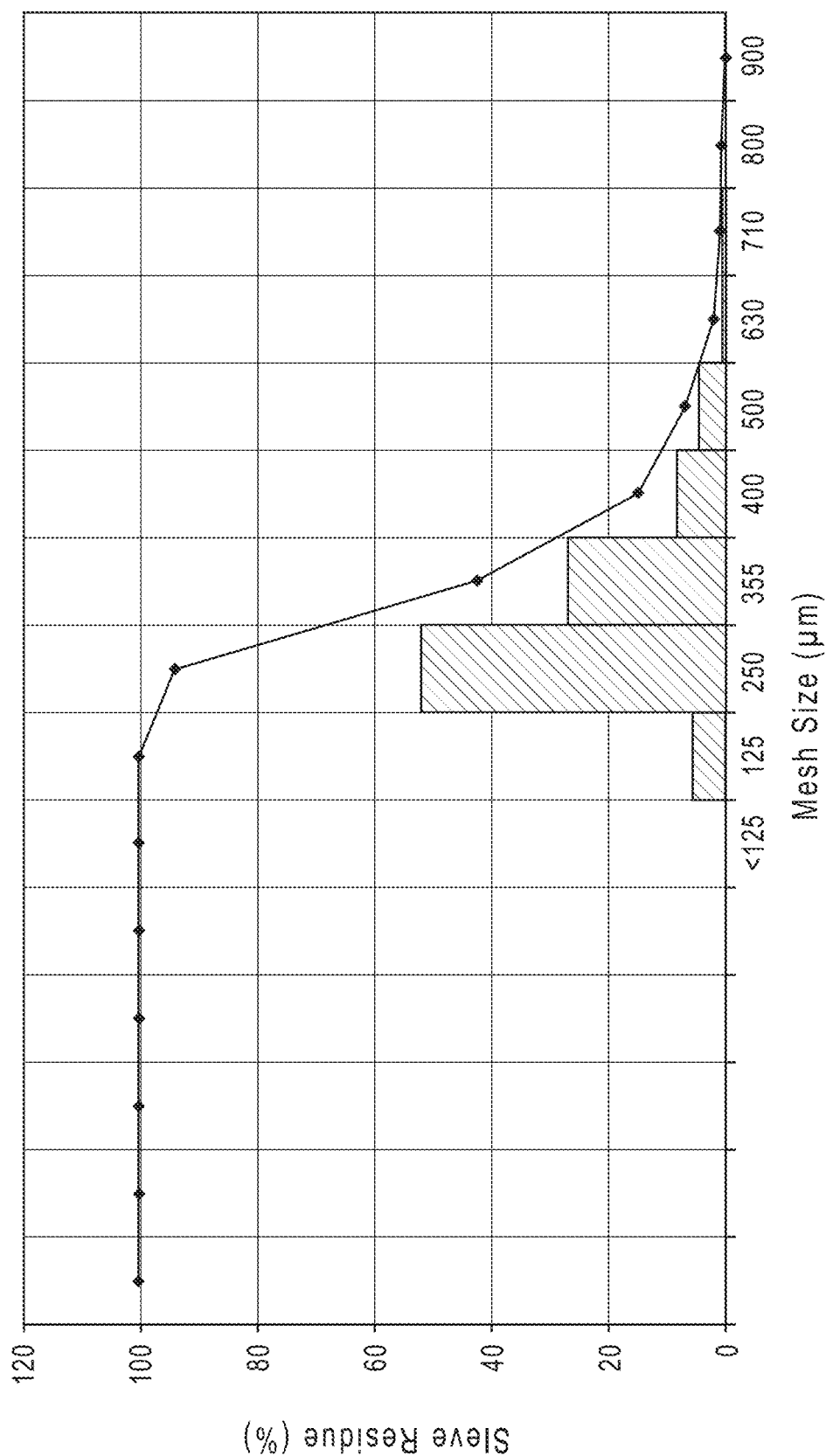
FIG. 5 shows the particle size distribution of coated granules comprising a 40% wg ethylcellulose/hydroxypropyl cellulose functional coating as described in Example 3.
Figure 6:
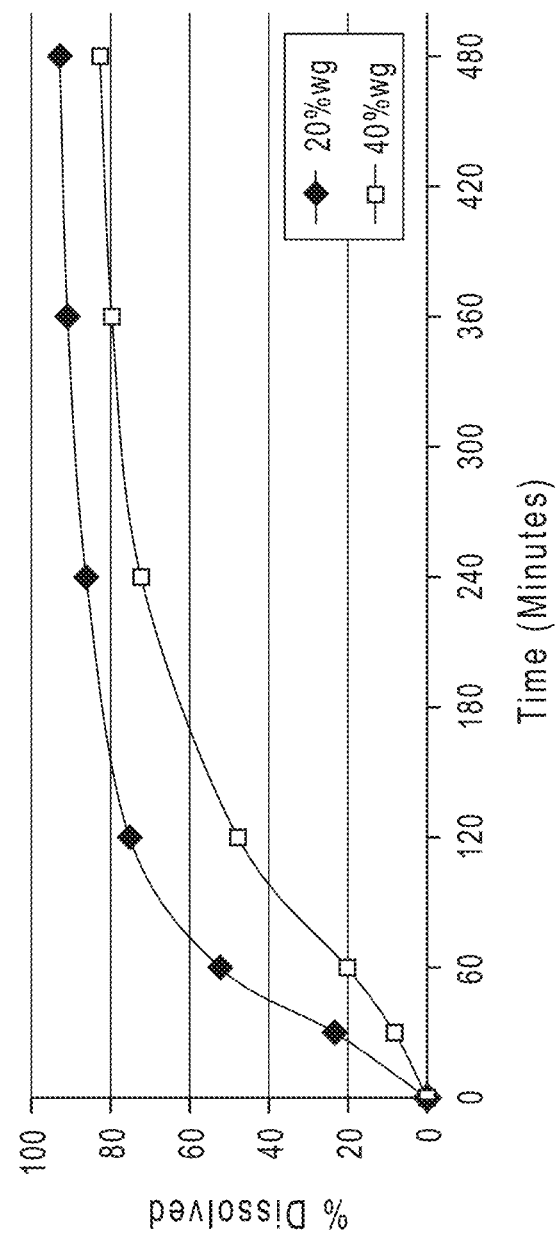
FIG. 6 shows dissolution profiles of 4-((L-valyl)oxy) butanoic acid from granules containing an ethylcellulose/ hydroxypropyl cellulose functional coating representing different % wg as described in Example 3.
Figure 7A:
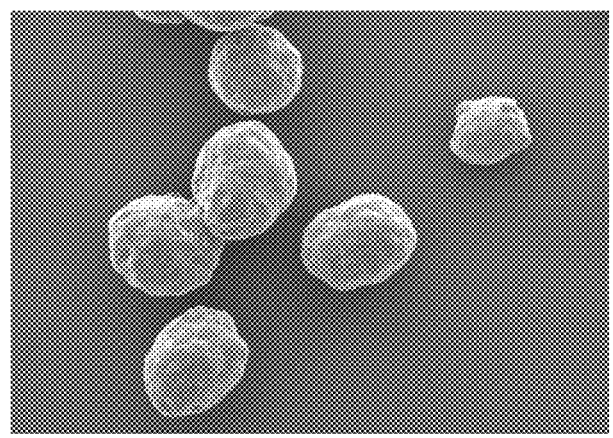
FIGS. 7A-7D show SEM images of the 40% wg coated granules at different magnifications as described in Example 3.
Figure 7B:
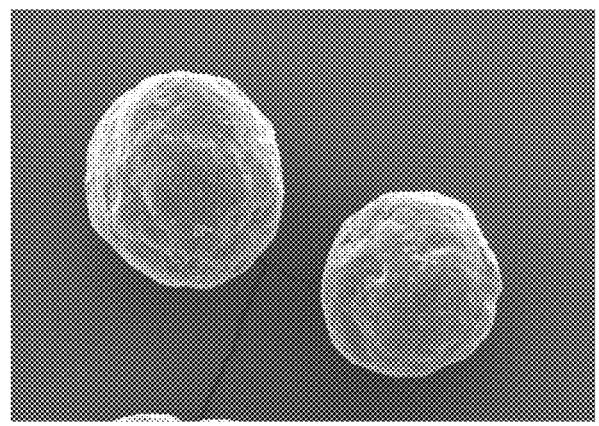
Figure 7C:
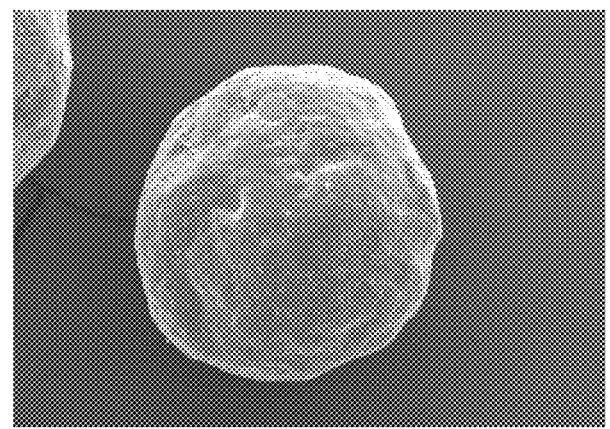
Figure 7D:
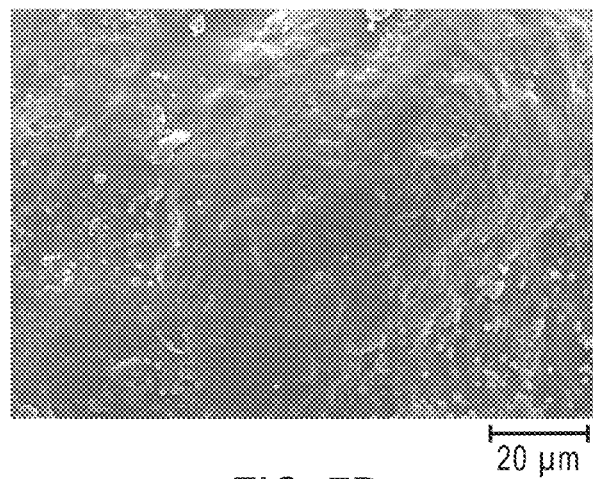
Figure 7E:
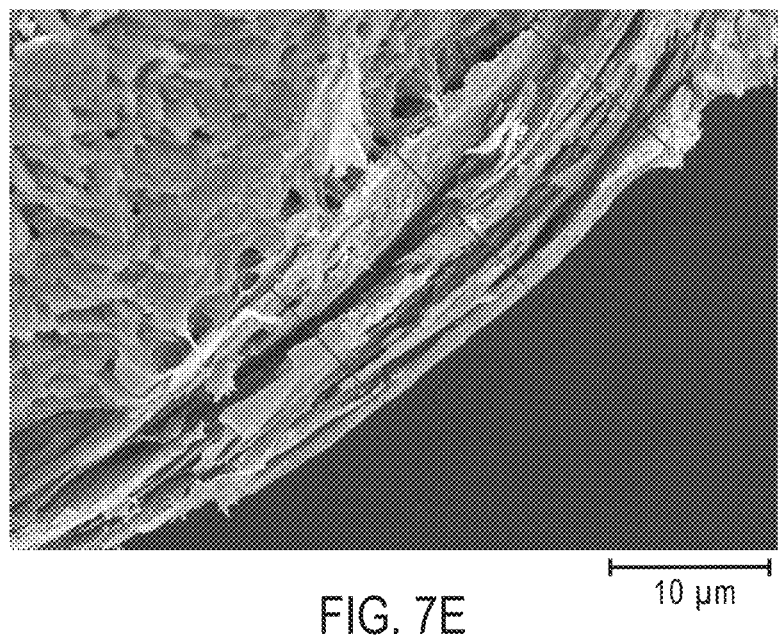
FIG. 7E shows an SEM image of a cross-section of a 40% wg coated granule as described in Example 3.

The particle size distribution is shown in FIG. 5 and the dissolution profiles are shown in FIG. 6. SEM images of the 40% wg coated granules are shown in FIGS. 7A-7D at different magnifications, and a cross-sectional view of the coating is shown in FIG. 7E.

Example 4

Granulation of 4-((L-Valyl)oxy)butanoic Acid Having a Modified Release Coating (2)

A granulation containing granules having 98.5 wt % of 4-((L-valyl)oxy)butanoic acid and characterized by a granule diameter from 225 µm to 275 µm was used.

The constituents of the modified release coating composition are provided in Table 2.

TABLE 2

| Modified release coating (2). | | |
|---|---|---|
| Constituent | Total (wt %) | Solids (wt %) |
| Ethoce ® Standard 20 ethylcellulose | 8.0 | 80 |
| Magnesium stearate | 1.6 | 16 |
| Ethanol, 96% | 81.0 | — |
| Water | 9.0 | — |
| Pharmacoat ® 603 Hydroxypropyl cellulose | 0.4 | 4 |

The processing condition for applying the modified release coating are provided in Table 3.

TABLE 3

| Process conditions. | |
|---|---|
| Parameter | Value |
| Spray Time (min) | — |
| Spray Rate (g/min) | 8-13 |
| Spray Pressure (bar) | 2.5 |
| Exhaust Temp (° C.) | — |
| Inlet Air Temp (° C.) | 35-38 |
| Atomizing Air (psi) | — |
| Process Air Flow (m³/h) | 110 |
| Inlet Air Moisture (g/kg) | 7.7-8.2 |
| Accelerator Air (psi) | — |
| Dew Point (° C.) | — |

The modified release coating was applied at 20% wg and 40% wg.

For the coated granulation having a 40% wg the bulk density was 0.63 g/mL and the LOD was 0.37%. The modified release coating thickness at 40% wg was 10.16 µm+/−2.80 µm (std).

Figure 8:
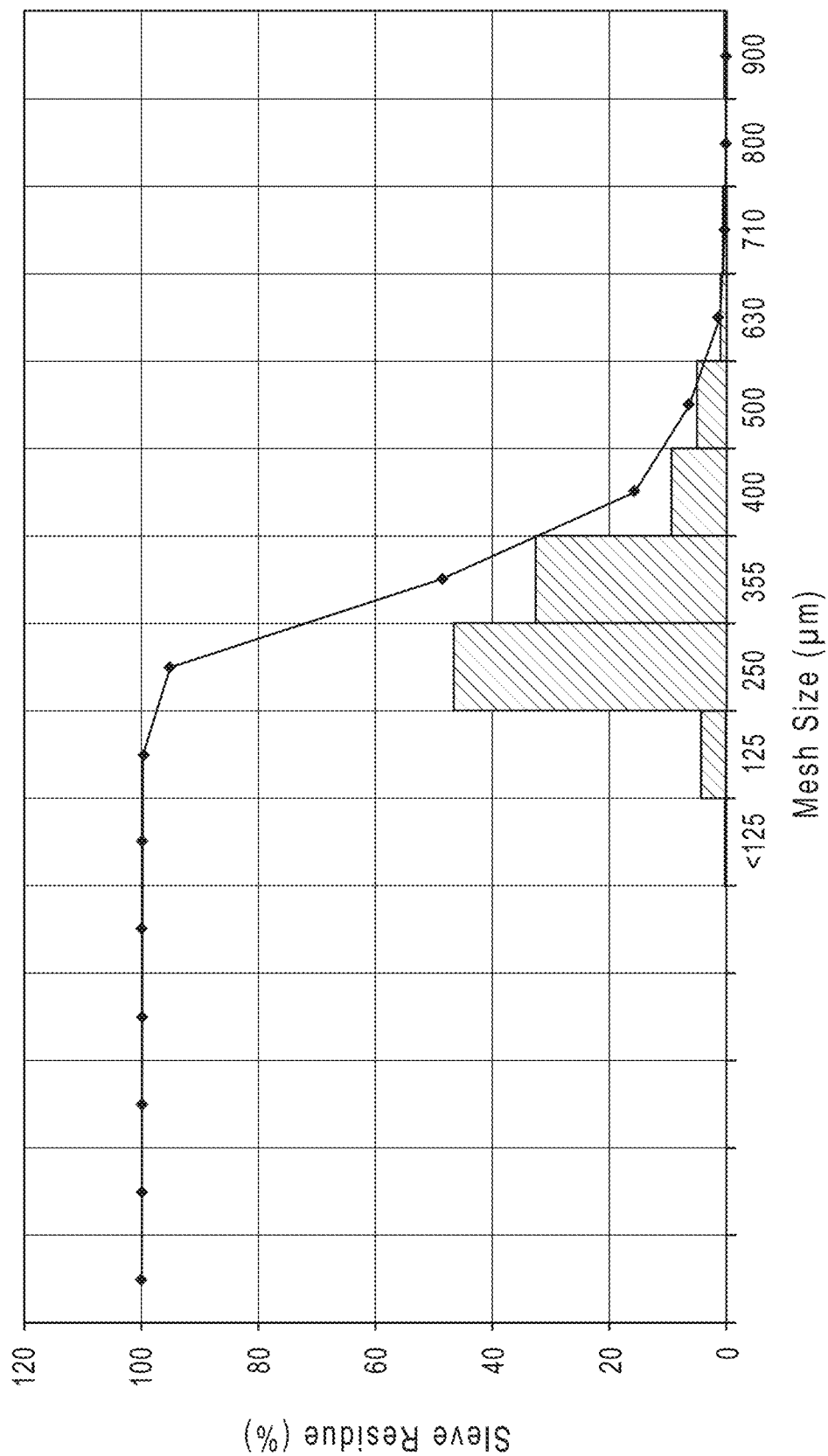
FIG. 8 shows the particle size distribution of coated granules comprising a 40% wg ethylcellulose/hydroxypropyl cellulose functional coating as described in Example 4.
Figure 10A:
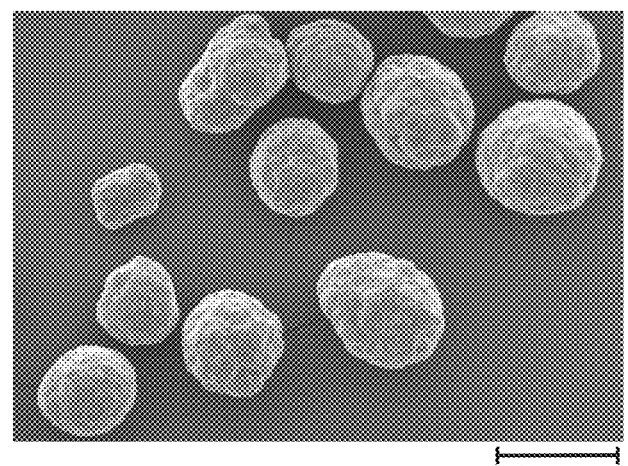
FIGS. 10A-10D show SEM images of the 40% wg coated granules at different magnifications as described in Example 4.
Figure 10B:
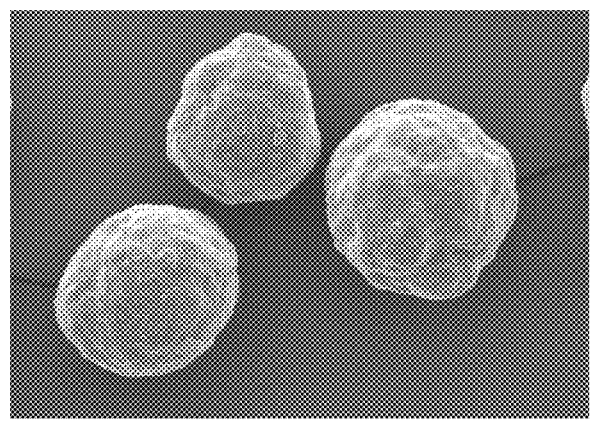
Figure 10C:
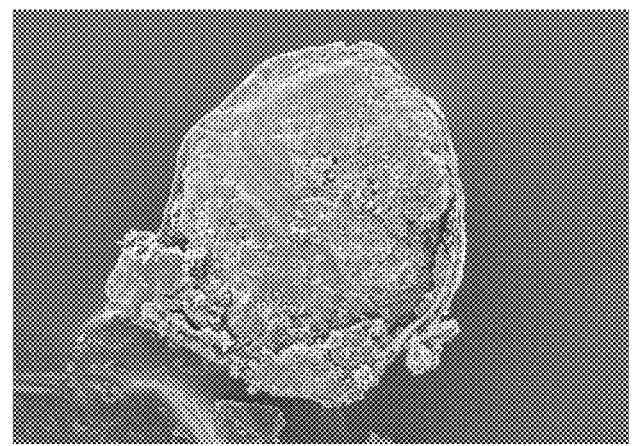
Figure 10D:
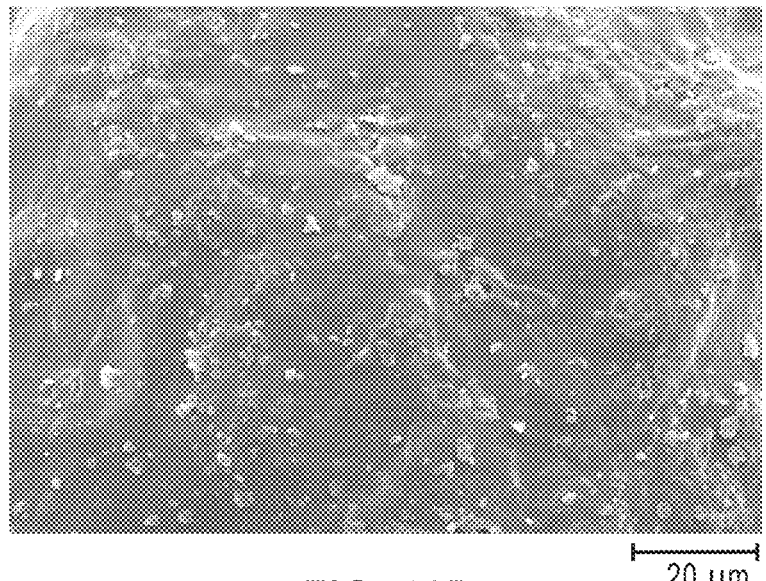
Figure 10E:
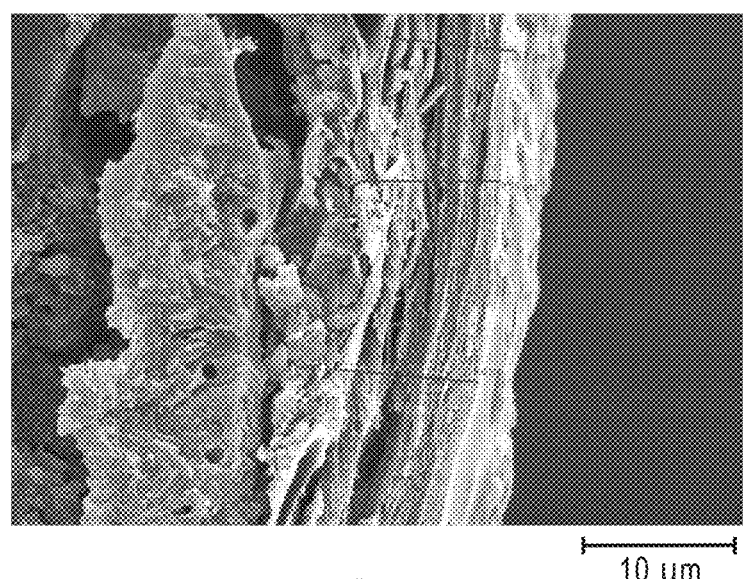
FIG. 10E shows an SEM image of a cross-section of a 40% wg coated granule as described in Example 4.

The particle size distribution is shown in FIG. 8 and the dissolution profiles are shown in FIG. 9. SEM images of the 40% wg coated granules are shown in FIGS. 10A-10D at different magnifications, and a cross-sectional view of the coating is shown in FIG. 10E.

Example 5

Granulation of 4-((L-Valyl)oxy)butanoic Acid Having a Modified Release Coating (3)

A granulation containing granules having 98.5 wt % of 4-((L-valyl)oxy)butanoic acid and characterized by a granule diameter from 200 µm to 425 µm was used.

The process conditions for applying the modified release coating were the same as those for Example 3.

The constituents of the modified release coating are provided in Table 4.

TABLE 4

Modified release coating (3).

| Constituent | Total (wt %) | Solids (wt %) |
|---|---|---|
| Ethoce ® Standard 20 Ethylcellulose | 7.03 | 81.71 |
| Ethanol, 96% | 75.8 | — |
| Water | 15.5 | — |
| Pharmacoat ® 603 Hydroxypropyl cellulose | 0.17 | 2.04 |
| Parteck ® LUB magnesium stearate | 1.4 | 16.25 |

The modified release coating was applied at 20% wg, 30% wg, 35% wg, and 40% wg.

For the coated granulation having a 40% wg the bulk density was 0.68 g/mL and the LOD was 0.69%. The modified release coating thickness at 40% wg was 11.58 µm+/−1.45 µm (std).

Figure 11:
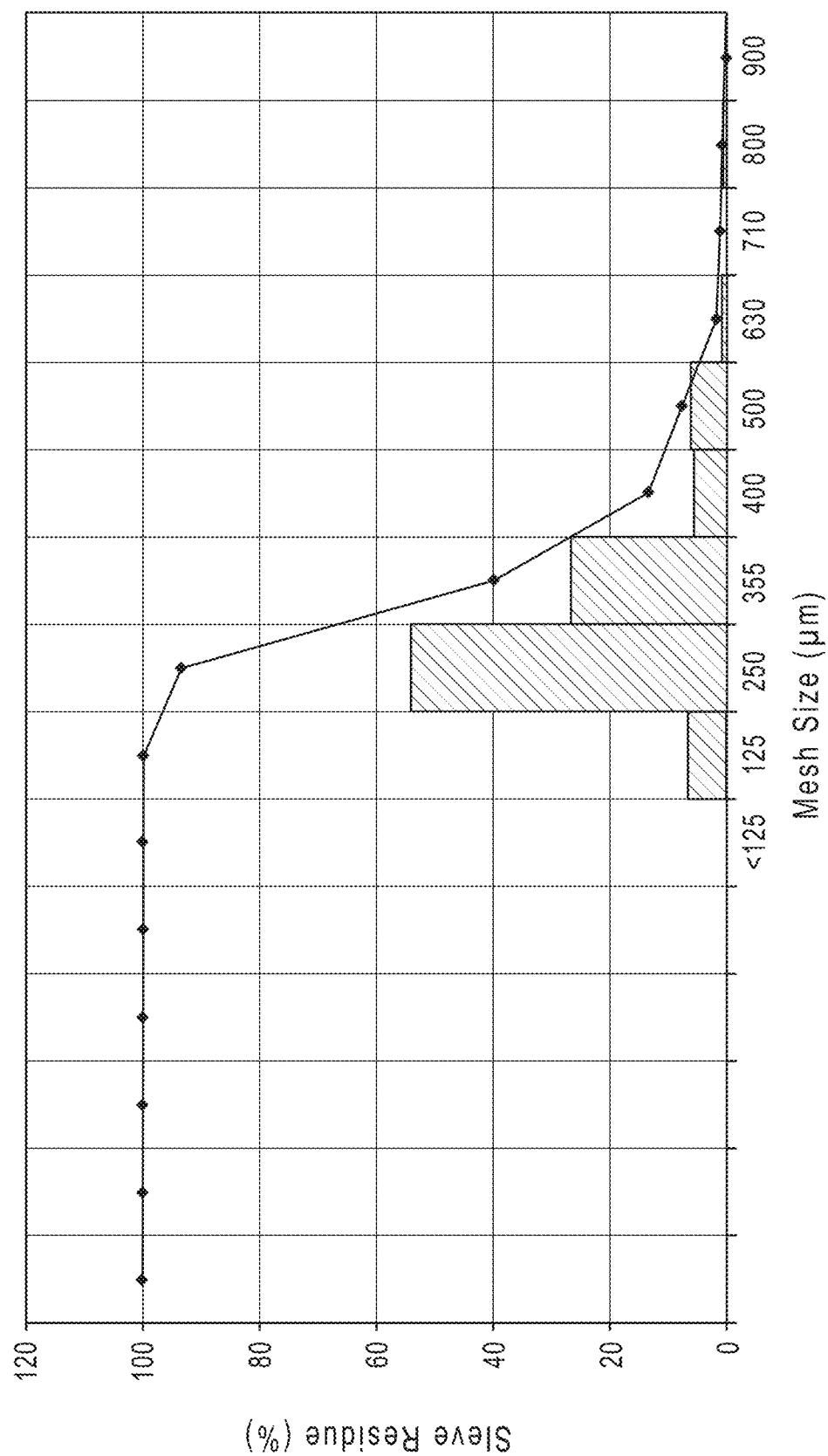
FIG. 11 shows the particle size distribution of coated granules comprising a 40% wg ethylcellulose/hydroxypropylcellulose functional coating as described in Example 5.
Figure 13A:
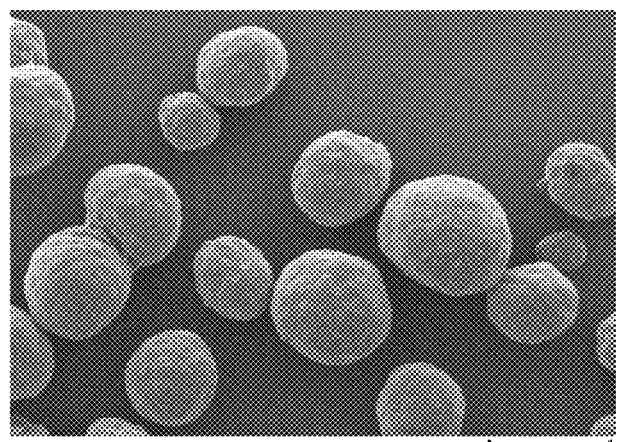
FIGS. 13A-13D show SEM images of the 40% wg coated granules at different magnifications as described in Example 5.
Figure 13B:
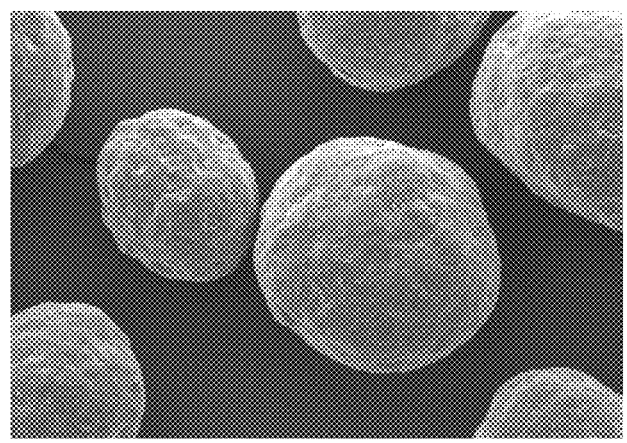
Figure 13C:
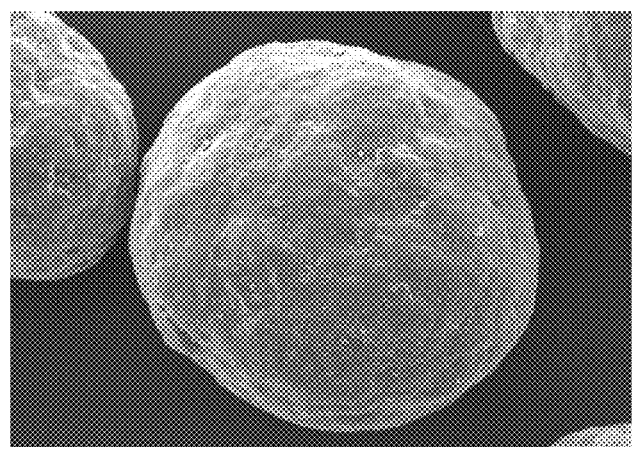
Figure 13D:
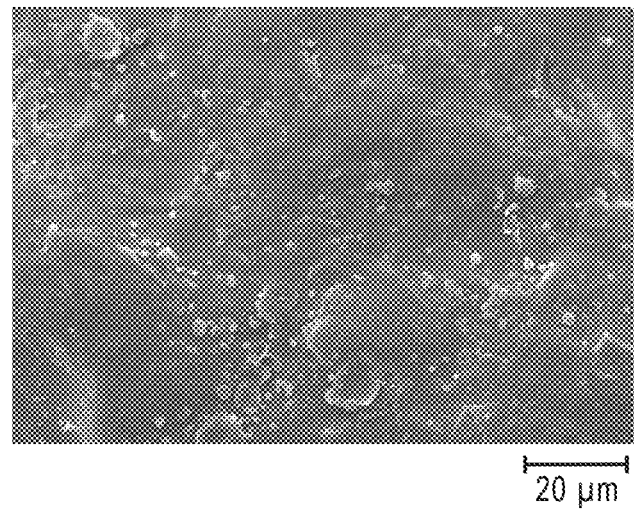
Figure 13E:
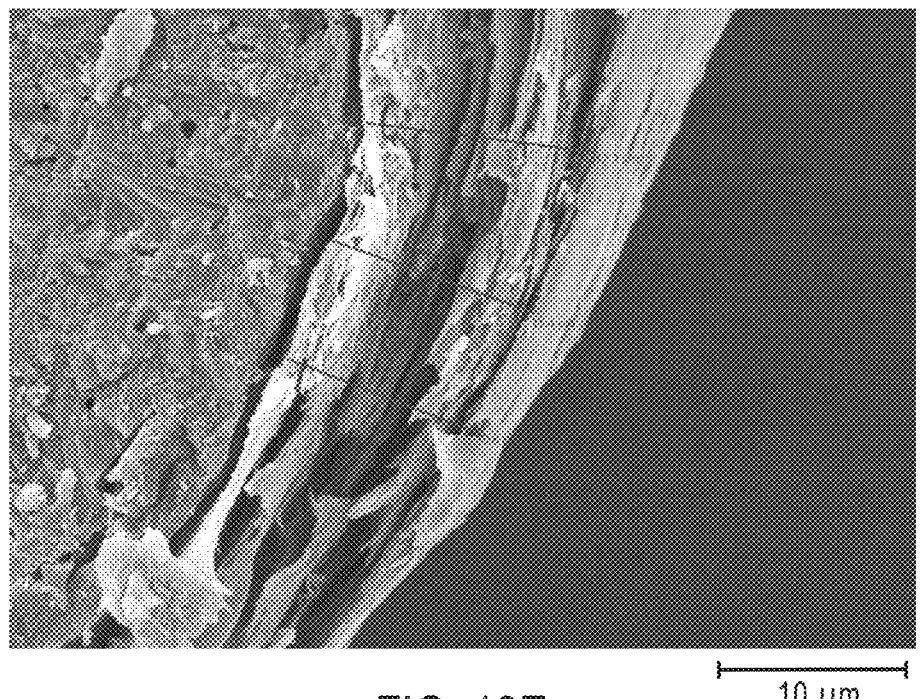
FIG. 13E shows an SEM image of a cross-section of a 40% wg coated granule as described in Example 5.

The particle size distribution is shown in FIG. 11 and the dissolution profiles are shown in FIG. 12. SEM images of the 40% wg coated granules are shown in FIGS. 13A-13D at different magnifications, and a cross-sectional view of the coating is shown in FIG. 13E.

Example 6

Coated Granulation (4)

The seal-coated granulation of Example 1 was used as the starting material.

The process conditions for applying the modified release coating were the same as those for Examples 3-5.

The constituents of the modified release coating composition are provided in Table 5.

TABLE 5

Modified release coating (4).

| Component | Total (wt %) | Solids (wt %) |
|---|---|---|
| Ethoce ® Standard 20 ethylcellulose | 8.34 | 83.4 |
| Talc | 1.66 | 16.6 |
| Ethanol, 96% | 90.00 | — |

The modified release coating was applied at 20% wg and 40% wg.

For the coated pharmaceutical granulation having a 40% wg the bulk density was 0.64 g/mL and the LOD was 0.45%. The functional coating thickness at 40% wg was 15.03 µm+/−2.24 µm (std).

Figure 14:
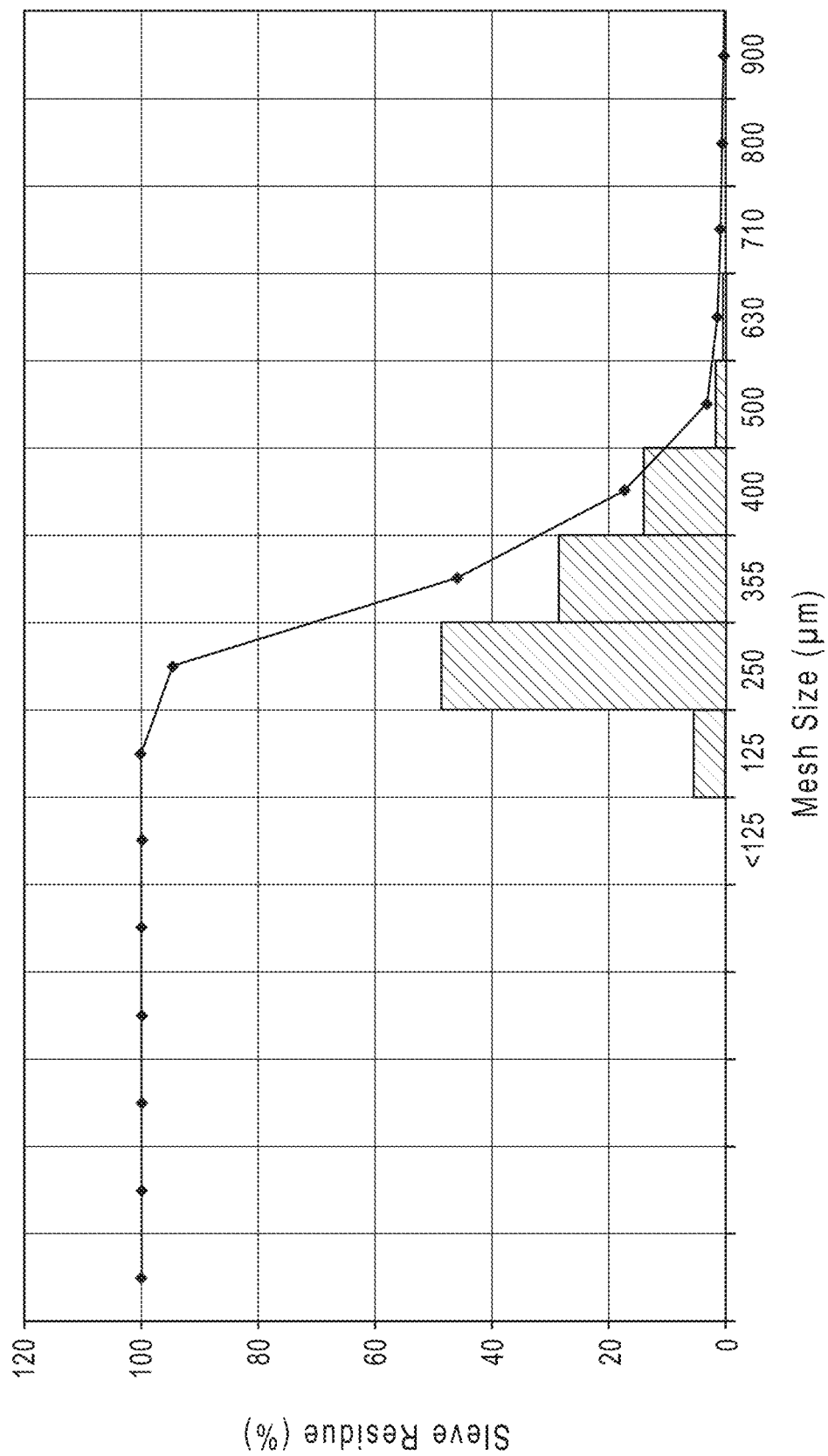
FIG. 14 shows the particle size distribution of coated granules comprising a 40% wg ethylcellulose functional coating as described in Example 6.
Figure 15:
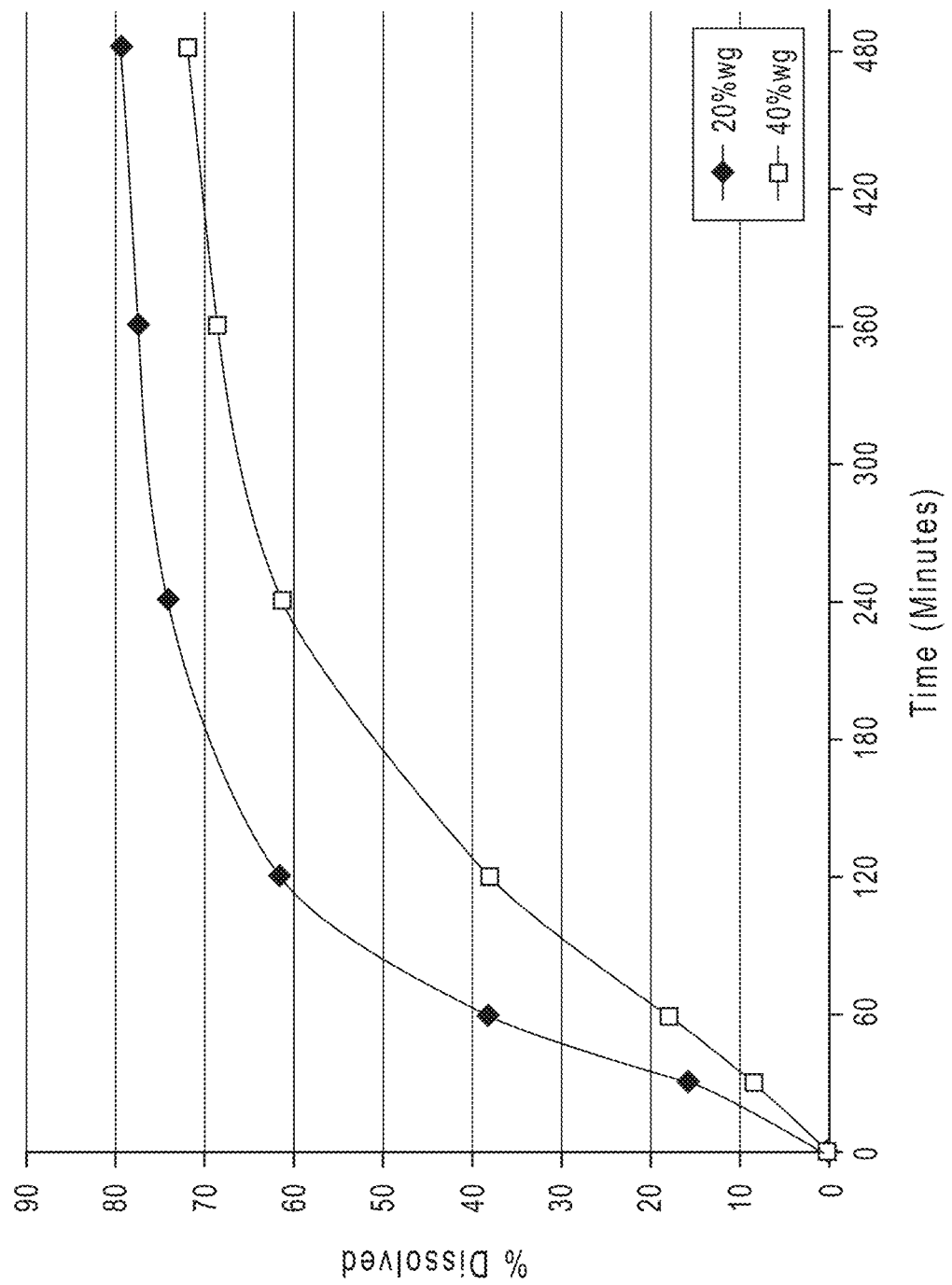
FIG. 15 shows dissolution profiles of an active pharmaceutical ingredient from granules containing an ethylcellulose functional coating representing different % wg as described in Example 6.
Figure 16A:
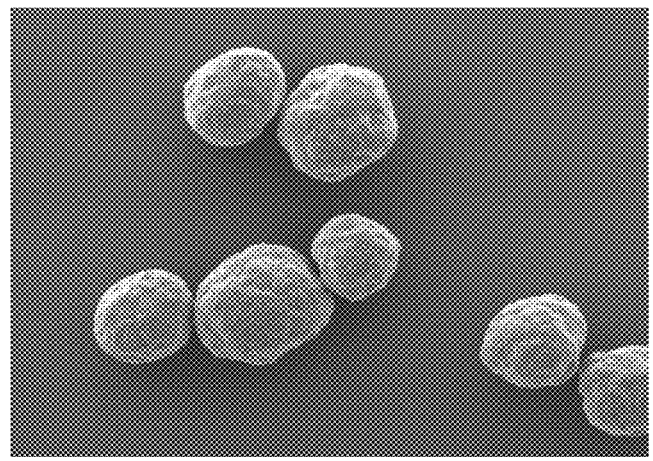
FIGS. 16A-16D show SEM images of the 40% wg coated granules at different magnifications as described in Example 6.
Figure 16B:
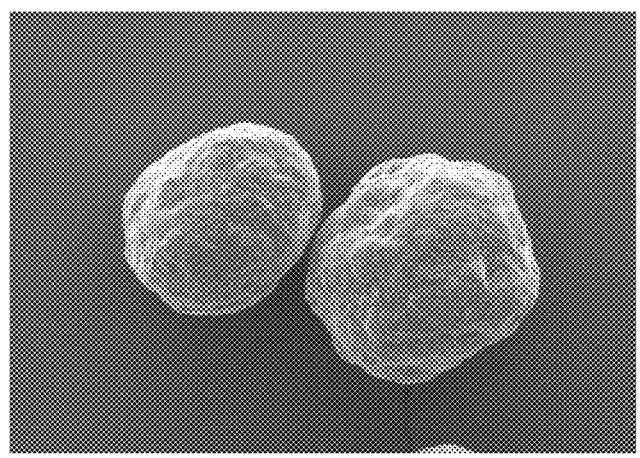
Figure 16C:
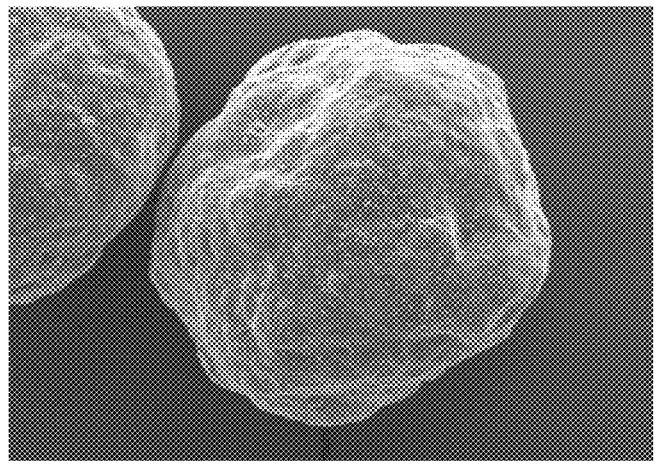
Figure 16D:
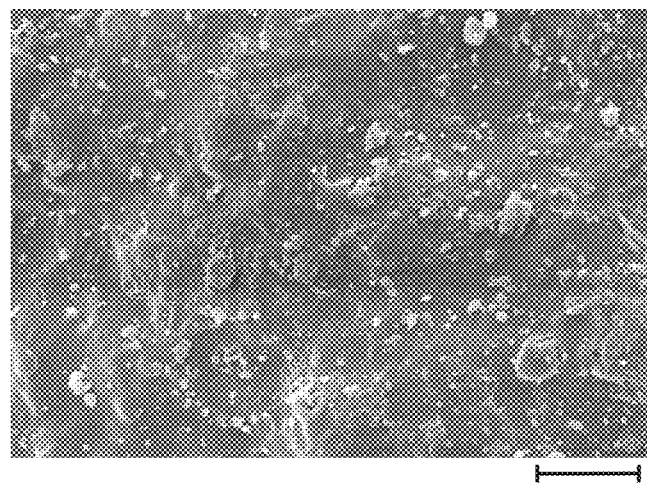
Figure 16E:
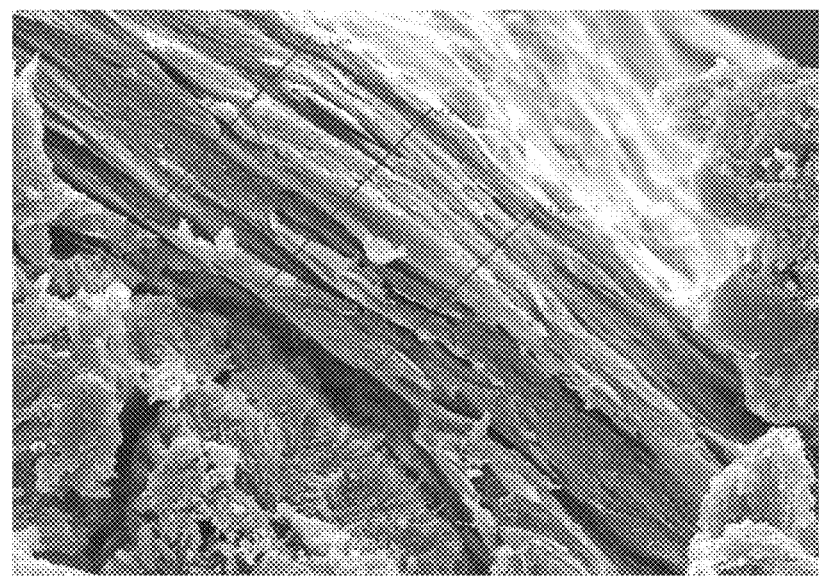
FIG. 16E shows an SEM image of a cross-section of a 40% wg coated granule as described in Example 8.

The particle size distribution is shown in FIG. 14 and the dissolution profiles are shown in FIG. 15. SEM images of the 40% wg coated granules are shown in FIGS. 16A-16D at different magnifications, and a cross-sectional view of the coating is shown in FIG. 16E.

Example 7

Pharmacokinetics of Immediate Release and Modified Release Compositions

The pharmacokinetics of compounds (1) and γ-hydroxybutyrate following oral administration of an immediate release component or modified release component to fasted, healthy subjects was determined.

To prepare an immediate release component, immediate release microparticles prepared according to Example 1 were added to 30 mL water and gently swirled to dissolve the immediate release microparticles. The uncoated IR granulation had an average granule diameter (D50) from 225 µm to 275 µm. The IR granulation contained 90 wt % 4-((L-valyl)oxy)butanoic acid, 5 wt % USP magnesium silicate, and 5 wt % hypromellose, where wt % is based on the total weight of the IR granulation. Water was added to bring the total volume to 250 mL to provide an immediate release component which was ingested by the subject.

To prepare modified release composition, modified release microparticles prepared according to Example 5 were added to 30 mL of water and gently swirled. Ora-Plus® (30 mL) was added, the contents gently swirled, and drank by the subject. Additional water up to a total volume of 250 mL was used to rinse the container and ingested by the subject. The MR1 granulation had a 60% wg coating, the MR2 granulation had a 40 wg % coating, and the MR3 granulation had a 50% wg coating. The modified release coating contained 81.7 wt % ethylcellulose, 2.0 wt % hypromellose, and 16.3 wt % magnesium stearate, where wt % is based on the total weight of the coating.

Each component contained 7.25 g of compound (1) (3.172 g-equivalents γ-hydroxybutyrate).

Plasma pharmacokinetic profiles for compound (1) and γ-hydroxybutyrate following oral administration of the immediate release (IR) or modified release (MR1-MR3) compositions to fasted, healthy subjects are shown in FIG. 17 for compound (1) and in FIG. 18 for γ-hydroxybutyrate. The results represent the mean and standard deviation based on the results for from 7 to 8 subjects.

Pharmacokinetic parameters for compound (1) and γ-hydroxybutyrate following oral administration of the compositions comprising the IR and MR microparticles are provided in Table 6 and Table 7, respectively. The results represent the mean and standard deviation based on the results for from 7 to 8 subjects.

TABLE 6

Pharmacokinetic parameters for compound (1) following oral administration of immediate release or modified release compositions.

| Composition | | $T_{max}$ (hr) | $C_{max}$ (µg/mL) | $AUC_{inf}$ (hr × µg/mL) | $AUC_{0-4}$ (hr × µg/mL) | $AUC_{0-6}$ (hr × µg/mL) | $AUC_{0-8}$ (hr × µg/mL) | $AUC_{0-12}$ (hr × µg/mL) | CL/F (L/hr) | $t_{1/2}$ (hr) |
|---|---|---|---|---|---|---|---|---|---|---|
| IR | N | 8 | 8 | 7 | 8 | 8 | 8 | 8 | 7 | 7 |
|  | Mean | 0.9 | 16 | 16 | 15 | 16 | 16 | 16 | 48 | 0.4 |
|  | SD | 1.2 | 7 | 4 | 4 | 4 | 3 | 3 | 107 | 0.2 |
| MR-1 | N | 8 | 8 | 8 | 8 | 8 | 8 | 8 | 8 | 8 |
|  | Mean | 1.6 | 4 | 9 | 8 | 9 | 9 | 9 | 838 | 0.7 |
|  | SD | 0.6 | 2 | 3 | 2 | 3 | 3 | 3 | 226 | 0.3 |

TABLE 6-continued

Pharmacokinetic parameters for compound (1) following oral administration of immediate release or modified release compositions.

| Composition | | $T_{max}$ (hr) | $C_{max}$ (μg/mL) | $AUC_{inf}$ (hr × μg/mL) | $AUC_{0-4}$ (hr × μg/mL) | $AUC_{0-6}$ (hr × μg/mL) | $AUC_{0-8}$ (hr × μg/mL) | $AUC_{0-12}$ (hr × μg/mL) | CL/F (L/hr) | $t_{1/2}$ (hr) |
|---|---|---|---|---|---|---|---|---|---|---|
| MR-2 | N | 8 | 8 | 8 | 8 | 8 | 8 | 8 | 8 | 8 |
| | Mean | 1.4 | 6 | 10 | 9 | 10 | 10 | 10 | 762 | 0.7 |
| | SD | 0.8 | 2 | 3 | 2 | 3 | 3 | 3 | 197 | 0.3 |
| MR-3 | N | 8 | 8 | 8 | 8 | 8 | 8 | 8 | 8 | 8 |
| | Mean | 1.1 | 5 | 10 | 9 | 10 | 10 | 10 | 801 | 0.8 |
| | SD | 0.7 | 2 | 3 | 2 | 3 | 3 | 3 | 220 | 0.2 |

TABLE 7

Pharmacokinetic parameters for γ-hydroxybutyrate following oral administration of immediate release or modified release compositions.

| Composition | | $T_{max}$ (hr) | $C_{max}$ (μg/mL) | $AUC_{inf}$ (hr × μg/mL) | $AUC_{0-4}$ (hr × μg/mL) | $AUC_{0-6}$ (hr × μg/mL) | $AUC_{0-8}$ (hr × μg/mL) | $AUC_{0-12}$ (hr × μg/mL) | CL/F (L/hr) | $t_{1/2}$ (hr) |
|---|---|---|---|---|---|---|---|---|---|---|
| IR | N | 8 | 8 | 8 | 8 | 8 | 8 | 8 | 8 | 8 |
| | Mean | 1.3 | 86 | 246 | 208 | 239 | 245 | 246 | 31.2 | 0.6 |
| | SD | 0.5 | 15 | 66 | 31 | 55 | 65 | 67 | 7.7 | 0.2 |
| MR1 | N | 8 | 8 | 8 | 8 | 8 | 8 | 8 | 8 | 8 |
| | Mean | 2.4 | 27 | 95 | 62 | 86 | 93 | 94 | 94.7 | 1.1 |
| | SD | 0.9 | 12 | 56 | 25 | 44 | 53 | 56 | 39.3 | 0.3 |
| MR2 | N | 8 | 8 | 8 | 8 | 8 | 8 | 8 | 8 | 8 |
| | Mean | 2.4 | 36 | 120 | 87 | 112 | 118 | 119 | 71.9 | 0.9 |
| | SD | 0.9 | 15 | 66 | 36 | 56 | 64 | 66.4 | 24.1 | 0.2 |
| MR3 | N | 8 | 8 | 8 | 8 | 8 | 8 | 8 | 8 | 8 |
| | Mean | 1.9 | 30 | 110 | 80 | 102 | 109 | 110 | 78.8 | 1.0 |
| | SD | 0.8 | 11 | 62 | 31 | 53 | 60 | 62 | 28.3 | 0.3 |

The $C_{max}$ Ratio, $AUC_{0-inf}$ Ratio, and $AUC_{0-8}$ Ratio are shown in Table 8, where the ratios refer to the ratio of the γ-hydroxybutyrate value to the corresponding compound (1) value.

TABLE 8

Pharmacokinetic ratios for immediate release and modified release compositions.

| Component | Value | $C_{max}$ Ratio | $AUC_{inf}$ Ratio | $AUC_{0-8}$ Ratio |
|---|---|---|---|---|
| IR | Mean | 5.90 | 14.99 | 16.19 |
| | SD | 2.09 | 4.80 | 5.50 |
| MR1 | Mean | 6.58 | 9.99 | 9.84 |
| | SD | 1.88 | 3.97 | 3.87 |
| MR2 | Mean | 6.34 | 11.49 | 11.47 |
| | SD | 1.76 | 3.66 | 3.55 |
| MR3 | Mean | 6.51 | 11.45 | 11.41 |
| | SD | 2.75 | 5.14 | 5.09 |

Example 8

Pharmacokinetics of Combined-Release Compositions

The pharmacokinetics of combined-release (CR) compositions comprising an immediate release microparticles (IR component) and modified release microparticles (MR component) was determined.

The amounts of the microparticles used to prepare the combined release compositions (CR1 and CR2) are summarized in Table 9.

TABLE 9

Composition of combined release compositions.

| Combined Release Composition | Compound (1) (g) | | |
|---|---|---|---|
| | IR | MR1 | MR2 |
| CR1 | 4.11 | 10.0 | — |
| CR2 | 4.11 | — | 10.0 |

To prepare combined release compositions, the amount of the immediate release microparticles was dissolved in 30 mL of water. The dose of modified release microparticles was then added and swirled gently. Thirty (30) mL of Ora-Plus®, an oral suspending vehicle, was added and the mixture swirled gently. The subjects then drank the solution. The subjects repeatedly rinsed the cup with up to 250 mL of water and drank the solution.

Plasma pharmacokinetic profiles for compound (1) and γ-hydroxybutyrate following oral administration of the combined release compositions (CR1 and CR2) to fasted, healthy subjects are shown in FIGS. 19 and 20, respectively. The results represent the mean and standard deviation based on 12 subjects.

A summary of the pharmacokinetic parameters for compound (1) and γ-hydroxybutyrate following oral administration of the combined release compositions to fasted, healthy subjects is provided in Tables 10 and 11. The results reflect mean values obtained for 12 subjects.

TABLE 10

Pharmacokinetic parameters for compound (1) following oral administration of combined release compositions.

| Composition | | $T_{max}$ (hr) | $C_{max}$ (μg/mL) | $AUC_{inf}$ (hr × μg/mL) | $AUC_{0-4}$ (hr × μg/mL) | $AUC_{0-6}$ (hr × μg/mL) | $AUC_{0-8}$ (hr × μg/mL) | $AUC_{0-12}$ (hr × μg/mL) | CL/F (L/hr) | $t_{1/2}$ (hr) |
|---|---|---|---|---|---|---|---|---|---|---|
| CR1 | N | 12 | 12 | 12 | 12 | 12 | 12 | 12 | 12 | 12 |
| | Mean | 1.4 | 15 | 27 | 22 | 25 | 26 | 27 | 556 | 1.1 |
| | SD | 1.2 | 7 | 6 | 4 | 6 | 6 | 6 | 151 | 0.7 |
| CR2 | N | 12 | 12 | 12 | 12 | 12 | 12 | 12 | 12 | 12 |
| | Mean | 1.3 | 12 | 21 | 17 | 20 | 21 | 21 | 700 | 1.0 |
| | SD | 1.0 | 4 | 5 | 4 | 4 | 4 | 5 | 152 | 0.4 |

TABLE 11

Pharmacokinetic parameters for γ-hydroxybutyrate following oral administration of combined release compositions.

| Composition | | $T_{max}$ (hr) | $C_{max}$ (μg/mL) | $AUC_{inf}$ (hr × μg/mL) | $AUC_{0-4}$ (hr × μg/mL) | $AUC_{0-6}$ (hr × μg/mL) | $AUC_{0-8}$ (hr × μg/mL) | $AUC_{0-12}$ (hr × μg/mL) | CL/F (L/hr) | $t_{1/2}$ (hr) |
|---|---|---|---|---|---|---|---|---|---|---|
| CR1 | N | 12 | 12 | 12 | 12 | 12 | 12 | 12 | 12 | 12 |
| | Mean | 2.7 | 108 | 534 | 271 | 400 | 464 | 512 | 32 | 1.1 |
| | SD | 0.9 | 25 | 268 | 51 | 88 | 142 | 218 | 15 | 0.9 |
| CR2 | N | 12 | 12 | 12 | 12 | 12 | 12 | 12 | 12 | 12 |
| | Mean | 2.2 | 83 | 386 | 221 | 322 | 348 | 365 | 43 | 0.9 |
| | SD | 0.8 | 20 | 165 | 66.2 | 103 | 121 | 136 | 20 | 0.5 |

The $C_{max}$ Ratio, $AUC_{0-inf}$ Ratio and $AUC_{0-8}$ Ratio for the combined release compositions are shown in Table 12, where the ratios refer to the ratio of the γ-hydroxybutyrate value to the corresponding compound (1) value.

TABLE 12

Pharmacokinetic ratios for combined release compositions.

| Composition | Value | $C_{max}$ Ratio | $AUC_{inf}$ Ratio | $AUC_{0-8}$ Ratio |
|---|---|---|---|---|
| IR | Mean | 5.90 | 14.99 | 16.19 |
| | SD | 2.09 | 4.80 | 5.50 |
| MR1 | Mean | 6.58 | 9.99 | 9.84 |
| | SD | 1.88 | 3.97 | 3.87 |
| MR2 | Mean | 6.34 | 11.49 | 11.47 |
| | SD | 1.76 | 3.66 | 3.55 |
| MR3 | Mean | 6.51 | 11.45 | 11.41 |
| | SD | 2.75 | 5.14 | 5.09 |

It should be noted that there are alternative ways of implementing the embodiments disclosed herein. Accordingly, the present embodiments are to be considered as illustrative and not restrictive. Furthermore, the claims are not to be limited to the details given herein and are entitled their full scope and equivalents thereof.

The invention claimed is:

1. A pharmaceutical composition comprising:
(a) an immediate release component, wherein the immediate release component comprises:
from 2 g to 8 g of 4-((L-valyl)oxy)butanoic acid; and
a plurality of granules, wherein,
the granules comprise greater than 80 wt % of 4-((L-valyl)oxy)butanoic acid, wherein wt % is based on the total weight of the granules; and
the granules have an average particle diameter (D50) from 75 μm to 450 μm as determined by sieve analysis or by laser diffraction; and (b) a modified release component, wherein the modified release component comprises:
from 8 g to 16 g of 4-((L-valyl)oxy)butanoic acid; and
a plurality of coated granules, wherein,
the coated granules have an average particle diameter (D50) from 150 μm to 400 μm as determined by sieve analysis or by laser diffraction;
the coated granules comprise a core and a modified release coating surrounding the core;
the core comprises greater than 85 wt % of 4-((L-valyl)oxy)butanoic acid, wherein wt % is based on the total weight of the core; and
the modified release coating comprises:
from 70 wt % to 95 wt % of a matrix polymer; and
from 5 wt % to 30 wt % of a first antistatic agent;
wherein wt % is based on the total weight of the modified release coating.

2. The pharmaceutical composition of claim 1, wherein the core comprises greater than 90 wt % of γ-((L-valyl)oxy) butanoic acid, wherein wt % is based on the total weight of the core.

3. The pharmaceutical composition of claim 1, wherein the core comprises:
greater than 85 wt % of γ-((L-valyl)oxy)butanoic acid;
from 1 wt % to 10 wt % of a second antistatic agent; and
from 1 wt % to 10 wt % of a water-soluble polymer,
wherein wt % is based on the total weight of the core.

4. The pharmaceutical composition of claim 3, wherein,
the second antistatic agent comprises talc; and
the water-soluble polymer comprises hydroxypropylmethyl cellulose.

5. The pharmaceutical composition of claim 1, wherein the matrix polymer comprises a water-soluble polymer and a water insoluble polymer.

6. The pharmaceutical composition of claim 5, wherein the modified release coating comprises:
from 72 wt % to 92 wt % of the water-insoluble polymer; and
from 0.1 wt % to 10 wt % of the water-soluble polymer, wherein wt % is based on the total weight of the modified release coating.

7. The pharmaceutical composition of claim 5, wherein,
the water-insoluble polymer comprises ethylcellulose; and
the water-soluble polymer comprises hydroxypropyl cellulose.

8. The pharmaceutical composition of claim 1, wherein the first antistatic agent is selected from the group consisting of talc, magnesium stearate, and a combination thereof.

9. The pharmaceutical composition of claim 1, wherein the coated granules comprise:
from 65 wt % to 85 wt % of the core; and
from 15 wt % to 40 wt % of the modified release coating;
wherein wt % is based on the total weight of the coated granules.

10. The pharmaceutical composition of claim 1, wherein the modified release coating does not comprise a plasticizer.

11. The pharmaceutical composition of claim 1, wherein the pharmaceutical composition comprises from 10 g to 20 g of 4-((L-valyl)oxy)butanoic acid.

12. The pharmaceutical composition of claim 1, wherein the pharmaceutical composition comprises the modified release component suspended in a solution of the immediate release component.

13. The pharmaceutical composition of claim 1, wherein the coated granules comprise from 10 wt % to 50 wt % of the modified release coating, wherein wt % is based on the total weight of the coated granules.

14. The pharmaceutical composition of claim 1, wherein the matrix polymer comprises:
from 92 wt % to 98 wt % of a water-insoluble polymer; and
from 2 wt % to 8 wt % of a water-soluble polymer.

15. The pharmaceutical composition of claim 1, wherein the first antistatic agent is talc.

16. The pharmaceutical composition of claim 1, wherein the first antistatic agent is magnesium stearate.

17. The pharmaceutical composition of claim 1, wherein the modified release coating comprises a plasticizing agent.

18. The pharmaceutical composition of claim 17, wherein the plasticizing agent is dibutyl sebacate.

* * * * *